(12) United States Patent
Daniyan et al.

(10) Patent No.: US 11,766,474 B2
(45) Date of Patent: Sep. 26, 2023

(54) IL-36 SECRETING IMMUNORESPONSIVE CELLS AND USES THEREOF

(71) Applicant: MEMORIAL SLOAN-KETTERING CANCER CENTER, New York, NY (US)

(72) Inventors: Anthony Daniyan, New York, NY (US); Renier J. Brentjens, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 266 days.

(21) Appl. No.: 15/930,966

(22) Filed: May 13, 2020

(65) Prior Publication Data

US 2020/0330574 A1 Oct. 22, 2020

Related U.S. Application Data

(63) Continuation of application No. PCT/US2018/061003, filed on Nov. 14, 2018.

(60) Provisional application No. 62/585,879, filed on Nov. 14, 2017.

(51) Int. Cl.
*A61K 39/00* (2006.01)
*A61P 35/00* (2006.01)

(52) U.S. Cl.
CPC ....... *A61K 39/001112* (2018.08); *A61P 35/00* (2018.01); *A61K 2039/5158* (2013.01); *A61K 2039/55527* (2013.01); *A61K 2039/585* (2013.01)

(58) Field of Classification Search
CPC .......... A61K 2039/55522; A61K 2039/55527; A61K 2039/585; A61K 35/17; A61K 38/20; A61K 39/0011; A61K 39/001112; A61P 35/00; C07K 14/54; C07K 14/4748; C07K 2319/02; C12N 2501/23; C12N 5/0636; C12N 2510/00
See application file for complete search history.

(56) References Cited

U.S. PATENT DOCUMENTS

| | | | |
|---|---|---|---|
| 4,956,778 A | 9/1990 | Naito | |
| 5,091,513 A | 2/1992 | Huston et al. | |
| 5,132,405 A | 7/1992 | Huston et al. | |
| 5,399,346 A | 3/1995 | Anderson et al. | |
| 7,446,190 B2 | 11/2008 | Sadelain et al. | |
| 10,172,808 B2 * | 1/2019 | Frederick | A61K 38/2086 |
| 2005/0196754 A1 | 9/2005 | Drmanac et al. | |
| 2013/0071414 A1 | 3/2013 | Dotti et al. | |
| 2015/0283178 A1 | 10/2015 | June et al. | |
| 2017/0224798 A1 | 8/2017 | Cooper et al. | |

FOREIGN PATENT DOCUMENTS

| | | |
|---|---|---|
| WO | WO 2015/157384 A1 | 10/2015 |
| WO | WO 2016/090312 A1 | 6/2016 |
| WO | WO 2016/090320 A1 | 6/2016 |
| WO | WO 2017/075537 A1 | 5/2017 |

OTHER PUBLICATIONS

Tsurutani et al. J. Immunology 2016, vol. 196, (1), pp. 124-134.*
Altschul et al., "Basic Local Alignment Search Tool," J. Mol. Biol. 215:403-410 (1990).
Altschul et al., "Gapped BLAST and PSI-BLAST: a new generation of protein database search programs," Nucleic Acids Res. 25(17):3389-3402 (1997).
Anderson, "Prospects for Human Gene Therapy," Science 226(4673):401-409 (1984).
Benton et al., "Screening Xgt Recombinant Clones by Hybridization to Single Plaques in situ," Science 196(4286):180-182 (1977).
Berger and Kimmel, "Guide to Molecular Cloning Techniques," Academic Press, New York, pp. 3-812 (1987).
Blömer et al., "Highly Efficient and Sustained Gene Transfer in Adult Neurons with a Lentivirus Vector," Journal of Virology 71(9):6641-6649 (1997).
Bregni et al., "Human Peripheral Blood Hematopoietic Progenitors Are Optimal Targets of Retroviral-Mediated Gene Transfer," Blood 80(6):1418-1422 (1992).
Brocks et al., "A TNF receptor antagonistic scFv, which is not secreted in mammalian cells, is expressed as a soluble mono- and bivalent scFv derivative in insect cells," Immunotechnology 3:173-184 (1997).
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).
Cornetta et al., "Gene Transfer into Primates and Prospects for Gene Therapy in Humans," Progress in Nucleic Acid Research and Molecular Biology 36:311-322 (1987).
Danos et al., "Safe and efficient generation of recombinant retroviruses with amphotropic and ecotropic host ranges," PNAS USA 85:6460-6464 (1988).
Dupont et al., "Artificial Antigen-Presenting Cells Transduced with Telomerase Efficiently Expand Epitope-Specific, Human Leukocyte Antigen-Restricted Cytotoxic T Cells," Cancer Res 65:5417-5427 (2005).
Eglitis et al., "Retroviral Vectors for Introduction of Genes into Mammalian Cells," BioTechniques 6(7):608-614 (1988).

(Continued)

*Primary Examiner* — Bao Q Li
(74) *Attorney, Agent, or Firm* — Baker Botts L.L.P.

(57) ABSTRACT

The present disclosure provides methods and compositions for enhancing the immune response toward cancers and pathogens. It relates to an immunoresponsive cell comprising an antigen-recognizing receptor (e.g., a chimeric antigen receptor (CAR) or a T cell receptor (TCR)), and expressing increased level of IL-36. In certain embodiments, the engineered immunoresponsive cells are antigen-directed and have enhanced immune-activating properties.

24 Claims, 14 Drawing Sheets

Specification includes a Sequence Listing.

(56) References Cited

OTHER PUBLICATIONS

Felgner et al., "Lipofection: a highly efficient, lipid-mediated DNA-transfection procedure," PNAS USA 84:7413-7417 (1987).
Fife et al., "Inhibition of T cell activation and autoimmune diabetes using a B cell surface-linked CTLA-4 agonist," J Clin Invest 116(8):2252-2261 (2006).
Friedmann, "Progress toward Human Gene Therapy," Science 244(4910):1275-1281 (1989).
Giomarelli et al., "Inhibition of thrombin-induced platelet aggregation using human single-chain Fv antibodies specific for TREM-like transcript- I," Thromb Haemost 97:955-963 (2007).
Grunstein et al., "Colony hybridization: a method for the isolation of cloned DNAs that contain a specific gene," PNAS USA 72(10):3961-3965 (1975).
Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Hughes et al., "Retroviral Gene Transfer to Primitive Normal and Leukemic Hematopoietic Cells Using Clinically Applicable Procedures," J. Clin. Invest. 89:1817-1824 (1992).
Huston et al., "Protein engineering of antibody binding sites: Recovery of specific activity in an anti-digoxin single-chain Fv analogue produced in *Escherichia coli*," PNAS USA 85:5879-5883 (1988).
International Search Report and Written Opinion dated Mar. 5, 2019 in corresponding International Patent Application No. PCT/US2018/061003.
Johnson, "Gene Therapy for Cystic Fibrosis," Chest 107:77S-83S (1995).
Kabat et al., "Sequences of Proteins of Immunological Interest," Fifth Edition, U.S. Department of Health and Human Services, NIH Publication No. 91-3242 (1991).
Kido et al., "Use of a retroviral vector with an internal opsin promoter to direct gene expression to retinal photoreceptor cells," Current Eye Research 15:833-844 (1996).
Kimmel, "Identification and Characterization of Specific Clones: Strategy for Confirming the Validity of Presumptive Clones," Methods Enzymol 152:507-511 (1987).
Le Gal La Salle et al., "An Adenovirus Vector for Gene Transfer into Neurons and Glia in the Brain," Science 259(5097):988-990 (1993).
Ledbetter et al., "Agonistic Activity of a CD4O-Specific Single-Chain Fv Constructed from the Variable Regions of mAb G28-5," Crit Rev Immunol. 17:427-435 (1997).
Meyers et al., "Optimal alignments in linear space," Comput. Appl. Biosci., 4:11-17 (1988).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Redesign of Retrovirus Packaging Cell Lines to Avoid Recombination Leading to Helper Virus Production," Mol. Cell. Biol. 6(8):2895-2902 (1986).
Miller et al., "Improved Retroviral Vectors for Gene Transfer and Expression," Biotechniques 7(9):980-990 (1989).
Miller, "Retrovirus Packaging Cells," Human Gene Therapy 1:5-14 (1990).
Miyoshi et al., "Stable and efficient gene transfer into the retina using an HIV-based lentiviral vector," PNAS USA 94:10319-10323 (1997).
Moen, "Directions in Gene Therapy," Blood Cells 17:407-416 (1991).
Moosmayer et al., "A single-chain TNF receptor antagonist is an effective inhibitor of TNF mediated cytotoxicity," Therapeutic Immunol. 2:31-40 (1995).
Morgan et al., "Cancer Regression in Patients After Transfer of Genetically Engineered Lymphocytes," Science 314:126-129 (2006).
Naldini et al., "In Vivo Gene Delivery and Stable Transduction of Nondividing Cells by a Lentiviral Vector," Science 272(5259):263-267 (1996).
Needleman and Wunsch (J. Mol. Biol. 48:443-453 (1970).
Ono et al., "Plasmid DNAs directly injected into mouse brain with lipofectin can be incorporated and expressed by brain cells," Neuroscience Letters, 117:259-263 (1990).
Panelli et al., "A Tumor-Infiltrating Lymphocyte from a Melanoma Metastasis with Decreased Expression of Melanoma Differentiation Antigens Recognizes MAGE-12," J Immunol 164:4382-4392 (2000).
Panelli et al., "Expansion of Tumor-T Cell Pairs from Fine Needle Aspirates of Melanoma Metastases," J Immunol 164:495-504 (2000).
Papanicolaou et al., "Rapid expansion of cytomegalovirus-specific cytotoxic T lymphocytes by artificial antigen-presenting cells expressing a single HLA allele," Blood 102:2498-2505 (2003).
Pegram et al., "Tumor-targeted T cells modified to secrete IL-12 eradicate systemic tumors without need for prior conditioning," Blood 119 (18) 4133-4141 (2012).
Peter et al., "Protective effects of an anti-melanocortin-4 receptor scFv derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the 132-Adrenergic Receptor," J Biol. Chem. 278(38):36740-36747 (2003).
Rosenberg et al., "Gene Transfer into Humans," N. Engl. J. Med 323(9):570-578 (1990).
Sadelain et al., "Targeting Tumours With Genetically Enhanced T Lymphocytes," Nat Rev Cancer 3:35-45 (2003).
Sambrook et al., "Molecular Cloning: a Laboratory Manual," second edition, Cold Spring Harbor Laboratory Press, New York (1989).
Sharp, "Gene Therapy," the Lancet 337:1277-1278 (1991).
Shieh et al., "Transgenic Expression of Single-Chain Anti-CTLA-4 Fv on β Cells Protects Nonobese Diabetic Mice from Autoimmune Diabetes," J Immunol 183:2277-2285 (2009).
Singleton et al., Dictionary of Microbiology and Molecular Biology (2nd ed. 1994).
Straubinger et al., "Liposomes as Carriers for Intracellular Delivery of Nucleic Acids," Methods in Enzymology, 101:512-527 (1983).
The Polymerase Chain Reaction. Mullis (1994).
Tolstoshev et al., "Gene expression using retroviral vectors," Current Opinion in Biotechnology 1:55-61 (1990).
Wahl et al., "Improved Radioimaging and Tumor Localization with Monoclonal F(ab')2," J. Nucl. Med. 24:316-325 (1983).
Wahl et al., "Molecular Hybridization of Immobilized Nucleic Acids: Theoretical Concepts and Practical Considerations," Methods Enzymol 152:399-407 (1987).
Wolff et al., "Direct Gene Transfer into Mouse Muscle in Vivo," Science 247(4949):1465-1468 (1990).
Wu et al., "Receptor-mediated Gene Delivery and Expression in Vivo," Journal of Biological Chemistry, 263(29):14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Xie et al., "Direct demonstration of MuSK involvement in acetylcholine receptor clustering through identification of agonist ScFv," Nat Biotech 15:768-771 (1997).
Xu et al., "Correction of the enzyme deficiency in hematopoietic cells of Gaucher patients using a clinically acceptable retroviral supernatant transduction protocol," Exp. Hemat. 22:223-230 (1994).
Zhao et al., "Characteristics of an scFv Antibody Fragment That Binds to Immunoglobulin G of Graves' Disease Patients and Inhibits Autoantibody-Mediated Thyroid-Stimulating Activity," Hybridoma 27(6):445-451 (2008).
Hu et al., "Chimeric antigen receptor (CAR)-transduced natural killer cells in tumor immunotherapy," Acta Pharmacologica Sinica, 39(2): 167-176 (2018).
Shiva Solahaye-Kahnamouii et al., "The Effect of Interleukin 36 Gene Therapy in the Regression of Tumor," Iran J of Cancer Prev, 7(4):197-203 (2014).
Supplementary European Search Report dated May 26, 2021 in Application No. EP18878826.
He et al., "Amplified interleukin-15 expression vectors for cancer immunogene therapy," Molecular Medicine Reports 1:369-374 (2008).

* cited by examiner

IL-36 SECRETING IMMUNORESPONSIVE CELLS AND USES THEREOF

CROSS-REFERENCE TO RELATED APPLICATION

This application is a Continuation of International Patent Application No. PCT/US18/061003 filed on Nov. 14, 2018, which claims priority to U.S. Provisional Application No. 62/585,879 filed on Nov. 14, 2017, the contents of each of which are hereby incorporated by reference in their entireties, and to each of which priority is claimed.

SEQUENCE LISTING

The specification further incorporates by reference the Sequence Listing submitted herewith via EFS on May 13, 2020. Pursuant to 37 C.F.R. § 1.52(e)(5), the Sequence Listing text file, identified as 0727341071_SL.txt, is 100,316 bytes and was created on May 12, 2020. The Sequence Listing electronically filed herewith, does not extend beyond the scope of the specification and thus does not contain new matter.

INTRODUCTION

The presently disclosed subject matter provides methods and compositions for enhancing the immune response toward cancers and pathogens. It relates to immunoresponsive cells comprising antigen-recognizing receptors (e.g., chimeric antigen receptors (CARs) or T cell receptors (TCRs)) that are engineered to express an IL-36 polypeptide. These engineered immunoresponsive cells are antigen-directed, promote recruitment of other cytokines and exhibit enhanced anti-target efficacy.

BACKGROUND OF THE INVENTION

The majority of adult B-cell malignancies, including acute lymphoblastic leukemia (ALL), chronic lymphocytic leukemia, and non-Hodgkin's lymphoma, are incurable despite currently available therapies. Adoptive therapy with genetically engineered autologous T cells has shown evidence of therapeutic efficacy in melanoma and indolent B cell malignancies. T cells may be modified to target tumor-associated antigens through the introduction of genes encoding artificial T-cell receptors, termed chimeric antigen receptors (CAR), specific to such antigens. Immunotherapy is a targeted therapy that has the potential to provide for the treatment of cancer.

However, malignant cells adapt to generate an immunosuppressive microenvironment to protect themselves from immune recognition and elimination. This "hostile" tumor microenvironment poses a challenge to methods of treatment involving stimulation of an immune response, such as targeted T cell therapies. Various modifications have been made toward improving the antitumor effect of CAR- or TCR-engineered T cells. For example, Pegram et al. describes a murine model of CAR-engineered T cells that constitutively secrete interleukin 12 (IL-12) and showed increased cytotoxicity towards CD19$^+$ tumor cells (Pegram et al., BLOOD, Vol. 119, No. 18, 2012). However, the secretion of IL-12 led to suppression of interleukin 2 (IL-2), an important cytokine that promotes the proliferation and anti-tumor effect of T and B lymphocytes. Dotti et al. discloses CAR-engineered T cells that constitutively secrete interleukin 15 (IL-15) and an inducible caspase-9 based suicide gene (iC9), which showed increase cytotoxicity towards CD19$^+$ tumor cells (US 20130071414 A1). This modified CAR-T cell demonstrated unchanged levels of IL-2 expression both in vivo and in vitro. Accordingly, novel therapeutic strategies for treating neoplasia are urgently required.

SUMMARY OF THE INVENTION

The presently disclosed subject matter provides immunoresponsive cells (e.g., T cells, Tumor Infiltrating Lymphocytes, Natural Killer (NK) cells, cytotoxic T lymphocytes (CTLs), Natural Killer T (NK-T) cells or regulatory T cells) that (a) express an antigen-recognizing receptor (e.g., CAR or TCR) directed toward a target antigen of interest, and (b) express (and secrete) an interleukin 36 ("IL36") polypeptide (e.g., IL-36 alpha, IL-36 beta and/or IL-36 gamma). In certain non-limiting embodiments, the immunoresponsive cell comprises a nucleotide acid encoding an IL-36 polypeptide (e.g., IL-36 polypeptide-encoding nucleic acid), in expressible form.

The presently disclosed subject matter also provides an immunoresponsive cell comprising (a) an antigen-recognizing receptor (e.g., CAR or TCR) directed toward a target antigen of interest, and (b) a modified promoter at an endogenous (native) IL-36 gene locus, wherein the modified promoter enhances the gene expression of the endogenous IL-36 gene locus. In certain non-limiting embodiments, the modification comprises replacement of an endogenous promoter with a constitutive promoter or an inducible promoter, or insertion of a constitutive promoter or inducible promoter to the promoter region of the endogenous IL-36 gene locus. In certain non-limiting embodiments, the constitutive promoter is selected from the group consisting of a CMV promoter, an EF1a promoter, a SV40 promoter, a PGK1 promoter, a Ubc promoter, a beta-actin promoter, and a CAG promoter. In certain non-limiting embodiments, the inducible promoter is selected from the group consisting of a tetracycline response element (TRE) promoter and an estrogen response element (ERE) promoter.

In certain embodiments, the immunoresponsive cell constitutively expresses the IL-36 polypeptide (mature or non-mature form of IL-36 protein). In certain embodiments, the IL-36 polypeptide is secreted. The antigen-recognizing receptor can be a TCR or a CAR. In certain embodiments, the antigen-recognizing receptor is a CAR. In certain embodiments, the immunoresponsive cell is selected from the group consisting of a T cell, a Natural Killer (NK) cell, a cytotoxic T lymphocyte (CTL), a regulatory T cell, a Natural Killer T (NK-T) cell, a human embryonic stem cell, and a pluripotent stem cell from which lymphoid cells may be differentiated. In certain embodiments, the immunoresponsive cell is autologous.

Furthermore, the presently disclosed subject matter provides methods of using such immunoresponsive cells for inducing and/or enhancing an immune response, and/or for treating and/or preventing a neoplasm (e.g., cancer), infectious disease, and other diseases/disorders that would benefit from an augmented immune response.

In certain non-limiting embodiments, the presently disclosed subject matter provides an isolated immunoresponsive cell (a) comprising an antigen-recognizing receptor that binds to an antigen, and (b) expressing or secreting an IL-36 polypeptide. In certain embodiments, the immunoresponsive cell comprises an exogenous IL-36 polypeptide. In certain embodiments, the immunoresponsive cell comprises a nucleic acid encoding an IL-36 polypeptide. In certain embodiments, binding of the antigen-recognizing receptor to the antigen is capable of activating the immunoresponsive cell. In certain embodiments, the antigen-recognizing receptor is a CAR.

The presently disclosed subject matter further provides a composition comprising the immunoresponsive cells disclosed herein. In certain embodiments, the composition is a pharmaceutical composition that comprises a pharmaceutically acceptable excipient. In certain embodiments, the pharmaceutical composition is for treating and/or preventing a neoplasm (e.g., cancer), wherein the antigen to which the antigen-recognizing receptor binds is a tumor antigen.

The presently disclosed subject matter provides the immunoresponsive cells disclosed herein or the composition disclosed herein for use in a therapy, e.g., for use in reducing tumor burden, treating and/or preventing a neoplasm, lengthening survival of a subject having a neoplasm, and/or increasing immune-activating cytokine production in response to a tumor antigen or a pathogen antigen in a subject.

The presently disclosed subject matter also provides a method of treating and/or preventing a neoplasm in a subject. In certain embodiments, the method comprises administering to the subject an effective amount of the immunoresponsive cells or the pharmaceutical composition disclosed herein. The presently disclosed subject matter also provides a method of reducing tumor burden in a subject. In certain embodiments, the method comprises administering to the subject an effective amount of the immunoresponsive cells or the pharmaceutical composition disclosed herein. The presently disclosed subject matter further provides a method of lengthening survival of a subject having neoplasm (e.g., cancer). In certain embodiments, the method comprises administering to the subject an effective amount of the immunoresponsive cells or the pharmaceutical composition disclosed herein.

The presently disclosed subject matter also provides a method of enhancing or increasing an immune response to a target antigen in a subject. In certain embodiments, the method comprises administering to the subject an effective amount of the immunoresponsive cells or the pharmaceutical composition disclosed herein. The cell can express and secrete the IL-36 polypeptide that enhances the subject's immune response toward the target antigen.

The presently disclosed subject matter further provides a method of increasing immune-activating cytokine production in response to a tumor antigen or a pathogen antigen in a subject. In certain embodiments, the method comprises administering to the subject an effective amount of the immunoresponsive cells or the pharmaceutical composition disclosed herein. In certain non-limiting embodiments, the immune-activating cytokine is selected from the group consisting of IL-10, GM-SCF and IFN-γ. The presently disclosed subject matter further provides a method of treating blood cancer in a subject in need thereof. In certain embodiments, the method comprises administering to the subject a therapeutically effective amount of the immunoresponsive cells or the pharmaceutical composition disclosed herein. In certain embodiments, the cells are T cells. In certain embodiments, the antigen to which the antigen-recognizing receptor binds is CD19.

The presently disclosed subject matter further provides a method for producing an immunoresponsive cell disclosed herein. In certain embodiments, the method comprises introducing into an immunoresponsive cell (a) a first nucleic acid sequence that encodes an antigen-recognizing receptor that binds to an antigen, and (b) a second nucleic acid sequence that encodes an IL-36 polypeptide.

The presently disclosed subject matter further provides a nucleic acid composition comprising (a) a first nucleic acid sequence encoding an antigen-recognizing receptor (e.g., a CAR or TCR) that binds to an antigen and (b) a second nucleic acid sequence encoding an IL-36 polypeptide (mature or non-mature form of IL-36).

In certain non-limiting embodiments, the first or the second nucleic acid sequence is operably linked to a promoter element constitutively or inducibly expressed in the immunoresponsive cell. The promoter for the first nucleic acid sequence may be the same or different from the promoter for the second nucleic acid sequence. In certain non-limiting embodiments, each of the first and second nucleic acid sequences is operably linked to a promoter element constitutively or inducibly expressed in the immunoresponsive cell. One or both of the first and second nucleic acid sequences may be comprised in a vector, which may be the same vector (bicistronic) or separate vectors. In certain non-limiting embodiments, the vector is a virus vector, e.g., a retroviral vector.

In certain embodiments, the nucleic acid composition is comprised in a vector. In certain non-limiting embodiments, the vector is a virus vector, e.g., a retroviral vector. The presently disclosed subject matter also provides a vector comprising the nucleic acid composition disclosed herein.

The presently disclosed subject matter provides a kit for inducing and/or enhancing an immune response and/or treating and/or preventing a neoplasm (e.g., cancer) or, pathogen infection.

In certain embodiments, the kit comprises the immunoresponsive cells disclosed herein, the pharmaceutical composition disclosed herein, the nucleic acid composition disclosed herein, or the vector disclosed herein. In certain embodiments, the kit further comprises written instructions for inducing and/or enhancing an immune response and/or treating and/or preventing a neoplasm or a pathogen infection.

In various non-limiting embodiments, the immunoresponsive cell is autologous to its intended recipient subject.

In various embodiments of any of the aspects delineated herein, the antigen-recognizing receptor is a TCR or a CAR. In various embodiments of any of the aspects delineated herein, the antigen-recognizing receptor is exogenous or endogenous. In various embodiments of any of the aspects delineated herein, the antigen-recognizing receptor is recombinantly expressed. In various embodiments of any of the aspects delineated herein, the antigen-recognizing receptor is expressed from a vector. In various embodiments of any of the aspects delineated herein, the antigen-recognizing receptor is a CAR. In certain embodiments, the CAR comprises an extracellular antigen-binding domain, a transmembrane domain, and an intracellular signaling domain. In certain embodiments, wherein the CAR does not comprise a co-stimulatory signaling domain. In certain embodiments, the CAR is 19z.

In various embodiments of any of the aspects delineated herein, the antigen-recognizing receptor is a TCR. In certain embodiments, the TCR is a recombinant TCR. In certain embodiments, the TCR is a non-naturally occurring TCR. In certain embodiments, the TCR differs from any naturally occurring TCR by at least one amino acid residue. In certain embodiments, the TCR is modified from a naturally occurring TCR by at least one amino acid residue.

In various embodiments of any of the aspects delineated herein, the antigen to which the antigen-recognizing receptor binds is a tumor antigen or a pathogen antigen. In certain embodiments, the antigen is a tumor antigen. In various embodiments of any of the aspects delineated herein, the tumor antigen is selected from the group consisting of CD19, MUC16, MUC1, CA1X, CEA, CD8, CD7, CD10, CD20, CD22, CD30, CD33, CLL1 CD34, CD38, CD41, CD44, CD49f, CD56, CD74, CD133, CD138, a cytomegalovirus (CMV) infected cell antigen, EGP-2, EGP-40, EpCAM, erb-B2,3,4, FBP, Fetal acetylcholine receptor, folate receptor-α, GD2, GD3, HER-2, hTERT, IL-13R-a2, κ-light chain, KDR, LeY, L1 cell adhesion molecule, MAGE-A1, Mesothelin, ERBB2, MAGEA3, p53, MART1, GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD123, CD44V6, NKCS1, EGF1R, EGFR-VIII, CD99, CD70, ADGRE2, CCR1, LILRB2, PRAME, and ERBB. In certain embodiments, the antigen is CD19. Amino acid sequences that specifically bind to said antigens are known in the art or may be prepared using methods known in the art; examples include immunoglobulins, variable regions of immunoglobulins (e.g. variable fragment ("Fv") or bivalent variable fragment ("Fab")), single chain antibodies, etc. In certain embodiments, the antigen is a pathogen antigen.

In various non-limiting embodiments of any of the aspects delineated herein, the exogenous IL-36 polypeptide is secreted. In various non-limiting embodiments of any of the aspects delineated herein, the IL-36 polypeptide is comprised (and expressed) from a vector. In various non-limiting embodiments of any of the aspects delineated herein, the IL-36 polypeptide comprises a heterologous signal sequence at the amino-terminus (e.g., a signal sequence that is not naturally associated with IL-36). In various embodiments of any of the aspects delineated herein, the heterologous signal sequence is selected from the group consisting of IL-2 signal sequence, the kappa leader sequence, the CD8 leader sequence, and combinations and/or synthetic variations thereof which retain the capacity to promote secretion of IL-36 polypeptide (either mature or non-mature). In certain embodiments, the IL-36 peptide is a mature form of IL-36 alpha, IL-36 beta, IL-36 gamma, or a functional fragment thereof. In certain embodiments, the IL-36 peptide comprises an amino acid sequence that is at least about 80% homologous to the sequence set forth in SEQ ID NO: 4, SEQ ID NO: 20, SEQ ID NO: 21, SEQ ID NO: 30, SEQ ID NO: 31, or SEQ ID NO: 32. In certain embodiments, wherein the IL-36 peptide comprises the amino acid sequence set forth in SEQ ID NO: 4, SEQ ID NO: 20, SEQ ID NO: 21, SEQ ID NO: 30, SEQ ID NO: 31, or SEQ ID NO: 32. In various embodiments of any of the aspects delineated herein, the IL-36 polypeptide enhances an immune response of the immunoresponsive cell. In certain embodiments, the exogenous IL-36 polypeptide increases anti-tumor cytokine production. In certain embodiments, the anti-tumor cytokine is selected from the group consisting of IL-10, GM-CSF and IFN-γ.

In various embodiments of any of the aspects delineated herein, the method reduces the number of tumor cells, reduces tumor size, eradicates the tumor in the subject, reduces the tumor burden in the subject, eradicates the tumor burden in the subject, increases the period of time to relapse/recurrence, and/or increases the period of survival.

Illustrative neoplasms for which the presently disclosed subject matter can be used include, but are not limited to leukemias (e.g., acute leukemia, acute lymphocytic leukemia, acute myelocytic leukemia a, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In various non-limiting embodiments of any of the aspects delineated herein, the neoplasm is one or more of blood cancer, B cell leukemia, multiple myeloma, lymphoblastic leukemia (ALL), chronic lymphocytic leukemia, non-Hodgkin's lymphoma, and ovarian cancer. In certain embodiments, the blood cancer is one or more of B cell leukemia, multiple myeloma, acute lymphoblastic leukemia (ALL), chronic lymphocytic leukemia, and non-Hodgkin's lymphoma. In certain embodiments, the antigen is CD19. In certain embodiments, the neoplasm is ovarian cancer, and the antigen is MUC16.

BRIEF DESCRIPTION OF THE FIGURES

The following Detailed Description, given by way of example, but not intended to limit the presently disclosed subject matter to specific embodiments described, may be understood in conjunction with the accompanying drawings.

DETAILED DESCRIPTION OF THE INVENTION

Figure 1A:
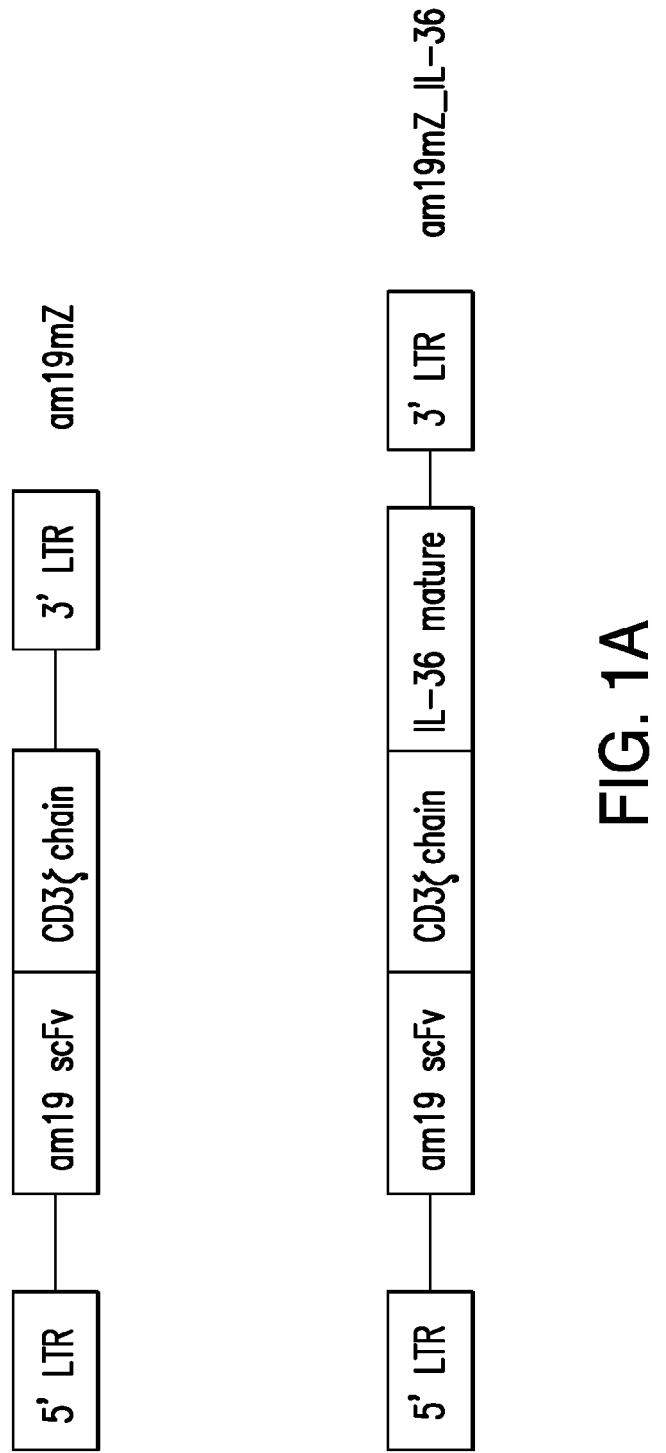
FIGS. 1A-1D depict representations of various CAR constructs. A) Schematic representation of am19mZ (a first generation CAR comprising a rat anti-mouse CD19 scFv and an intracellular signaling domain that comprises a mouse CD3ζ polypeptide. The amino acid sequence and corresponding nucleotide sequence for am19mZ are set forth in SEQ ID NOS: 5 and 65, respectively); and ah19mZ_IL-36 (a first generation CAR (am19mZ) secreting murine IL-36. Both CARs utilized a CD28 proximal extracellular and transmembrane domain as a hinge. In all murine CAR constructs, the cytokine was separated from the CAR by a self-cleaving P2A element. B) first-generation anti-mouse CD 19 myc-tag CAR incorporating constitutively-secreted murine IL36-alpha. C) first-generation anti-mouse CD 19 myc-tag CAR incorporating constitutively-secreted murine IL36-beta. D) first-generation anti-mouse CD 19 myc-tag CAR incorporating constitutively-secreted murine IL36-gamma. All vectors comprised SFG backbone.

The presently disclosed subject matter provides cells, including genetically modified immunoresponsive cells (e.g., T cells, NK cells, or CTL cells) comprising a combination of an antigen-recognizing receptor (e.g., TCR or CAR) and a secretable IL-36 polypeptide (e.g., an exogenous IL-36 polypeptide, or a nucleic acid encoding an IL-36 polypeptide). The presently disclosed subject matter also provides methods of using such cells for inducing and/or enhancing an immune response to a target antigen, and/or treating and/or preventing neoplasia or other diseases/disorders where an increase in an antigen-specific immune response is desired. The presently disclosed subject matter is based, at least in part, on the discovery that a secretable IL-36 polypeptide enhances the anti-tumor effect of an immunoresponsive cell comprising an antigen-recognizing receptor (e.g., a CAR-expressing T cell or a TCR-expressing T cell). It was observed that the co-expression of an IL-36 polypeptide and an antigen-recognizing receptor (e.g., a CAR, such as 19z CAR) on T cells led to increased cytokine secretion.

Malignant cells have developed a series of mechanisms to protect themselves from immune recognition and elimination. The presently disclosed subject matter provides immunogenicity within the tumor microenvironment for tumor eradication, and represents a significant advance over conventional adoptive T cell therapy. The presently disclosed subject matter provides an option of foregoing some or all ancillary treatments such as prior conditioning of the host with total body irradiation, high-dose chemotherapy, and/or post-infusion cytokine support.

1. Definitions

Unless defined otherwise, all technical and scientific terms used herein have the meaning commonly understood by a person skilled in the art. The following references provide one of skill with a general definition of many of the terms used in the presently disclosed subject matter: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold or within 2-fold, of a value.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds to an antigen, a formation of an immunological synapse occurs that includes clustering of many molecules near the bound receptor (e.g. CD4 or CD8, CD3γ/δ/ε/ζ, etc.). This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response.

By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), OX40, CD40 and ICOS. Receiving multiple stimulatory signals can be important to mount a robust and long-term T cell mediated immune response. T cells can quickly become inhibited and unresponsive to antigen. While the effects of these co-stimulatory signals may vary, they generally result in increased gene expression in order to generate long lived, proliferative, and anti-apoptotic T cells that robustly respond to antigen for complete and sustained eradication.

The term "antigen-recognizing receptor" as used herein refers to a receptor that is capable of activating an immune or immunoresponsive cell (e.g., a T-cell) in response to its binding to an antigen. Non-limiting examples of antigen-recognizing receptors include native or endogenous T cell receptors ("TCRs"), and chimeric antigen receptors ("CARs").

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fe fragment of intact antibody, clear more rapidly from the circulation, and may have less non-specific tissue binding of an intact antibody (Wahl et al., *J. Nucl. Med.* 24:316-325 (1983). As used herein, antibodies include whole native antibodies, bispecific antibodies; chimeric antibodies; Fab, Fab', single chain V region fragments (scFv), fusion polypeptides, and unconventional antibodies. In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant (CH) region. The heavy chain constant region is comprised of three domains, CHL CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. (1991) Sequences of Proteins of Immunological Interest, Fifth Edition, U.S. Department of Health and Human Services, NIH Publication No. 91-3242).

As used herein, the term "single-chain variable fragment" or "scFv" is a fusion protein of the variable regions of the heavy ($V_H$) and light chains ($V_L$) of an immunoglobulin covalently linked to form a $V_H$::$V_L$ heterodimer. The $V_H$ and $V_L$ are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imuno12009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chern 2003 25278(38):36740-7; Xie et al., Nat Biotech 1997 15(8):768-71; Ledbetter et al., Crit Rev Immuno11997 17(5-6):427-55; Ho et al., BioChim Biophys Acta 2003 1638(3): 257-66).

As used herein, the term "affinity" is meant a measure of binding strength. Affinity can depend on the closeness of stereochemical fit between antibody combining sites and antigen determinants, on the size of the area of contact between them, and/or on the distribution of charged and hydrophobic groups. As used herein, the term "affinity" also includes "avidity", which refers to the strength of the antigen-antibody bond after formation of reversible complexes. Methods for calculating the affinity of an antibody for an antigen are known in the art, including, but not limited to, various antigen-binding experiments, e.g., functional assays (e.g., flow cytometry assay).

The term "chimeric antigen receptor" or "CAR" as used herein refers to a molecule comprising an extracellular antigen-binding domain that is fused to an intracellular signaling domain that is capable of activating or stimulating an immunoresponsive cell, and a transmembrane domain. In certain embodiments, the extracellular antigen-binding domain of a CAR comprises a scFv. The scFv can be derived from fusing the variable heavy and light regions of an antibody. Alternatively or additionally, the scFv may be derived from Fab's (instead of from an antibody, e.g., obtained from Fab libraries). In certain embodiments, the scFv is fused to the transmembrane domain and then to the intracellular signaling domain. In certain embodiments, the CAR is selected to have high binding affinity or avidity for the antigen.

As used herein, the term "nucleic acid molecules" include any nucleic acid molecule that encodes a polypeptide of interest (e.g., an IL-36 polypeptide) or a fragment thereof. Such nucleic acid molecules need not be 100% homologous or identical with an endogenous nucleic acid sequence, but may exhibit substantial identity. Polynucleotides having "substantial identity" or "substantial homology" to an endogenous sequence are typically capable of hybridizing with at least one strand of a double-stranded nucleic acid molecule. By "hybridize" is meant a pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration will ordinarily be less than about 750 mM NaCl and 75 mM trisodium citrate, e.g., less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, e.g., at least about 50% formamide. Stringent temperature conditions will ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In certain embodiments, hybridization will occur at 30° C. in 750 mM NaCl, 75 mM trisodium citrate, and 1% SDS. In certain embodiments, hybridization will occur at 37° C. in 500 mM NaCl, 50 mM trisodium citrate, 1% SDS, 35% formamide, and 100 μg/ml denatured salmon sperm DNA (ssDNA). In certain embodiments, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, e.g., less than about 15 mM NaCl and 1.5 mM trisodium citrate. Stringent temperature conditions for the wash steps will ordinarily include a temperature of at least about 25° C., of at least about 42° C., or of at least about 68° C. In certain embodiments, wash steps will occur at 25° C. in 30 mM NaCl, 3 mM trisodium citrate, and 0.1% SDS. In certain embodiments, wash steps will occur at 42° C. in 15 mM NaCl, 1.5 mM trisodium citrate, and 0.1% SDS. In certain embodiments, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" or "substantially homologous" is meant a polypeptide or nucleic acid molecule exhibiting at least about 50% homologous or identical to a reference amino acid sequence (for example, any one of the amino acid sequences described herein) or nucleic acid sequence (for example, any one of the nucleic acid sequences described herein). In certain embodiments, such a sequence is at least about 60%, at least about 65%, at least about 70%, at least about 75%, at least about 80%, at least about 85%, at least about 90%, at least about 95%, at least about 99%, or at least about 100% homologous or identical to the sequence of the amino acid or nucleic acid used for comparison.

Sequence identity can be measured by using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "analog" is meant a structurally related polypeptide or nucleic acid molecule having the function of a reference polypeptide or nucleic acid molecule.

The term "ligand" as used herein refers to a molecule that binds to a receptor. In certain embodiments, the ligand binds to a receptor on another cell, allowing for cell-to-cell recognition and/or interaction.

The term "constitutive expression" or "constitutively expressed" as used herein refers to expression or expressed under all physiological conditions.

By "disease" is meant any condition, disease or disorder that damages or interferes with the normal function of a cell, tissue, or organ, e.g., neoplasia, and pathogen infection of cell.

By "effective amount" is meant an amount sufficient to have a therapeutic effect. In certain embodiments, an "effective amount" is an amount sufficient to arrest, ameliorate, or inhibit the continued proliferation, growth, or metastasis (e.g., invasion, or migration) of a neoplasm.

By "enforcing tolerance" is meant preventing the activity of self-reactive cells or immunoresponsive cells that target transplanted organs or tissues.

By "endogenous" is meant a nucleic acid molecule or polypeptide that is normally expressed in a cell or tissue.

By "exogenous" is meant a nucleic acid molecule or polypeptide that is not endogenously present in a cell. The term "exogenous" would therefore encompass any recombinant nucleic acid molecule or polypeptide expressed in a cell, such as foreign, heterologous, and over-expressed nucleic acid molecules and polypeptides. By "exogenous" nucleic acid is meant a nucleic acid not present in a native wild-type cell; for example, an exogenous nucleic acid may vary from an endogenous counterpart by sequence, by position/location, or both. For clarity, an exogenous nucleic acid may have the same or different sequence relative to its native endogenous counterpart; it may be introduced by genetic engineering into the cell itself or a progenitor thereof, and may optionally be linked to alternative control sequences, such as a non-native promoter or secretory sequence.

By a "heterologous nucleic acid molecule or polypeptide" is meant a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

By "immunoresponsive cell" is meant a cell that functions in an immune response or a progenitor, or progeny thereof.

By "modulate" is meant positively or negatively alter. Exemplary modulations include a about 1%, about 2%, about 5%, about 10%, about 25%, about 50%, about 75%, or about 100% change.

By "increase" is meant to alter positively by at least about 5%. An alteration may be by about 5%, about 10%, about 25%, about 30%, about 50%, about 75%, about 100% or more.

By "reduce" is meant to alter negatively by at least about 5%. An alteration may be by about 5%, about 10%, about 25%, about 30%, about 50%, about 75%, or even by about 100%.

By "isolated cell" is meant a cell that is separated from the molecular and/or cellular components that naturally accompany the cell.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

The term "antigen-binding domain" as used herein refers to a domain capable of specifically binding a particular antigenic determinant or set of antigenic determinants present on a cell.

"Linker", as used herein, shall mean a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In certain embodiments, the linker comprises a sequence set forth in GGGGSGGGGSGGGGS [SEQ ID NO: 23].

By "neoplasm" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasia can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasia include cancers, such as sarcomas, carcinomas, or plasmacytomas (malignant tumor of the plasma cells).

By "receptor" is meant a polypeptide, or portion thereof, present on a cell membrane that selectively binds one or more ligand.

By "recognize" is meant selectively binds to a target. A T cell that recognizes a tumor can expresses a receptor (e.g., a TCR or CAR) that binds to a tumor antigen.

By "reference" or "control" is meant a standard of comparison. For example, the level of scFv-antigen binding by a cell expressing a CAR and an scFv may be compared to the level of scFv-antigen binding in a corresponding cell expressing CAR alone.

By "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

By "signal sequence" or "leader sequence" is meant a peptide sequence (e.g., 5, 10, 15, 20, 25 or 30 amino acids) present at the N-terminus of newly synthesized proteins that directs their entry to the secretory pathway. Exemplary leader sequences include, but is not limited to, the IL-2 signal sequence: MYRMQLLSCIALSLALVTNS [SEQ ID NO: 8] (human), MYSMQLASCVTLTLVLLVNS [SEQ ID NO: 24] (mouse); the kappa leader sequence: METPAQLLFLLLLWLPDTTG [SEQ ID NO: 25] (human), METDTLLLWVLLLWVPGSTG [SEQ ID NO: 26] (mouse); the CD8 leader sequence: MALPVTALLLPLALLLHAARP [SEQ ID NO: 27] (human); the truncated human CD8 signal peptide: MALPVTALLLPLALLLHA [SEQ ID NO: 80] (human); the albumin signal sequence: MKWVTFISLLFSSAYS [SEQ ID NO: 28] (human); and the prolactin signal sequence: MDSKGSSQKGSRLLLLLVVSNLLLCQGVVS [SEQ ID NO: 29] (human). By "soluble" is meant a polypeptide that is freely diffusible in an aqueous environment (e.g., not membrane bound).

By "specifically binds" is meant a polypeptide or fragment thereof that recognizes and binds to a biological molecule of interest (e.g., a polypeptide), but which does not substantially recognize and bind other molecules in a sample, for example, a biological sample, which naturally includes a presently disclosed polypeptide.

The term "tumor antigen" as used herein refers to an antigen (e.g., a polypeptide) that is uniquely or differentially expressed on a tumor cell compared to a normal or non-IS neoplastic cell. In certain embodiments, a tumor antigen includes any polypeptide expressed by a tumor that is capable of activating or inducing an immune response via an antigen recognizing receptor (e.g., CD19, MUC-16) or capable of suppressing an immune response via receptor-ligand binding (e.g., CD47, PD-L1/L2, B7.1/2).

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys. The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

Other aspects of the presently disclosed subject matter are described in the following disclosure and are within the ambit of the presently disclosed subject matter.

2. Antigen-Recognizing Receptors

The present disclosure provides antigen-recognizing receptors that bind to an antigen of interest. In certain embodiments, the antigen-recognizing receptor is a chimeric antigen receptor (CAR). In certain embodiments, the antigen-recognizing receptor is a T-cell receptor (TCR). The antigen-recognizing receptor can bind to a tumor antigen or a pathogen antigen.

2.1. Antigens

In certain embodiments, the antigen-recognizing receptor binds to a tumor antigen. Any tumor antigen (antigenic peptide) can be used in the tumor-related embodiments described herein. Sources of antigen include, but are not limited to, cancer proteins. The antigen can be expressed as a peptide or as an intact protein or portion thereof. The intact protein or a portion thereof can be native or mutagenized. Non-limiting examples of tumor antigens include carbonic anhydrase IX (CAIX), carcinoembryonic antigen (CEA), CD8, CD7, CD10, CD19, CD20, CD22, CD30, CD33, CLL1, CD34, CD38, CD41, CD44, CD49f, CD56, CD74, CD133, CD138, CD123, CD44V6, an antigen of a cytomegalovirus (CMV) infected cell (e.g., a cell surface antigen), epithelial glycoprotein-2 (EGP-2), epithelial glycoprotein-40 (EGP-40), epithelial cell adhesion molecule (EpCAM), receptor tyrosine-protein kinases Erb-B2, Erb-B3, Erb-B4, folate-binding protein (FBP), fetal acetylcholine receptor (AChR), folate receptor-α, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Ra2), κ-light chain, kinase insert domain receptor (KDR), Lewis Y (LeY), L1 cell adhesion molecule (L1CAM), melanoma antigen family A, 1 (MAGE-A1), Mucin 16 (MUC16), Mucin 1 (MUC1), Mesothelin (MSLN), ERBB2, MAGEA3, p53, MART1, GP100, Proteinase3 (PR1), Tyrosinase, Survivin, hTERT, EphA2, NKG2D ligands, cancer-testis antigen NY-ESO-1, oncofetal antigen (h5T4), prostate stem cell antigen (PSCA), prostate-specific membrane antigen (PSMA), ROR1, tumor-associated glycoprotein 72 (TAG-72), vascular endothelial growth factor R2 (VEGF-R2), Wilms tumor protein (WT-1), BCMA, NKCS1, EGF1R, EGFR-VIII, CD99, CD70, ADGRE2, CCR1, LILRB2, and PRAME.

In certain embodiments, the antigen-recognizing receptor binds to CD19. In certain embodiments, the antigen-recognizing receptor binds to a murine CD19 polypeptide. In certain embodiments, the murine CD19 polypeptide comprises the amino acid sequence set forth in SEQ ID NO: 61.

[SEQ ID NO: 61]
RPQKSLLVEVEEGGNVVLPCLPDSSPVSSEKLAWYRGNQSTPFLELSPGS

PGLGLHVGSLGILLVIVNVSDHMGGFYLCQKRPPFKDIWQPAWTVNVEDS

GEMFRWNASDVRDLDCDLRNRSSGSHRSTSGSQLYVWAKDHPKVWGTKPV

CAPRGSSLNQSLINQDLTVAPGSTLWLSCGVPPVPVAKGSISWTHVHPRR

PNVSLLSLSLGGEHPVREMWVWGSLLLLPQATALDEGTYYCLRGNLTIER

HVKVIARSAVWLWLLRTGG

In certain embodiments, the antigen-recognizing receptor binds to a human CD19 polypeptide. In certain embodiments, the human CD19 polypeptide comprises the amino acid sequence set forth in SEQ ID NO: 62.

[SEQ ID NO: 62]
PEEPLVVKVEEGDNAVLQCLKGTSDGPTQQLTWSRESPLKPFLKLSLGLP

GLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEG

EPPCLPPRDSLNQSLSQDLTMAPGSTLWLSCGVPPDSVSRGPLSWTHVHP

KGPKSLLSLELKDDRPARDMWVMETGLLLPRATAQDAGKYYCHRGNLTMS

FHLEITARPVLWHWLLRTGGWK

In certain embodiments, the antigen-recognizing receptor binds to the extracellular domain of a human or murine CD19 protein.

In certain embodiments, the antigen-recognizing receptor binds to a pathogen antigen, e.g., for use in treating and/or preventing a pathogen infection or other infectious disease, for example, in an immunocompromised subject. Non-limiting examples of pathogen includes a virus, bacteria, fungi, parasite and protozoa capable of causing disease.

Non-limiting examples of viruses include, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Cox-sackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Naira viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Non-limiting examples of bacteria include *Pasteurella, Staphylococci, Streptococcus, Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus (viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtherias, corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Rickettsia*, and *Actinomyces israelli*.

In certain embodiments, the pathogen antigen is a viral antigen present in Cytomegalovirus (CMV), a viral antigen present in Epstein Barr Virus (EBV), a viral antigen present in Human Immunodeficiency Virus (HIV), or a viral antigen present in influenza virus.

2.2. T-Cell Receptor (TCR)

In certain embodiments, the antigen-recognizing receptor is a TCR. A TCR is a disulfide-linked heterodimeric protein consisting of two variable chains expressed as part of a complex with the invariant CD3 chain molecules. A TCR is found on the surface of T cells, and is responsible for recognizing antigens as peptides bound to major histocompatibility complex (MHC) molecules. In certain embodiments, a TCR comprises an alpha chain and a beta chain (encoded by TRA and TRB, respectively). In certain embodiments, a TCR comprises a gamma chain and a delta chain (encoded by TRG and TRD, respectively).

Each chain of a TCR is composed of two extracellular domains: Variable (V) region and a Constant (C) region. The Constant region is proximal to the cell membrane, followed by a transmembrane region and a short cytoplasmic tail. The Variable region binds to the peptide/MHC complex. The variable domain of both chains each has three complementarity determining regions (CDRs).

In certain embodiments, a TCR can form a receptor complex with three dimeric signaling modules CD3δ/ε, CD3γ/ε and CD247 ζ/ζ or ζ/η. When a TCR complex engages with its antigen and MHC (peptide/MHC), the T cell expressing the TCR complex is activated.

In certain embodiments, the antigen-recognizing receptor is a recombinant TCR. In certain embodiments, the antigen-recognizing receptor is a non-naturally occurring TCR. In certain embodiments, the non-naturally occurring TCR differs from any naturally occurring TCR by at least one amino acid residue. In certain embodiments, the non-naturally occurring TCR differs from any naturally occurring TCR by at least about 2, about 3, about 4, about 5, about 6, about 7, about 8, about 9, about 10, about 11, about 12, about 13, about 14, about 15, about 20, about 25, about 30, about 40, about 50, about 60, about 70, about 80, about 90, about 100 or more amino acid residues. In certain embodiments, the non-naturally occurring TCR is modified from a naturally occurring TCR by at least one amino acid residue. In certain embodiments, the non-naturally occurring TCR is modified from a naturally occurring TCR by at least about 2, about 3, about 4, about 5, about 6, about 7, about 8, about 9, about 10, about 11, about 12, about 13, about 14, about 15, about 20, about 25, about 30, about 40, about 50, about 60, about 70, about 80, about 90, about 100 or more amino acid residues.

2.3. Chimeric Antigen Receptor (CAR)

In certain embodiments, the antigen-recognizing receptor is a CAR. CARs are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen-binding domain (e.g., a scFv), which is fused to a transmembrane domain, which is fused to cytoplasmic/intracellular signaling domain. "First generation" CARs can provide de novo antigen recognition and cause activation of both $CD4^+$ and $CD8^+$ T cells through their CD3ζ chain signaling domain in a single fusion molecule, independent of HLA-mediated antigen presentation. "Second generation" CARs add intracellular signaling domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3). "Third generation" CARs comprise those that provide multiple co-stimulation (e.g., CD28 and 4-1BB) and activation (CD3). In certain embodiments, the antigen-recognizing receptor is a first generation CAR. In certain embodiments, the antigen-recognizing receptor is a second generation CAR.

In certain non-limiting embodiments, the extracellular antigen-binding domain of the CAR (embodied, for example, an scFv or an analog thereof) binds to an antigen with a dissociation constant ($K_d$) of about $2 \times 10^{-7}$ M or less. In certain embodiments, the $K_d$ is about $2 \times 10^{-7}$ M or less, about $1 \times 10^{-7}$ M or less, about $9 \times 10^{-8}$ M or less, about $1 \times 10^{-8}$ M or less, about $9 \times 10^{-9}$ M or less, about $5 \times 10^{-9}$ M or less, about $4 \times 10^{-9}$ M or less, about $3 \times 10^{-9}$ or less, about $2 \times 10^{-9}$ M or less, or about $1 \times 10^{-9}$ M or less. In certain non-limiting embodiments, the $K_d$ is about $3 \times 10^{-9}$ M or less. In certain non-limiting embodiments, the $K_d$ is from about $1 \times 10^{-9}$ M to about $3 \times 10^{-7}$ M. In certain non-limiting embodiments, the $K_d$ is from about $1.5 \times 10^{-9}$ M to about $3 \times 10^{-7}$ M. In certain non-limiting embodiments, the $K_d$ is from about $1.5 \times 10^{-9}$ M to about $2.7 \times 10^{-7}$ M.

Binding of the extracellular antigen-binding domain (for example, in an scFv or an analog thereof) can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or an scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the extracellular antigen-binding domain of the CAR is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet).

In accordance with the presently disclosed subject matter, a CARs can comprise an extracellular antigen-binding domain, a transmembrane domain and an intracellular signaling domain, wherein the extracellular antigen-binding domain specifically binds to an antigen, e.g., a tumor antigen or a pathogen antigen.

In certain embodiments, the extracellular antigen-binding domain of a presently disclosed CAR is a murine scFv. In certain embodiments, the extracellular antigen-binding domain of a presently disclosed CAR is a murine scFv that binds to a murine CD19 polypeptide. In certain embodiments, the extracellular antigen-binding domain is a murine scFv, which comprises the amino acid sequence of SEQ ID NO: 59 and specifically binds to a murine CD19 polypeptide (e.g., a murine CD19 polypeptide comprising the amino acid sequence set forth in SEQ ID NO: 61). In certain embodiments, the nucleotide sequence encoding the amino acid sequence of SEQ ID NO: 59 is set forth in SEQ ID NO: 60. In certain embodiments, the murine scFv comprises a heavy chain variable region ($V_H$) comprising the amino acid sequence set forth in SEQ ID NO: 49. In certain embodiments, the murine scFv comprises a light chain variable region ($V_L$) comprising the amino acid sequence set forth in SEQ ID NO: 50. In certain embodiments, the murine scFv comprises a $V_H$ comprising the amino acid sequence set forth in SEQ ID NO: 49 and a $V_L$ comprising the amino acid sequence set forth in SEQ ID NO: 50, optionally with (iii) a linker sequence, for example a linker peptide, between the $V_H$ and the $V_L$. In certain embodiments, the linker comprises amino acids having the sequence set forth in SEQ ID NO: 23. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 49. For example, the extracellular antigen-binding domain comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 49. In certain embodiments, the extracellular antigen-binding domain comprises a $V_H$ comprising the amino acid sequence set forth in SEQ ID NO: 49. In certain embodiments, the extracellular antigen-binding domain comprises a $V_L$ comprising an amino acid sequence that is at least about 80% (e.g., at least about 85%, at least about 90%, or at least about 95%) homologous to SEQ ID NO: 50. For example, the extracellular antigen-binding domain comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 50. In certain embodiments, the extracellular antigen-binding domain comprises a $V_L$ comprising the amino acid sequence set forth in SEQ ID NO: 50. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 49, and a $V_L$ comprising an amino acid sequence that is at least about 80% (e.g., at least about 85%, at least about 90%, or at least about 95%) homologous to SEQ ID NO: 50. In certain embodiments, the extracellular antigen-binding domain comprises a $V_H$ comprising the amino acid sequence set forth in SEQ ID NO: 49 and a $V_L$ comprising the amino acid sequence set forth in SEQ ID NO: 50. In certain embodiments, the extracellular antigen-binding domain comprises a $V_H$ CDR1 comprising the amino acid sequence set forth in SEQ ID NO: 43, or a conservative modification thereof, a $V_H$ CDR2 comprising the amino acid sequence set forth in SEQ ID NO: 44 or a conservative modification thereof, and a $V_H$ CDR3 comprising the amino acid sequence set forth in SEQ ID NO: 45, a conservative modification thereof. In certain embodiments, the extracellular antigen-binding domain comprises a $V_H$ CDR1 comprising the amino acid sequence set forth in SEQ ID NO: 43, a $V_H$ CDR2 comprising the amino acid sequence set forth in SEQ ID NO: 44, and a $V_H$ CDR3 comprising the amino acid sequence set forth in SEQ ID NO: 45. In certain embodiments, the extracellular antigen-binding domain comprises a $V_L$ CDR1 comprising the amino acid sequence set forth in SEQ ID NO: 46 or a conservative modification thereof, a $V_L$ CDR2 comprising the amino acid sequence set forth in SEQ ID NO: 47 or a conservative modification thereof, and a $V_L$ CDR3 comprising the amino acid sequence set forth in SEQ ID NO: 48 or a conservative modification thereof. In certain embodiments, the extracellular antigen-binding domain comprises a $V_L$ CDR1 comprising the amino acid sequence set forth in SEQ ID NO: 46, a $V_L$ CDR2 comprising the amino acid sequence set forth in SEQ ID NO: 47, and a $V_L$ CDR3 comprising the amino acid sequence set forth in SEQ ID NO: 48. In certain embodiments, the extracellular antigen-binding domain comprises a $V_H$ CDR1 comprising the amino acid sequence set forth in SEQ ID NO: 43 or a conservative modification thereof, a $V_H$ CDR2 comprising the amino acid sequence set forth in SEQ ID NO: 44 or a conservative modification thereof, a $V_H$ CDR3 comprising the amino acid sequence set forth in SEQ ID NO: 45, a conservative modification thereof, a $V_L$ CDR1 comprising the amino acid sequence set forth in SEQ ID NO: 46 or a conservative modification thereof, a $V_L$ CDR2 comprising the amino acid sequence set forth in SEQ ID NO: 47 or a conservative modification thereof, and a $V_L$ CDR3 comprising the amino acid sequence set forth in SEQ ID NO: 48 or a conservative modification thereof. In certain embodiments, the extracellular antigen-binding domain comprises a $V_H$ CDR1 comprising amino acids having the sequence set forth in SEQ ID NO: 43, a $V_H$ CDR2 comprising the amino acid sequence set forth in SEQ ID NO: 44, a $V_H$ CDR3 comprising the amino acid sequence set forth in SEQ ID NO: 45, a $V_L$ CDR1 comprising the amino acid sequence set forth in SEQ ID NO: 46, a $V_L$ CDR2 comprising the amino acid sequence set forth in SEQ ID NO: 47, and a $V_L$ CDR3 comprising the amino acid sequence set forth in SEQ ID NO: 48.

In certain embodiments, the extracellular antigen-binding domain of a presently disclosed CAR is a murine scFv that binds to a human CD19 polypeptide. In certain embodiments, the extracellular antigen-binding domain is a murine scFv, which comprises the amino acid sequence of SEQ ID NO: 63 and specifically binds to a human CD19 polypeptide (e.g., a human CD19 polypeptide comprising the amino acid sequence set forth in SEQ ID NO: 62). In certain embodiments, the nucleotide sequence encoding the amino acid sequence of SEQ ID NO: 63 is set forth in SEQ ID NO: 64. In certain embodiments, the murine scFv comprises a heavy chain variable region ($V_H$) comprising the amino acid sequence set forth in SEQ ID NO: 57. In certain embodiments, the murine scFV comprises a light chain variable region ($V_L$) comprising the amino acid sequence set forth in SEQ ID NO: 58. In certain embodiments, the murine scFv comprises $V_H$ comprising the amino acid sequence set forth in SEQ ID NO: 57 and a $V_L$ comprising the amino acid sequence set forth in SEQ ID NO: 58, optionally with (iii) a linker sequence, for example a linker peptide, between the $V_H$ and the $V_L$. In certain embodiments, the linker comprises amino acids having the sequence set forth in SEQ ID NO: 23. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 57. For example, the extracellular antigen-binding domain comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 57. In certain embodiments, the extracellular antigen-binding domain comprises a $V_H$ comprising the amino sequence set forth in SEQ ID NO: 57. In certain embodiments, the extracellular antigen-binding domain comprises a $V_L$ comprising an amino acid sequence that is at least about 80% (e.g., at least about 85%, at least about 90%, or at least about 95%) homologous to SEQ ID NO: 58. For example, the extracellular antigen-binding domain comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 58. In certain embodiments, the extracellular antigen-binding domain comprises a $V_L$ comprising the amino acid sequence set forth in SEQ ID NO: 58. certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 57, and a $V_L$ comprising an amino acid sequence that is at least about 80% (e.g., at least about 85%, at least about 90%, or at least about 95%) homologous to SEQ ID NO: 58. In certain embodiments, the extracellular antigen-binding domain comprises a $V_H$ comprising the amino acid sequence set forth in SEQ ID NO: 57 and a $V_L$ comprising the amino acid sequence set forth in SEQ ID NO: 58. In certain embodiments, the extracellular antigen-binding domain comprises a $V_H$ CDR1 comprising the amino acid sequence set forth in SEQ ID NO: 51, or a conservative modification thereof, a $V_H$ CDR2 comprising the amino acid sequence set forth in SEQ ID NO: 52 or a conservative modification thereof, and a $V_H$ CDR3 comprising the amino acid sequence set forth in SEQ ID NO: 53, a conservative modification thereof. In certain embodiments, the extracellular antigen-binding domain comprises a $V_H$ CDR1 comprising the amino acid sequence set forth in SEQ ID NO: 51, a $V_H$ CDR2 comprising the amino acid sequence set forth in SEQ ID NO: 52, and a $V_H$ CDR3 comprising the amino acid sequence set forth in SEQ ID NO: 53. In certain embodiments, the extracellular antigen-binding domain comprises a $V_L$ CDR1 comprising the amino acid sequence set forth in SEQ ID NO: 54 or a conservative modification thereof, a $V_L$ CDR2 comprising the amino acid sequence set forth in SEQ ID NO: 55 or a conservative modification thereof, and a $V_L$ CDR3 comprising the amino acid sequence set forth in SEQ ID NO: 56 or a conservative modification thereof. In certain embodiments, the extracellular antigen-binding domain comprises a $V_L$ CDR1 comprising the amino acid sequence set forth in SEQ ID NO: 54, a $V_L$ CDR2 comprising the amino acid sequence set forth in SEQ ID NO: 55, and a $V_L$ CDR3 comprising the amino acid sequence set forth in SEQ ID NO: 56. In certain embodiments, the extracellular antigen-binding domain comprises a $V_H$ CDR1 comprising the amino acid sequence set forth in SEQ ID NO: 51 or a conservative modification thereof, a $V_H$ CDR2 comprising the amino acid sequence set forth in SEQ ID NO: 52 or a conservative modification thereof, a $V_H$ CDR3 comprising the amino acid sequence set forth in SEQ ID NO: 53, a conservative modification thereof, a $V_L$ CDR1 comprising the amino acid sequence set forth in SEQ ID NO: 54 or a conservative modification thereof, a $V_L$ CDR2 comprising the amino acid sequence set forth in SEQ ID NO: 55 or a conservative modification thereof, and a $V_L$ CDR3 comprising the amino acid sequence set forth in SEQ ID NO: 56 or a conservative modification thereof. In certain embodiments, the extracellular antigen-binding domain comprises a $V_H$ CDR1 comprising amino acids having the sequence set forth in SEQ ID NO: 51, a $V_H$ CDR2 comprising the amino acid sequence set forth in SEQ ID NO: 52, a $V_H$ CDR3 comprising the amino acid sequence set forth in SEQ ID NO: 53, a $V_L$ CDR1 comprising the amino acid sequence set forth in SEQ ID NO: 54, a $V_L$ CDR2 comprising the amino acid sequence set forth in SEQ ID NO: 55 and a $V_L$ CDR3 comprising the amino acid sequence set forth in SEQ ID NO: 56.

TABLE 1

| | anti-mouse CD19 scFv (1D3) | | |
|---|---|---|---|
| CDRs | 1 | 2 | 3 |
| $V_H$ a.a. | FYYMH [SEQ ID NO: 43] | RIDPEDESTK YSEKFKN [SEQ ID NO: 44] | GGYYFDY [SEQ ID NO: 45] |
| $V_L$ a.a. | QASEDIYSGL A [SEQ ID NO: 46] | GASDLQD [SEQ ID NO: 47] | QQGLTYPRT [SEQ ID NO: 48] |
| Full $V_H$ | EVQLQQSGAE LVRPGTSVKL SCKVSGDTIT FYYMHFVKQR PGQGLEWIGR IDPEDESTKY SEKFKNKATL TADTSSNTAY LKLSSLTSED TATYFCIYGG YYFDYWGQGV MVTVSS [SEQ ID NO: 49] | | |
| Full $V_L$ | DIQMTQSPAS LSTSLGETVT IQCQASEDIY SGLAWYQQKP GKSPQLLIYG ASDLQDGVPS RFSGSGSGTQ YSLKITSMQT EDEGVYFCQQ GLTYPRTFGG GTKLELKR [SEQ ID NO: 50] | | |
| scFv | MASPLTRFLS LNLLLLGESI ILGSGEAEVQ LQQSGAELVR PGTSVKLSCK VSGDTITFYY MHFVKQRPGQ GLEWIGRIDP EDESTKYSEK FKNKATLTAD TSSNTAYLKL SSLTSEDTAT YFCIYGGYYF DYWGQGVMVT VSSGGGGSGG GGSGGGGSDI QMTQSPASLS TSLGETVTIQ CQASEDIYSG LAWYQQKPGK SPQLLIYGAS DLQDGVPSRF SGSGSGTQYS LKITSMQTED EGVYFCQQGL TYPRTFGGGT KLELKR [SEQ ID NO: 59] | | |
| DNA | ATGGCCTCACCGTTGACCCGCTTTCTGTCGCTGAACCTGCTGCTGCTGGGTGAGTCG ATTATCCTGGGGAGTGGAGAAGCTGAAGTCCAGCTGCAGCAGTCTGGGGCTGAGCTT GTGAGACCTGGGACCTCTGTGAAGTTATCTTGCAAAGTTTCTGGCGATACCATTACA TTTTACTACATGCACTTTGTGAAGCAAAGGCCTGGACAGGGTCTGGAATGGATAGGA AGGATTGATCCTGAGGATGAAAGTACTAAATATTCTGAGAAGTTCAAAAACAAGGCG ACACTCACTGCAGATACATCTTCCAACACAGCCTACCTGAAGCTCAGCAGCCTGACC TCTGAGGACACTGCAACCTATTTTTGTATCTACGGAGGATACTACTTTGATTACTGG GGCCAAGGGGTCATGGTCACAGTCTCCTCAGGTGGAGGTGGATCAGGTGGAGGTGGA TCTGGTGGAGGTGGATCTGACATCCAGATGACACAGTCTCCAGCTTCCCTGTCTACA TCTCTGGGAGAAACTGTCACCATCCAATGTCAAGCAAGTGAGGACATTTACAGTGGT TTAGCGTGGTATCAGCAGAAGCCAGGGAAATCTCCTCAGCTCCTGATCTATGGTGCA AGTGACTTACAAGACGGCGTCCCATCACGATTCAGTGGCAGTGGATCTGGCACACAG TATTCTCTCAAGATCACCAGCATGCAAACTGAAGATGAAGGGGTTTATTTCTGTCAA CAGGGTTTAACGTATCCTCGGACGTTCGGTGGCGGCACCAAGCTGGAATTGAAACGG [SEQ ID NO: 60] | | |

TABLE 2

| | anti-human CD19 scFv (SJ25C1) | | |
|---|---|---|---|
| CDRs | 1 | 2 | 3 |
| $V_H$ a.a. | GYAFSS [SEQ ID NO: 51] | YPGDGD [SEQ ID NO: 52] | KTISSVVDF [SEQ ID NO: 53] |
| $V_L$ a.a. | NVGTNVA [SEQ ID NO: 54] | SATYRN [SEQ ID NO: 55] | FCQQYNRY [SEQ ID NO: 56] |
| Full $V_H$ | EVKLQQSGAE LVRPGSSVKI SCKASGYAFS SYWMNWVKQR PGQGLEWIGQ IYPGDGDTNY NGKFKGQATL TADKSSSTAY MQLSGLTSED SAVYFCARKT ISSVVDFYFD YWGQGTTVTV SS [SEQ ID NO: 57] | | |
| Full $V_L$ | DIELTQSPKF MSTSVGDRVS VTCKASQNVG TNVAWYQQKP GQSPKPLIYS ATYRNSGVPD RFTGSGSGTD FTLTITNVQS KDLADYFCQQ YNRYPYTSGG GTKLEIKR [SEQ ID NO: 58] | | |
| scFv | MALPVTALLL PLALLLHAEV KLQQSGAELV RPGSSVKISC KASGYAFSSY WMNWVKQRPG QGLEWIGQIY PGDGDTNYNG KFKGQATLTA DKSSSTAYMQ LSGLTSEDSA VYFCARKTIS SVVDFYFDYW GQGTTVTVSS GGGGSGGGGS GGGGSDIELT QSPKFMSTSV GDRVSVTCKA SQNVGTNVAW YQQKPGQSPK PLIYSATYRN SGVPDRFTGS GSGTDFTLTI TNVQSKDLAD YFCQQYNRYP YTSGGGTKLE IKR [SEQ ID NO: 63] | | |
| DNA | ATGGCTCTCCCAGTGACTGCCCTACTGCTTCCCCTAGCGCTTCTCCTGCATGCAGAG GTGAAGCTGCAGCAGTCTGGGGCTGAGCTGGTGAGGCCTGGGTCCTCAGTGAAGATT TCCTGCAAGGCTTCTGGCTATGCATTCAGTAGCTACTGGATGAACTGGGTGAAGCAG AGGCCTGGACAGGGTCTTGAGTGGATTGGACAGATTTATCCTGGAGATGGTGATACT AACTACAATGGAAAGTTCAAGGGTCAAGCCACACTGACTGCAGACAAATCCTCCAGC ACAGCCTACATGCAGCTCAGCGGCCTAACATCTGAGGACTCTGCGGTCTATTTCTGT GCAAGAAAGACCATTAGTTCGGTAGTAGATTTCTACTTTGACTACTGGGGCCAAGGG ACCACGGTCACCGTCTCCTCAGGTGGAGGTGGATCAGGTGGAGGTGGATCTGGTGGA | | |

TABLE 2-continued anti-human CD19 scFv (SJ25C1)

| CDRs | 1 | 2 | 3 |
|---|---|---|---|
| | GGTGGATCTGACATTGAGCTCACCCAGTCTCCAAAATTCATGTCCACATCAGTAGGA GACAGGGTCAGCGTCACCTGCAAGGCCAGTCAGAATGTGGGTACTAATGTAGCCTGG TATCAACAGAAACCAGGACAATCTCCTAAACCACTGATTTACTCGGCAACCTACCGG AACAGTGGAGTCCCTGATCGCTTCACAGGCAGTGGATCTGGGACAGATTTCACTCTC ACCATCACTAACGTGCAGTCTAAAGACTTGGCAGACTATTTCTGTCAACAATATAAC AGGTATCCGTACACGTCCGGAGGGGGGACCAAGCTGGAGATCAAACGG [SEQ ID NO: 64] | | | |

As used herein, the term "a conservative sequence modification" refers to an amino acid modification that does not significantly affect or alter the binding characteristics of the presently disclosed CAR (e.g., the extracellular antigen-binding domain of the CAR) comprising the amino acid sequence. Conservative modifications can include amino acid substitutions, additions and deletions. Modifications can be introduced into the human scFv of the presently disclosed CAR by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

The $V_H$ and/or $V_L$ amino acid sequences having at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology to a specific sequence (e.g., SEQ ID NOs: 49, 50, 57, and 58) may contain substitutions (e.g., conservative substitutions), insertions, or deletions relative to the specified sequence(s), but retain the ability to bind to a target antigen (e.g., CD19). In certain embodiments, a total of 1 to 10 amino acids are substituted, inserted and/or deleted in a specific sequence (e.g., SEQ ID NOs: 49, 50, 57, and 58). In certain embodiments, substitutions, insertions, or deletions occur in regions outside the CDRs (e.g., in the FRs) of the extracellular antigen-binding domain. In certain embodiments, the extracellular antigen-binding domain comprises $V_H$ and/or $V_L$ sequence selected from the group consisting of SEQ ID NOs: 49, 50, 57, and 58, including post-translational modifications of that sequence (SEQ ID NO: 49, 50, 57, and 58).

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the amino acids sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the specified sequences (e.g., heavy and light chain variable region sequences of scFv m903, m904, m905, m906, and m900) disclosed herein. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

2.3.1. Extracellular Antigen Binding Domain of a CAR

In certain embodiments, the extracellular antigen-binding domain specifically binds to an antigen. In certain embodiments, the extracellular antigen-binding domain is an scFv. In certain embodiments, the scFv is a human scFv. In certain embodiments, the scFv is a humanized scFv. In certain embodiments, the scFv is a murine scFv. In certain embodiments, the extracellular antigen-binding domain is a Fab, which is optionally crosslinked. In certain embodiments, the extracellular antigen-binding domain is a F(ab)₂. In certain embodiments, any of the foregoing molecules may be comprised in a fusion protein with a heterologous sequence to form the extracellular antigen-binding domain. In certain embodiments, the scFv is identified by screening scFv phage library with an antigen-Fc fusion protein. In certain embodiments, the antigen is a tumor antigen. In certain embodiments, the antigen is a pathogen antigen.

2.3.2. Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3ζ polypeptide, a CD4 polypeptide, a 4-1BB polypeptide, an OX40 polypeptide, an ICOS polypeptide, a synthetic peptide (not based on a protein associated with the immune response), or a combination thereof.

In certain embodiments, the transmembrane domain comprises a CD8 polypeptide. In certain embodiments, the CD8 polypeptide comprises or has an amino acid sequence that is at least about 85%, about 90%, about 95%, about 96%, about 97%, about 98%, about 99% or about 100% homologous to the sequence having a NCBI Reference No: NP_001139345.1 (SEQ ID NO: 9) (homology herein may be determined using standard software such as BLAST or FASTA) as provided below, or fragments thereof, and/or may optionally comprise up to one or up to two or up to three conservative amino acid substitutions. In certain embodiments, the CD8 polypeptide comprises or has an amino acid sequence that is a consecutive portion of SEQ ID NO: 9 which is at least 20, or at least 30, or at least 40, or at least 50, and up to 235 amino acids in length. Alternatively or additionally, in non-limiting various embodiments, the CD8 polypeptide comprises or has an amino acid sequence of amino acids 1 to 235, 1 to 50, 50 to 100, 100 to 150, 150 to 200, or 200 to 235 of SEQ ID NO: 9. In certain embodiments, the CAR of the presently disclosed comprises a transmembrane domain comprising a CD8 polypeptide that comprises or has an amino acid sequence of amino acids 137 to 209 of SEQ ID NO: 9.

[SEQ ID NO: 9]
MALPVTALLLPLALLLHAARPSQFRVSPLDRTWNLGETVELKCQVLLSNP

TSGCSWLFQPRGAAASPTFLLYLSQNKPKAAEGLDTQRFSGKRLGDTFVL

TLSDFRRENEGYYFCSALSNSIMYFSHFVPVFLPAKPTTTPAPRPPTPAP

TIASQPLSLRPEACRPAAGGAVHTRGLDFACDIYIWAPLAGTCGVLLLSL

VITLYCNHRNRRRVCKCPRPVVKSGDKPSLSARYV

In certain embodiments, the CD8 polypeptide comprises or has an amino acid sequence that is at least about 85%, about 90%, about 95%, about 96%, about 97%, about 98%, about 99% or about 100% homologous to the sequence having a NCBI Reference No: AAA92533.1 (SEQ ID NO: 10) (homology herein may be determined using standard software such as BLAST or FASTA) as provided below, or fragments thereof, and/or may optionally comprise up to one or up to two or up to three conservative amino acid substitutions. In certain embodiments, the CD8 polypeptide comprises or has an amino acid sequence that is a consecutive portion of SEQ ID NO: 10 which is at least about 20, or at least about 30, or at least about 40, or at least about 50, or at least about 60, or at least about 70, or at least about 100, or at least about 200, and up to 247 amino acids in length. Alternatively or additionally, in non-limiting various embodiments, the CD8 polypeptide comprises or has an amino acid sequence of amino acids 1 to 247, 1 to 50, 50 to 100, 100 to 150, 150 to 200, 151 to 219, or 200 to 247 of SEQ ID NO: 10. In certain embodiments, the CAR of the presently disclosed comprises a transmembrane domain comprising a CD8 polypeptide that comprises or has an amino acid sequence of amino acids 151 to 219 of SEQ ID NO: 10.

[SEQ ID NO: 10]
  1  MASPLTREFS  LNLLLMGESI  ILGSGEAKPQ  APELRIFPKK
     MDAELGQKVD  LVCEVLGSVS

61  QGCSWLFQNS  SSKLPQPTFV  VYMASSHNKI  TWDEKLNSSK
     LFSAVRDTNN  KYVLTLNKFS

121  KENEGYYFCS  VISNSVMYFS  SVVPVLQKVN  STTTKPVLRT
     PSPVHPTGTS  QPQRPEDCRP

181  RGSVKGTGLD  FACDIYIWAP  LAGICVAPLL  SLIITLICYH
     RSRKRVCKCP  RPLVRQEGKP

241  RPSEKIV

In certain embodiments, the CD8 polypeptide comprises or has the amino acid sequence set forth in SEQ ID NO: 11, which is provided below:

[SEQ ID NO: 11]
STTTKPVLRTPSPVHPTGTSQPQRPEDCRPRGSVKGTGLDFACDIYIWAP

LAGICVALLLSLITTLICY

In accordance with the presently disclosed subject matter, a "CD8 nucleic acid molecule" refers to a polynucleotide encoding a CD8 polypeptide.

In certain embodiments, the CD8 nucleic acid molecule encoding the CD8 polypeptide having the amino acid sequence set forth in SEQ ID NO: 11 comprises or has nucleic acids having the sequence set forth in SEQ ID NO: 12 as provided below.

[SEQ ID NO: 12]
TCTACTACTACCAAGCCAGTGCTGCGAACTCCCTCACCTGTGCACCCTAC

CGGGACATCTCAGCCCCAGAGACCAGAAGATTGTCGGCCCCGTGGCTCAG

TGAAGGGGACCGGATTGGACTTCGCCTGTGATATTTACATCTGGGCACCC

TTGGCCGGAATCTGCGTGGCCCTTCTGCTGTCCTTGATCATCACTCTCAT

CTGCTAC

In certain embodiments, the transmembrane domain of a presently disclosed CAR comprises a CD28 polypeptide. The CD28 polypeptide can have an amino acid sequence that is at least about 85%, about 90%, about 95%, about 96%, about 97%, about 98%, about 99% or 100% homologous to the sequence having a NCBI Reference No: P10747 or NP_006130 (SEQ ID No: 2), or fragments thereof, and/or may optionally comprise up to one or up to two or up to three conservative amino acid substitutions. In non-limiting certain embodiments, the CD28 polypeptide comprises or has an amino acid sequence that is a consecutive portion of SEQ ID NO: 2 which is at least 20, or at least 30, or at least 40, or at least 50, and up to 220 amino acids in length.

Alternatively or additionally, in non-limiting various embodiments, the CD28 polypeptide comprises or has an amino acid sequence of amino acids 1 to 220, 1 to 50, 50 to 100, 100 to 150, 114 to 220, 150 to 200, or 200 to 220 of SEQ ID NO: 2. In certain embodiments, the CD28 polypeptide comprised in the transmembrane domain of a presently disclosed CAR comprises or has an amino acid sequence of amino acids 153 to 179 of SEQ ID NO: 2.

SEQ ID NO: 2 is provided below:

```
                                                 [SEQ ID NO: 2]
  1  MLRLLLALNL  FPSIQVTGNK  ILVKQSPMLV  AYDNAVNLSC

KYSYNLFSRE  FRASLHKGLD

61  SAVEVCVVYG  NYSQQLQVYS  KTGFNCDGKL  GNESVTFYLQ

NLYVNQTDIY  FCKIEVMYPP

121  PYLDNEKSNG  TIIHVKGKHL  CPSPLFPGPS  KPFWVLVVVG

GVLACYSLLV  TVAFIIFWVR

181  SKRSRLLHSD  YMNMTPRRPG  PTRKHYQPYA  PPRDFAAYRS
```

In accordance with the presently disclosed subject matter, a "CD28 nucleic acid molecule" refers to a polynucleotide encoding a CD28 polypeptide. In certain embodiments, the CD28 nucleic acid molecule encoding the CD28 polypeptide having amino acids 153 to 179 of SEQ ID NO: 2 comprises or has nucleic acids having the sequence set forth in SEQ ID NO: 22 as provided below.

```
                                                [SEQ ID NO: 22]
     ttttgggtgctggtggtggttggtggagtcctggcttgcta tagcttgctagtaacagtggcctttattattttctgggtg
```

In certain embodiments, the intracellular signaling domain of the CAR comprises a murine CD28 transmembrane domain. The murine CD28 transmembrane domain can comprise or have an amino acid sequence that is at least about 85%, about 90%, about 95%, about 96%, about 97%, about 98%, about 99% or about 100% homologous to SEQ ID NO: 76 or fragments thereof, and/or may optionally comprise up to one or up to two or up to three conservative amino acid substitutions. SEQ ID NO: 76 is provided below:

```
                                                [SEQ ID NO: 76]
          FWALVVVAGV  LFCYGLLVTV  ALCVIWT.
```

An exemplary nucleic acid sequence encoding the amino acid sequence of SEQ ID NO: 76 is set forth in SEQ ID NO: 77, which is provided below.

```
                                                [SEQ ID NO: 77]
     TTTTGGGCACTGGTCGTGGTTGCTGGAGTCCTGTTTTGTTA

TGGCTTGCTAGTGACAGTGGCTCTTTGTGTTATCTGGACA
```

In certain embodiments, the intracellular signaling domain of the CAR comprises a human CD28 transmembrane domain. The human CD28 transmembrane domain can comprise or have an amino acid sequence that is at least about 85%, about 90%, about 95%, about 96%, about 97%, about 98%, about 99% or about 100% homologous to SEQ ID NO: 78 or fragments thereof, and/or may optionally comprise up to one or up to two or up to three conservative amino acid substitutions. SEQ ID NO: 78 is provided below:

```
                                                [SEQ ID NO: 78]
          FWVLVVVGGV  LACYSLLVTV  AFIIFWV
```

An exemplary nucleic acid sequence encoding the amino acid sequence of SEQ ID NO: 78 is set forth in SEQ ID NO: 79, which is provided below.

```
                                                [SEQ ID NO: 79]
     TTTTGGGTGCTGGTGGTGGTTGGTGGAGTCCTGGCTTGCTA

TAGCTTGCTAGTAACAGTGGCCTTTATTATTTTCTGGGTG
```

In certain non-limiting embodiments, a CAR can also comprise a spacer region that links the extracellular antigen-binding domain to the transmembrane domain. The spacer region can be flexible enough to allow the antigen binding domain to orient in different directions to facilitate antigen recognition. The spacer region can be the hinge region from IgG1, or the $CH_2CH_3$ region of immunoglobulin and portions of CD3, a portion of a CD28 polypeptide (e.g., a portion of SEQ ID NO: 2), a portion of a CD8 polypeptide (e.g., a portion of SEQ ID NO: 9, or a portion of SEQ ID NO: 10), a variation of any of the foregoing which is at least about 80%, at least about 85%, at least about 90%, or at least about 95% homologous thereto, or a synthetic spacer sequence.

2.3.3. Intracellular Signaling Domain of a CAR

In certain non-limiting embodiments, an intracellular signaling domain of the CAR comprises a CD3ζ polypeptide, which can activate or stimulate a cell (e.g., a cell of the lymphoid lineage, e.g., a T cell). CD3ζ comprises 3 ITAMs, and transmits an activation signal to the cell (e.g., a cell of the lymphoid lineage, e.g., a T cell) after antigen is bound. The intracellular signaling domain of the CD3ζ-chain is the primary transmitter of signals from endogenous TCRs. In certain embodiments, the CD3ζ polypeptide comprises or has an amino acid sequence that is at least about 85%, about 90%, about 95%, about 96%, about 97%, about 98%, about 99% or about 100% homologous to the sequence having a NCBI Reference No: NP_932170 (SEQ ID No: 1), or fragments thereof, and/or may optionally comprise up to one or up to two or up to three conservative amino acid substitutions. In certain non-limiting embodiments, the CD3ζ polypeptide comprises or has an amino acid sequence that is a consecutive portion of SEQ ID NO: 1, which is at least 20, or at least 30, or at least 40, or at least 50, and up to 164 amino acids in length. Alternatively or additionally, in non-limiting various embodiments, the CD3ζ polypeptide comprises or has an amino acid sequence of amino acids 1 to 164, 1 to 50, 50 to 100, 100 to 150, or 150 to 164 of SEQ ID NO: 1. In certain embodiments, the CD3ζ polypeptide comprises or has an amino acid sequence of amino acids 52 to 164 of SEQ ID NO: 1.

SEQ ID NO: 1 is provided below:

```
                                                 [SEQ ID NO: 1]
  1  MKWKALFTAA  ILQAQLPITE  AQSFGLLDPK  LCYLLDGILF

IYGVILTALF  LRVKFSRSAD

61  APAYQQGQNQ  LYNELNLGRR  EEYDVLDKRR  GRDPEMGGKP
```

QRRKNPQEGL YNELQKDKMA

121 EAYSEIGMKG ERRRGKGHDG LYQGLSTATK DTYDALHMQA

LPPR

In certain embodiments, the CD3ζ polypeptide comprises or has an amino acid sequence that is at least about 85%, about 90%, about 95%, about 96%, about 97%, about 98%, about 99% or about 100% homologous to the sequence having a NCBI Reference No: NP_001106864.2 (SEQ ID No: 13), or fragments thereof, and/or may optionally comprise up to one or up to two or up to three conservative amino acid substitutions. In certain non-limiting embodiments, the CD3ζ polypeptide comprises or has an amino acid sequence that is a consecutive portion of SEQ ID NO: 13, which is at least about 20, or at least about 30, or at least about 40, or at least about 50, or at least about 90, or at least about 100, and up to 188 amino acids in length. Alternatively or additionally, in non-limiting various embodiments, the CD3ζ polypeptide comprises or has an amino acid sequence of amino acids 1 to 164, 1 to 50, 50 to 100, 52 to 142, 100 to 150, or 150 to 188 of SEQ ID NO: 13. In certain embodiments, the CD3ζ polypeptide comprises or has an amino acid sequence of amino acids 52 to 142 of SEQ ID NO: 13.

SEQ ID NO: 13 is provided below:

[SEQ ID NO: 13]
```
  1 MKWKVSVLAC ILHVRFPGAE AQSFGLLDPK LCYLLDGILF

IYGVIITALY LRAKFSRSAE

61 TAANLQDPNQ LYNELNLGRR EEYDVLEKKR ARDPEMGGKQ

RRRNPQEGVY NALQKDKMAE

121 AYSEIGTKGE RRRGKGHDGL YQDSHFQAVQ FGNRREREGS

ELTRTLGLRA RPKACRHKKP

181 LSLPAAVS
```

In certain embodiments, the CD3ζ polypeptide comprises or has the amino acid sequence set forth in SEQ ID NO: 14, which is provided below:

[SEQ ID NO: 14]
RAKFSRSAETAANLQDPNQLYNELNLGRREEYDVLEKK
RARDPEMGGKQQRRRNPQEGVYNALQKDKMAEAYSEIG
TKGERRRGKGHDGLYQGLSTATKDTYDALHMQTLAPR

In accordance with the presently disclosed subject matter, a "CD3ζ nucleic acid molecule" refers to a polynucleotide encoding a CD3ζ polypeptide. In certain embodiments, the CD3ζ nucleic acid molecule encoding the CD3ζ polypeptide having the amino acid sequence set forth in SEQ ID NO: 14 comprises or has the nucleotide sequence set forth in SEQ ID NO: 15 as provided below.

[SEQ ID NO: 15]
AGAGCAAAATTCAGCAGGAGTGCAGAGACTGCTGCCAACCTGCAG

GACCCCAACCAGCTCTACAATGAGCTCAATCTAGGGCGAAGAGAG

GAATATGACGTCTTGGAGAAGAAGCGGGCTCGGGATCCAGAGATG

GGAGGCAAACAGCAGAGGAGGAGGAACCCCCAGGAAGGCGTATAC

AATGCACTGCAGAAAGACAAGATGGCAGAAGCCTACAGTGAGATC

GGCACAAAAGGCGAGAGGCGGAGAGGCAAGGGGCACGATGGCCTT

TACCAGGGTCTCAGCACTGCCACCAAGGACACCTATGATGCCCTG

CATATGCAGACCCTGGCCCCTCGCTAA

In certain embodiments, the intracellular signaling domain of the CAR comprises a murine CD3ζ polypeptide. The murine CD3ζ polypeptide can comprise or have an amino acid sequence that is at least about 85%, about 90%, about 95%, about 96%, about 97%, about 98%, about 99% or about 100% homologous to SEQ ID NO: 72 or fragments thereof, and/or may optionally comprise up to one or up to two or up to three conservative amino acid substitutions. SEQ ID NO: 72 is provided below:

[SEQ ID NO: 72]
RAKFSRSAET AANLQDPNQL YNELNLGRRE EYDVLEKKRA

RDPEMGGKQQ RRRNPQEGVY NALQKDKMAE AYSEIGTKGE

RRRGKGHDGL YQGLSTATKD TYDALHMQTL APR.

An exemplary nucleic acid sequence encoding the amino acid sequence of SEQ ID NO: 72 is set forth in SEQ ID NO: 73, which is provided below.

[SEQ ID NO: 73]
AGAGCAAAATTCAGCAGGAGTGCAGAGACTGCTGCCAACCTGCAGG

ACCCCAACCAGCTCTACAATGAGCTCAATCTAGGGCGAAGAGAGGA

ATATGACGTCTTGGAGAAGAAGCGGGCTCGGGATCCAGAGATGGGA

GGCAAACAGCAGAGGAGGAGGAACCCCCAGGAAGGCGTATACAATG

CACTGCAGAAAGACAAGATGGCAGAAGCCTACAGTGAGATCGGCAC

AAAAGGCGAGAGGCGGAGAGGCAAGGGGCACGATGGCCTTTACCAG

GGTCTCAGCACTGCCACCAAGGACACCTATGATGCCCTGCATATGC

AGACCCTGGCCCCTCGC

In certain embodiments, the intracellular signaling domain of the CAR comprises a human CD3ζ polypeptide. The human CD3ζ polypeptide can comprise or have an amino acid sequence that is at least about 85%, about 90%, about 95%, about 96%, about 97%, about 98%, about 99% or about 100% homologous to SEQ ID NO: 74 or fragments thereof, and/or may optionally comprise up to one or up to two or up to three conservative amino acid substitutions. SEQ ID NO: 74 is provided below:

[SEQ ID NO: 74]
RVKFSRSADA PAYQQGQNQL YNELNLGRRE EYDVLDKRRG

RDPEMGGKPR RKNPQEGLYN ELQKDKMAEA YSEIGMKGER

RRGKGHDGLY QGLSTATKDT YDALHMQALP PR.

An exemplary nucleic acid sequence encoding the amino acid sequence of SEQ ID NO: 74 is set forth in SEQ ID NO: 75, which is provided below.

[SEQ ID NO: 75]
```
AGAGTGAAGTTCAGCAGGAGCGCAGACGCCCCCGCGTACCAGCAGG

GCCAGAACCAGCTCTATAACGAGCTCAATCTAGGACGAAGAGAGGA

GTACGATGTTTTGGACAAGAGACGTGGCCGGGACCCTGAGATGGGG

GGAAAGCCGAGAAGGAAGAACCCTCAGGAAGGCCTGTACAATGAAC

TGCAGAAAGATAAGATGGCGGAGGCCTACAGTGAGATTGGGATGAA

AGGCGAGCGCCGGAGGGGCAAGGGGCACGATGGCCTTTACCAGGGT

CTCAGTACAGCCACCAAGGACACCTACGACGCCCTTCACATGCAGG

CCCTGCCCCCTCGC
```

In certain non-limiting embodiments, an intracellular signaling domain of the CAR does not comprise a co-stimulatory signaling region, i.e., the CAR is a first generation CAR.

In certain non-limiting embodiments, an intracellular signaling domain of the CAR further comprises at least a co-stimulatory signaling region. In certain embodiments, the co-stimulatory region comprises at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a DAP-10 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, and 4-1BBL. As one example, a 4-1BB ligand (i.e., 4-1BBL) may bind to 4-1BB (also known as "CD137") for providing an intracellular signal that in combination with a CAR signal induces an effector cell function of the CAR' T cell. CARs comprising an intracellular signaling domain that comprises a co-stimulatory signaling region comprising 4-1BB, ICOS or DAP-10 are disclosed in U.S. Pat. No. 7,446,190, which is herein incorporated by reference in its entirety.

In certain embodiments, the intracellular signaling domain of the CAR comprises a co-stimulatory signaling region that comprises a CD28 polypeptide. The CD28 polypeptide can comprise or have an amino acid sequence that is at least about 85%, about 90%, about 95%, about 96%, about 97%, about 98%, about 99% or 100% homologous to the sequence having a NCBI Reference No: P10747 or NP_006130 (SEQ ID NO: 2), or fragments thereof, and/or may optionally comprise up to one or up to two or up to three conservative amino acid substitutions. In non-limiting certain embodiments, the CD28 polypeptide comprises or has an amino acid sequence that is a consecutive portion of SEQ ID NO: 2 which is at least 20, or at least 30, or at least 40, or at least 50, and up to 220 amino acids in length. Alternatively or additionally, in non-limiting various embodiments, the CD28 polypeptide comprises or has an amino acid sequence of amino acids 1 to 220, 1 to 50, 50 to 100, 100 to 150, 114 to 220, 150 to 200, or 200 to 220 of SEQ ID NO: 2. In certain embodiments, the intracellular signaling domain of the CAR comprises a co-stimulatory signaling region that comprises a CD28 polypeptide comprising or having an amino acid sequence of amino acids 180 to 220 of SEQ ID NO: 2.

In certain embodiments, the CD28 polypeptide comprises or has an amino acid sequence that is at least about 85%, about 90%, about 95%, about 96%, about 97%, about 98%, about 99% or about 100% homologous to the sequence having a NCBI Reference No: NP_031668.3 (SEQ ID NO: 16), or fragments thereof, and/or may optionally comprise up to one or up to two or up to three conservative amino acid substitutions. In non-limiting certain embodiments, the CD28 polypeptide comprises or has an amino acid sequence that is a consecutive portion of SEQ ID NO: 16 which is at least about 20, or at least about 30, or at least about 40, or at least about 50, and up to 218 amino acids in length. Alternatively or additionally, in non-limiting various embodiments, the CD28 polypeptide comprises or has an amino acid sequence of amino acids 1 to 218, 1 to 50, 50 to 100, 100 to 150, 114 to 220, 150 to 200, 178 to 218, or 200 to 220 of SEQ ID NO: 16. In certain embodiments, the co-stimulatory signaling region of a presently disclosed CAR comprises a CD28 polypeptide that comprises or has the amino acids 178 to 218 of SEQ ID NO: 16.

SEQ ID NO: 16 is provided below:

[SEQ ID NO: 16]
```
  1 MTLRLLFLAL NFFSVQVTEN KILVKQSPLL VVDSNEVSLS

CRYSYNLLAK EFRASLYKGV

61 NSDVEVCVGN GNFTYQPQFR SNAEFNCDGD FDNETVTFRL

WNLHVNHTDI YFCKIEFMYP

121 PPYLDNERSN GTIIHIKEKH LCHTQSSPKL FWALVVVAGV

LFCYGLLVTV ALCVIWTNSR

181 RNRLLQSDYM NMTPRRPGLT RKPYQPYAPA RDFAAYRP
```

In accordance with the presently disclosed subject matter, a "CD28 nucleic acid molecule" refers to a polynucleotide encoding a CD28 polypeptide. In certain embodiments, a CD28 nucleic acid molecule that encodes a CD28 polypeptide comprised in the co-stimulatory signaling region of a presently disclosed CAR (e.g., amino acids 178 to 218 of SEQ ID NO: 16) comprises or has a nucleotide sequence set forth in SEQ ID NO: 17, which is provided below.

[SEQ ID NO: 17]
```
AATAGTAGAAGGAACAGACTCCTTCAAAGTGACTACATGAACATGA

CTCCCCGGAGGCCTGGGCTCACTCGAAAGCTTACCAGCCCTACGCC

CCTGCCAGAGACTTTGCAGCGTACCGCCCC
```

In certain embodiments, the intracellular signaling domain of the CAR comprises a murine intracellular signaling domain of CD28. The murine intracellular signaling domain of CD28 can comprise or have an amino acid sequence that is at least about 85%, about 90%, about 95%, about 96%, about 97%, about 98%, about 99% or about 100% homologous to SEQ ID NO: 68 or fragments thereof, and/or may optionally comprise up to one or up to two or up to three conservative amino acid substitutions. SEQ ID NO: 68 is provided below:

[SEQ ID NO: 68]
NSRRNRLLQS DYMNMTPRR GLTRKPYQPY APARDFAAYR P

An exemplary nucleic acid sequence encoding the amino acid sequence of SEQ ID NO: 68 is set forth in SEQ ID NO: 69, which is provided below.

[SEQ ID NO: 69]
AATAGTAGAAGGAACAGACTCCTTCAAAGTGACTACATGAA

CATGACTCCCCGGAGGCCTGGGCTCACTCGAAAGCCTTACC

AGCCCTACGCCCCTGCCAGAGACTTTGCAGCGTACCGCCCC

In certain embodiments, the intracellular signaling domain of the CAR comprises a human intracellular signaling domain of CD28. The human intracellular signaling domain of CD28 can comprise or have an amino acid sequence that is at least about 85%, about 90%, about 95%, about 96%, about 97%, about 98%, about 99% or about 100% homologous to SEQ ID NO: 70 or fragments thereof, and/or may optionally comprise up to one or up to two or up to three conservative amino acid substitutions. SEQ ID NO: 70 is provided below:

[SEQ ID NO: 70]
RSKRSRLLHS DYMNMTPRRP GPTRKHYQPY APPRDFAAYR S

An exemplary nucleic acid sequence encoding the amino acid sequence of SEQ ID NO: 70 is set forth in SEQ ID NO: 71, which is provided below.

[SEQ ID NO: 71]
AGGAGTAAGAGGAGCAGGCTCCTGCACAGTGACTACATGAA

CATGACTCCCCGCCGCCCCGGGCCCACCCGCAAGCATTACC

AGCCCTATGCCCCACCACGCGACTTCGCAGCCTATCGCTCC

In certain embodiments, the intracellular signaling domain of the CAR comprises a co-stimulatory signaling region that comprises two co-stimulatory molecules: CD28 and 4-1BB or CD28 and OX40.

4-1BB can act as a tumor necrosis factor (TNF) ligand and have stimulatory activity. The 4-1BB polypeptide can comprise or have an amino acid sequence that is at least about 85%, about 90%, about 95%, about 96%, about 97%, about 98%, about 99% or about 100% homologous to the sequence having a NCBI Reference No: P41273 or NP_001552 (SEQ ID NO: 3) or fragments thereof, and/or may optionally comprise up to one or up to two or up to three conservative amino acid substitutions.

SEQ ID NO: 3 is provided below:

[SEQ ID NO: 3]
1   MGNSCYNIVA TLLLVLNFER TRSLQDPCSN CPAGTFCDNN

RNQICSPCPP NSFSSAGGQR

61  TCDICRQCKG VFRTRKECSS TSNAECDCTP GFHCLGAGCS

MCEQDCKQGQ ELTKKGCKDC

121 CFGTFNDQKR GICRPWTNCS LDGKSVLVNG TKERDVVCGP

SPADLSPGAS SVTPPAPARE

181 PGHSPQIISF FLALTSTALL FLLFFLTLRF SVVKRGRKKL

LYIFKQPFMR PVQTTQEEDG

241 CSCRFPEEEE GGCEL

In accordance with the presently disclosed subject matter, a "4-1BB nucleic acid molecule" refers to a polynucleotide encoding a 4-1BB polypeptide.

In certain embodiments, the intracellular signaling domain of the CAR comprises an intracellular signaling domain of 4-1BB. The intracellular signaling domain of 4-1BB can comprise or have an amino acid sequence that is at least about 85%, about 90%, about 95%, about 96%, about 97%, about 98%, about 99% or about 100% homologous to SEQ ID NO: 66 or fragments thereof, and/or may optionally comprise up to one or up to two or up to three conservative amino acid substitutions. SEQ ID NO: 66 is provided below:

[SEQ ID NO: 66]
KRGRKKLLYI FKQPFMRPVQ TTQEEDGCSC RFPEEEEGGC EL

An exemplary nucleic acid sequence encoding the amino acid sequence of SEQ ID NO: 66 is set forth in SEQ ID NO: 67, which is provided below.

[SEQ ID NO: 67]
AAACGGGGCAGAAAGAAACTCCTGTATATATTCAAACAACCA

TTTATGAGACCAGTACAAACTACTCAAGAGGAAGATGGCTGT

AGCTGCCGATTTCCAGAAGAAGAAGAAGGAGGATGTGAACTG

An OX40 polypeptide can comprise or have an amino acid sequence that is at least about 85%, about 90%, about 95%, about 96%, about 97%, about 98%, about 99% or about 100% homologous to the sequence having a NCBI Reference No: P43489 or NP_003318 (SEQ ID NO: 18), or fragments thereof, and/or may optionally comprise up to one or up to two or up to three conservative amino acid substitutions.

SEQ ID NO: 18 is provided below:

[SEQ ID NO: 18]
1   MCVGARRLGR GPCAALLLLG LGLSTVTGLH CVGDTYPSND

RCCHECRPGN GMVSRCSRSQ

61  NTVCRPCGPG FYNDVVSSKP CKPCTWCNLR SGSERKQLCT

ATQDTVCRCR AGTQPLDSYK

121 PGVDCAPCPP GHFSPGDNQA CKPWTNCTLA GKHTLQPASN

SSDAICEDRD PPATQPQETQ

181 GPPARPITVQ PTEAWPRTSQ GPSTRPVEVP GGRAVAAILG

LGLVLGLLGP LAILLALYLL

241 RRDQRLPPDA HKPPGGGSFR TPIQEEQADA HSTLAKI

In accordance with the presently disclosed subject matter, an "OX40 nucleic acid molecule" refers to a polynucleotide encoding an OX40 polypeptide.

An ICOS polypeptide can comprise or have an amino acid sequence that is at least about 85%, about 90%, about 95%, about 96%, about 97%, about 98%, about 99% or about 100% homologous to the sequence having a NCBI Reference No: NP_036224 (SEQ ID NO: 19) or fragments thereof, and/or may optionally comprise up to one or up to two or up to three conservative amino acid substitutions.

SEQ ID NO: 19 is provided below:

```
                                                [SEQ ID NO: 19]
  1  MKSGLWYFFL  FCLRIKVLTG  EINGSANYEM  FIFHNGGVQI

LCKYPDIVQQ  FKMQLLKGGQ

61  ILCDLIKTKG  SGNTVSIKSL  KFCHSQLSNN  SVSFFLYNLD

HSHANYYFCN  LSIFDPPPFK

121  VTLIGGYLHI  YESQLCCQLK  FWLPIGCAAF  VVVCILGCIL

ICWLTKKKYS  SSVHDPNGEY

181  MFMRAVNTAK  KSRLTDVTL
```

In accordance with the presently disclosed subject matter, an "ICOS nucleic acid molecule" refers to a polynucleotide encoding an ICOS polypeptide.

In certain embodiments, a presently disclosed CAR further comprises an inducible promoter, for expressing nucleic acid sequences in human cells. Promoters for use in expressing CAR genes can be a constitutive promoter, such as ubiquitin C (UbiC) promoter.

In certain embodiments, a presently disclosed CAR comprises an extracellular antigen-binding domain that binds to CD19 (e.g., murine CD19), a transmembrane domain comprising a CD28 polypeptide, and an intracellular signaling domain comprising a CD3ζ polypeptide (e.g., a murine CD3ζ polypeptide), wherein the intracellular signaling domain does not comprise a co-stimulatory signaling region, namely, the CAR is a first generation CAR. In certain embodiments, the CAR is designated as "m19mz" (or "am19mz"). In certain embodiments, the CAR (e.g., m19mz) comprises an amino acid sequence that is at least about 85%, about 90%, about 95%, about 96%, about 97%, about 98%, about 99% or about 100% homologous to the amino acid sequence set forth in SEQ ID NO: 5, which is provided below.

```
                                                [SEQ ID NO:5]
  MASPLTRFLS  LNLLLLGESI  ILGSGEAEVQ  LQQSGAELVR

PGTSVKLSCK  VSGDTITFYY  MHFVKQRPGQ  GLEWIGRIDP

EDESTKYSEK  FKNKATLTAD  TSSNTAYLKL  SSLTSEDTAT

YFCIYGGYYF  DYWGQGVMVT  VSSGGGGSGG  GGSGGGGSDI

QMTQSPASLS  TSLGETVTIQ  CQASEDIYSG  LAWYQQKPGK

SPQLLIYGAS  DLQDGVPSRF  SGSGSGTQYS  LKITSMQTED

EGVYFCQQGL  TYPRTFGGGT  KLELKRAAAE  QKLISEEDLI

EFMYPPPYLD  NERSNGTIIH  IKEKHLCHTQ  SSPKLFWALV

VVAGVLFCYG  LLVTVALCVI  WTRAKFSRSA  ETAANLQDPN

QLYNELNLGR  REEYDVLEKK  RARDPEMGGK  QQRRRNPQEG

VYNALQKDKM  AEAYSEIGTK  GERRRGKGHD  GLYQGLSTAT

KDTYDALHMQ  TLAPR
```

SEQ ID NO: 5 includes a CD8 leader sequence at amino acids 1 to 27, and is able to bind to CD19 (e.g., murine CD19).

An exemplary nucleic acid sequence encoding the amino acid sequence of SEQ ID NO: 5 is set forth in SEQ ID NO: 65, which is provided below.

```
[SEQ ID NO: 65]
ATGGCCTCACCGTTGACCCGCTTTCTGTCGCTGAACCTGCTGCTGC

TGGGTGAGTCGATTATCCTGGGGAGTGGAGAAGCTGAAGTCCAGCT

GCAGCAGTCTGGGGCTGAGCTTGTGAGACCTGGGACCTCTGTGAAG

TTATCTTGCAAAGTTTCTGGCGATACCATTACATTTTACTACATGC

ACTTTGTGAAGCAAAGGCCTGGACAGGGTCTGGAATGGATAGGAAG

GATTGATCCTGAGGATGAAAGTACTAAATATTCTGAGAAGTTCAAA

AACAAGGCGACACTCACTGCAGATACATCTTCCAACACAGCCTACC

TGAAGCTCAGCAGCCTGACCTCTGAGGACACTGCAACCTATTTTTG

TATCTACGGAGGATACTACTTTGATTACTGGGGCCAAGGGGTCATG

GTCACAGTCTCCTCAGGTGGAGGTGGATCAGGTGGAGGTGGATCTG

GTGGAGGTGGATCTGACATCCAGATGACACAGTCTCCAGCTTCCCT

GTCTACATCTCTGGGAGAAACTGTCACCATCCAATGTCAAGCAAGT

GAGGACATTTACAGTGGTTTAGCGTGGTATCAGCAGAAGCCAGGGA

AATCTCCTCAGCTCCTGATCTATGGTGCAAGTGACTTACAAGACGG

CGTCCCATCACGATTCAGTGGCAGTGGATCTGGCACACAGTATTCT

CTCAAGATCACCAGCATGCAAACTGAAGATGAAGGGGTTTATTTCT

GTCAACAGGGTTTAACGTATCCTCGGACGTTCGGTGGCGGCACCAA

GCTGGAATTGAAACGGGCGGCCGCAGAACAGAAACTGATCTCTGAA

GAAGACCTGATTGAGTTCATGTACCCTCCGCCTTACCTAGACAACG

AGAGGAGCAATGGAACTATTATTCACATAAAAGAGAAACATCTTTG

TCATACTCAGTCATCTCCTAAGCTGTTTTGGGCACTGGTCGTGGTT

GCTGGAGTCCTGTTTTGTTATGGCTTGCTAGTGACAGTGGCTCTTT

GTGTTATCTGGACAAGAGCAAAATTCAGCAGGAGTGCAGAGACTGC

TGCCAACCTGCAGGACCCCAACCAGCTCTACAATGAGCTCAATCTA

GGGCGAAGAGAGGAATATGACGTCTTGGAGAAGAAGCGGGCTCGGG

ATCCAGAGATGGGAGGCAAACAGCAGAGGAGGAGGAACCCCCAGGA

AGGCGTATACAATGCACTGCAGAAAGACAAGATGGCAGAAGCCTAC

AGTGAGATCGGCACAAAAGGCGAGAGGCGGAGAGGCAAGGGGCACG

ATGGCCTTTACCAGGGTCTCAGCACTGCCACCAAGGACACCTATGA

TGCCCTGCATATGCAGACCCTGGCCCCTCGCTAA
```

In certain embodiments, a presently disclosed CAR comprises an extracellular antigen-binding domain that binds to CD19 (e.g., murine CD19), a transmembrane domain comprising a CD28 polypeptide, and an intracellular signaling domain comprising a CD3ζ polypeptide (e.g., a murine CD3ζ polypeptide) and a co-stimulatory signaling region comprising a CD28 polypeptide (e.g., a murine CD28 polypeptide). In certain embodiments, the CAR is designated as "m19m28z" (or "am19m28z"). In certain embodiments, the CAR (e.g., m19m28z) comprises an amino acid sequence that is at least about 85%, about 90%, about 95%, about 96%, about 97%, about 98%, about 99% or about 100% homologous to the amino acid sequence set forth in SEQ ID NO: 6, which is provided below.

[SEQ ID NO: 6]
```
MASPLTRFLS LNLLLLGESI ILGSGEAEVQ LQQSGAELVR

PGTSVKLSCK VSGDTITFYY MHFVKQRPGQ GLEWIGRIDP

EDESTKYSEK FKNKATLTAD TSSNTAYLKL SSLTSEDTAT

YFCIYGGYYF DYWGQGVMVT VSSGGGGSGG GGSGGGGSDI

QMTQSPASLS TSLGETVTIQ CQASEDIYSG LAWYQQKPGK

SPQLLIYGAS DLQDGVPSRF SGSGSGTQYS LKITSMQTED

EGVYFCQQGL TYPRTFGGGT KLELKRAAAE QKLISEEDLI

EFMYPPPYLD NERSNGTIIH IKEKHLCHTQ SSPKLFWALV

VVAGVLFCYG LLVTVALCVI WTNSRRNRLL QSDYMNMTPR

RPGLTRKPYQ PYAPARDFAA YRPRAKFSRS AETAANLQDP

NQLYNELNLG RREEYDVLEK KRARDPEMGG KQQRRRNPQE

GVYNALQKDK MAEAYSEIGT KGERRRGKGH DGLYQGLSTA

TKDTYDALHM QTLAPR
```

SEQ ID NO: 6 includes a CD8 leader sequence at amino acids 1 to 27, and is able to bind to CD19 (e.g., murine CD19). An exemplary nucleic acid sequence encoding the amino acid sequence of SEQ ID NO: 6 is set forth in SEQ ID NO:7, which is provided below.

[SEQ ID NO: 7]
```
ATGGCCTCACCGTTGACCCGCTTTCTGTCGCTGAACCTGCTGCT

GCTGGGTGAGTCGATTATCCTGGGGAGTGGAGAAGCTGAAGTCC

AGCTGCAGCAGTCTGGGGCTGAGCTTGTGAGACCTGGGACCTCT

GTGAAGTTATCTTGCAAAGTTTCTGGCGATACCATTACATTTTA

CTACATGCACTTTGTGAAGCAAAGGCCTGGACAGGGTCTGGAAT

GGATAGGAAGGATTGATCCTGAGGATGAAAGTACTAAATATTCT

GAGAAGTTCAAAAACAAGGCGACACTCACTGCAGATACATCTTC

CAACACAGCCTACCTGAAGCTCAGCAGCCTGACCTCTGAGGACA

CTGCAACCTATTTTTGTATCTACGGAGGATACTACTTTGATTAC

TGGGGCCAAGGGGTCATGGTCACAGTCTCCTCAGGTGGAGGTGG

ATCAGGTGGAGGTGGATCTGGTGGAGGTGGATCTGACATCCAGA

TGACACAGTCTCCAGCTTCCCTGTCTACATCTCTGGGAGAAACT

GTCACCATCCAATGTCAAGCAAGTGAGGACATTTACAGTGGTTT

AGCGTGGTATCAGCAGAAGCCAGGGAAATCTCCTCAGCTCCTGA

TCTATGGTGCAAGTGACTTACAAGACGGCGTCCCATCACGATTC

AGTGGCAGTGGATCTGGCACACAGTATTCTCTCAAGATCACCAG

CATGCAAACTGAAGATGAAGGGGTTTATTTCTGTCAACAGGGTT

TAACGTATCCTCGGACGTTCGGTGGCGGCACCAAGCTGGAATTG

AAACGGGCGGCCGCAGAACAGAAACTGATCTCTGAAGAAGACCT

GATTGAGTTCATGTACCCTCCGCCTTACCTAGACAACGAGAGGA

GCAATGGAACTATTATTCACATAAAAGAGAAACATCTTTGTCAT

ACTCAGTCATCTCCTAAGCTGTTTTGGGCACTGGTCGTGGTTGC
```

TGGAGTCCTGTTTTGTTATGGCTTGCTAGTGACAGTGGCTCTTT

GTGTTATCTGGACAAATAGTAGAAGGAACAGACTCCTTCAAAGT

GACTACATGAACATGACTCCCCGGAGGCCTGGGCTCACTCGAAA

GCCTTACCAGCCCTACGCCCCTGCCAGAGACTTTGCAGCGTACC

GCCCCAGAGCAAAATTCAGCAGGAGTGCAGAGACTGCTGCCAAC

CTGCAGGACCCCAACCAGCTCTACAATGAGCTCAATCTAGGGCG

AAGAGAGGAATATGACGTCTTGGAGAAGAAGCGGGCTCGGGATC

CAGAGATGGGAGGCAAACAGCAGAGGAGGAGGAACCCCCAGGAA

GGCGTATACAATGCACTGCAGAAAGACAAGATGGCAGAAGCCTA

CAGTGAGATCGGCACAAAAGGCGAGAGGCGGAGAGGCAAGGGGC

ACGATGGCCTTTACCAGGGTCTCAGCACTGCCACCAAGGACACC

TATGATGCCCTGCATATGCAGACCCTGGCCCCTCGCTAA

In certain embodiments, a presently disclosed CAR comprises an extracellular antigen-binding domain that binds to CD19 (e.g., human CD19), a transmembrane domain comprising a CD28 polypeptide, and an intracellular signaling domain comprising a CD3ζ polypeptide (e.g., a murine CD3ζ polypeptide), wherein the intracellular signaling domain does not comprise a co-stimulatory signaling region, namely, the CAR is a first generation CAR. In certain embodiments, the CAR is designated as "ah19mz". In certain embodiments, the CAR (e.g., ah19mz) comprises an amino acid sequence that is at least about 85%, about 90%, about 95%, about 96%, about 97%, about 98%, about 99% or about 100% homologous to the amino acid sequence set forth in SEQ ID NO: 33, which is provided below. SEQ ID NO: 33 includes a CD8 leader sequence at amino acids 1 to 18, and is able to bind to CD19 (e.g., human CD19)

[SEQ ID NO: 33]
```
MALPVTALLL PLALLLHAEV KLQQSGAELV RPGSSVKISC

KASGYAFSSY WMNWVKQRPG QGLEWIGQIY PGDGDTNYNG

KFKGQATLTA DKSSSTAYMQ LSGLTSEDSA VYFCARKTIS

SVVDFYFDYW GQGTTVTVSS GGGGSGGGGS GGGGSDIELT

QSPKFMSTSV GDRVSVTCKA SQNVGTNVAW YQQKPGQSPK

PLIYSATYRN SGVPDRFTGS GSGTDFTLTI TNVQSKDLAD

YFCQQYNRYP YTSGGGTKLE IKRAAAIEFM YPPPYLDNER

SNGTIIHIKE KHLCHTQSSP KLFWALVVVA GVLFCYGLLV

TVALCVIWTR AKFSRSAETA ANLQDPNQLY NELNLGRREE

YDVLEKKRAR DPEMGGKQQR RRNPQEGVYN ALQKDKMAEA

YSEIGTKGER RRGKGHDGLY QGLSTATKDT YDALHMQTLA

PR
```

An exemplary nucleic acid sequence encoding the amino acid sequence of SEQ ID NO: 33 is set forth in SEQ ID NO: 34, which is provided below.

[SEQ ID NO: 34]
```
ATGGCTCTCCCAGTGACTGCCCTACTGCTTCCCCTAGCGCTTCT
```

```
CCTGCATGCAGAGGTGAAGCTGCAGCAGTCTGGGGCTGAGCTGG

TGAGGCCTGGGTCCTCAGTGAAGATTTCCTGCAAGGCTTCTGGC

TATGCATTCAGTAGCTACTGGATGAACTGGGTGAAGCAGAGGCC

TGGACAGGGTCTTGAGTGGATTGGACAGATTTATCCTGGAGATG

GTGATACTAACTACAATGGAAAGTTCAAGGGTCAAGCCACACTG

ACTGCAGACAAATCCTCCAGCACAGCCTACATGCAGCTCAGCGG

CCTAACATCTGAGGACTCTGCGGTCTATTTCTGTGCAAGAAAGA

CCATTAGTTCGGTAGTAGATTTCTACTTTGACTACTGGGGCCAA

GGGACCACGGTCACCGTCTCCTCAGGTGGAGGTGGATCAGGTGG

AGGTGGATCTGGTGGAGGTGGATCTGACATTGAGCTCACCCAGT

CTCCAAAATTCATGTCCACATCAGTAGGAGACAGGGTCAGCGTC

ACCTGCAAGGCCAGTCAGAATGTGGGTACTAATGTAGCCTGGTA

TCAACAGAAACCAGGACAATCTCCTAAACCACTGATTTACTCGG

CAACCTACCGGAACAGTGGAGTCCCTGATCGCTTCACAGGCAGT

GGATCTGGGACAGATTTCACTCTCACCATCACTAACGTGCAGTC

TAAAGACTTGGCAGACTATTTCTGTCAACAATATAACAGGTATC

CGTACACGTCCGGAGGGGGGACCAAGCTGGAGATCAAACGGGCG

GCCGCAATTGAGTTCATGTACCCTCCGCCTTACCTAGACAACGA

GAGGAGCAATGGAACTATTATTCACATAAAAGAGAAACATCTTT

GTCATACTCAGTCATCTCCTAAGCTGTTTTGGGCACTGGTCGTG

GTTGCTGGAGTCCTGTTTTGTTATGGCTTGCTAGTGACAGTGGC

TCTTTGTGTTATCTGGACAAGAGCAAAATTCAGCAGGAGTGCAG

AGACTGCTGCCAACCTGCAGGACCCCAACCAGCTCTACAATGAG

CTCAATCTAGGGCGAAGAGAGGAATATGACGTCTTGGAGAAGAA

GCGGGCTCGGGATCCAGAGATGGGAGGCAAACAGCAGAGGAGGA

GGAACCCCAGGAAGGCGTATACAATGCACTGCAGAAAGACAAG

ATGGCAGAAGCCTACAGTGAGATCGGCACAAAAGGCGAGAGGCG

GAGAGGCAAGGGGCACGATGGCCTTTACCAGGGTCTCAGCACTG

CCACCAAGGACACCTATGATGCCCTGCATATGCAGACCCTGGCC

CCTCGCTAA
```

In certain embodiments, a presently disclosed CAR comprises an extracellular antigen-binding domain that binds to CD19 (e.g., human CD19), a transmembrane domain comprising a CD28 polypeptide, and an intracellular signaling domain comprising a CD3ζ polypeptide (e.g., a human CD3ζ polypeptide), wherein the intracellular signaling domain does not comprise a co-stimulatory signaling region, namely, the CAR is a first generation CAR. In certain embodiments, the CAR is designated as "ah19 hz". In certain embodiments, the CAR (e.g., ah19 hz) comprises an amino acid sequence that is at least about 85%, about 90%, about 95%, about 96%, about 97%, about 98%, about 99% or about 100% homologous to the amino acid sequence set forth in SEQ ID NO: 35, which is provided below. SEQ ID NO: 35 includes a CD8 leader sequence at amino acids 1 to 18, and is able to bind to CD19 (e.g., human CD19).

```
                                           [SEQ ID NO: 35]
MALPVTALLL PLALLLHAEV KLQQSGAELV RPGSSVKISC

KASGYAFSSY WMNWVKQRPG QGLEWIGQIY PGDGDTNYNG

KFKGQATLTA DKSSSTAYMQ LSGLTSEDSA VYFCARKTIS

SVVDFYFDYW GQGTTVTVSS GGGGSGGGGS GGGGSDIELT

QSPKFMSTSV GDRVSVTCKA SQNVGTNVAW YQQKPGQSPK

PLIYSATYRN SGVPDRFTGS GSGTDFTLTI TNVQSKDLAD

YFCQQYNRYP YTSGGGTKLE IKRAAAIEVM YPPPYLDNEK

SNGTIIHVKG KHLCPSPLFP GPSKPFWVLV VVGGVLACYS

LLVTVAFIIF WVRVKFSRSA DAPAYQQGQN QLYNELNLGR

REEYDVLDKR RGRDPEMGGK PRRKNPQEGL YNELQKDKMA

EAYSEIGMKG ERRRGKGHDG LYQGLSTATK DTYDALHMQA

LPPR
```

An exemplary nucleic acid sequence encoding the amino acid sequence of SEQ ID NO: 35 is set forth in SEQ ID NO: 36, which is provided below.

```
                                           [SEQ ID NO: 36]
ATGGCTCTCCCAGTGACTGCCCTACTGCTTCCCCTAGCGCTTCTCC

TGCATGCAGAGGTGAAGCTGCAGCAGTCTGGGGCTGAGCTGGTGAG

GCCTGGGTCCTCAGTGAAGATTTCCTGCAAGGCTTCTGGCTATGCA

TTCAGTAGCTACTGGATGAACTGGGTGAAGCAGAGGCCTGGACAGG

GTCTTGAGTGGATTGGACAGATTTATCCTGGAGATGGTGATACTAA

CTACAATGGAAAGTTCAAGGGTCAAGCCACACTGACTGCAGACAAA

TCCTCCAGCACAGCCTACATGCAGCTCAGCGGCCTAACATCTGAGG

ACTCTGCGGTCTATTTCTGTGCAAGAAAGACCATTAGTTCGGTAGT

AGATTTCTACTTTGACTACTGGGGCCAAGGGACCACGGTCACCGTC

TCCTCAGGTGGAGGTGGATCAGGTGGAGGTGGATCTGGTGGAGGTG

GATCTGACATTGAGCTCACCCAGTCTCCAAAATTCATGTCCACATC

AGTAGGAGACAGGGTCAGCGTCACCTGCAAGGCCAGTCAGAATGTG

GGTACTAATGTAGCCTGGTATCAACAGAAACCAGGACAATCTCCTA

AACCACTGATTTACTCGGCAACCTACCGGAACAGTGGAGTCCCTGA

TCGCTTCACAGGCAGTGGATCTGGGACAGATTTCACTCTCACCATC

ACTAACGTGCAGTCTAAAGACTTGGCAGACTATTTCTGTCAACAAT

ATAACAGGTATCCGTACACGTCCGGAGGGGGGACCAAGCTGGAGAT

CAAACGGGCGGCCGCAATTGAGTTATGTATCCTCCTCCTTACCTA

GACAATGAGAAGAGCAATGGAACCATTATCCATGTGAAAGGGAAAC

ACCTTTGTCCAAGTCCCCTATTTCCCGGACCTTCTAAGCCCTTTTG

GGTGCTGGTGGTGGTTGGTGGAGTCCTGGCTTGCTATAGCTTGCTA

GTAACAGTGGCCTTTATTATTTTCTGGGTGAGAGTGAAGTTCAGCA

GGAGCGCAGACGCCCCCGCGTACCAGCAGGGCCAGAACCAGCTCTA

TAACGAGCTCAATCTAGGACGAAGAGAGGAGTACGATGTTTTGGAC

AAGAGACGTGGCCGGGACCCTGAGATGGGGGGAAAGCCGAGAAGGA
```

```
AGAACCCTCAGGAAGGCCTGTACAATGAACTGCAGAAAGATAAGAT

GGCGGAGGCCTACAGTGAGATTGGGATGAAAGGCGAGCGCCGGAGG

GGCAAGGGGCACGATGGCCTTTACCAGGGTCTCAGTACAGCCACCA

AGGACACCTACGACGCCCTTCACATGCAGGCCCTGCCCCCTCGCTAG
```

In certain embodiments, a presently disclosed CAR comprises an extracellular antigen-binding domain that binds to CD19 (e.g., human CD19), a transmembrane domain comprising a CD28 polypeptide, and an intracellular signaling domain comprising a CD3ζ polypeptide (e.g., a murine CD3ζ polypeptide) and a co-stimulatory signaling region comprising a CD28 polypeptide (e.g., a murine CD28 polypeptide). In certain embodiments, the CAR is designated as "ah19m28z".

In certain embodiments, the CAR (e.g., ah19m28z) comprises an amino acid sequence that is at least about 85%, about 90%, about 95%, about 96%, about 97%, about 98%, about 99% or about 100% homologous to the amino acid sequence set forth in SEQ ID NO: 37, which is provided below. SEQ ID NO: 37 includes a CD8 leader sequence at amino acids 1 to 18, and is able to bind to CD19 (e.g., human CD19).

```
                                              [SEQ ID NO: 37]
MALPVTALLL  PLALLLHAEV  KLQQSGAELV  RPGSSVKISC

KASGYAFSSY  WMNWVKQRPG  QGLEWIGQIY  PGDGDTNYNG

KFKGQATLTA  DKSSSTAYMQ  LSGLTSEDSA  VYFCARKTIS

SVVDFYFDYW  GQGTTVTVSS  GGGGSGGGGS  GGGGSDIELT

QSPKFMSTSV  GDRVSVTCKA  SQNVGTNVAW  YQQKPGQSPK

PLIYSATYRN  SGVPDRFTGS  GSGTDFTLTI  TNVQSKDLAD

YFCQQYNRYP  YTSGGGTKLE  IKRAAAIEFM  YPPPYLDNER

SNGTIIHIKE  KHLCHTQSSP  KLFWALVVVA  GVLFCYGLLV

TVALCVIWTN  SRRNRLLQSD  YMNMTPRRPG  LTRKPYQPYA

PARDFAAYRP  RAKFSRSAET  AANLQDPNQL  YNELNLGRRE

EYDVLEKKRA  RDPEMGGKQQ  RRRNPQEGVY  NALQKDKMAE

AYSEIGTKGE  RRRGKGHDGL  YQGLSTATKD  TYDALHMQTL

APR
```

An exemplary nucleic acid sequence encoding the amino acid sequence of SEQ ID NO: 37 is set forth in SEQ ID NO: 38, which is provided below.

```
                                              [SEQ ID NO: 38]
ATGGCTCTCCCAGTGACTGCCCTACTGCTTCCCCTAGCGCTTCTCCTG

CATGCAGAGGTGAAGCTGCAGCAGTCTGGGGCTGAGCTGGTGAGGCCT

GGGTCCTCAGTGAAGATTTCCTGCAAGGCTTCTGGCTATGCATTCAGT

AGCTACTGGATGAACTGGGTGAAGCAGAGGCCTGGACAGGGTCTTGAG

TGGATTGGACAGATTTATCCTGGAGATGGTGATACTAACTACAATGGA

AAGTTCAAGGGTCAAGCCACACTGACTGCAGACAAATCCTCCAGCACA

GCCTACATGCAGCTCAGCGGCCTAACATCTGAGGACTCTGCGGTCTAT

TTCTGTGCAAGAAAGACCATTAGTTCGGTAGTAGATTTCTACTTTGAC

TACTGGGGCCAAGGGACCACGGTCACCGTCTCCTCAGGTGGAGGTGGA

TCAGGTGGAGGTGGATCTGGTGGAGGTGGATCTGACATTGAGCTCACC

CAGTCTCCAAAATTCATGTCCACATCAGTAGGAGACAGGGTCAGCGTC

ACCTGCAAGGCCAGTCAGAATGTGGGTACTAATGTAGCCTGGTATCAA

CAGAAACCAGGACAATCTCCTAAACCACTGATTTACTCGGCAACCTAC

CGGAACAGTGGAGTCCCTGATCGCTTCACAGGCAGTGGATCTGGGACA

GATTTCACTCTCACCATCACTAACGTGCAGTCTAAAGACTTGGCAGAC

TATTTCTGTCAACAATATAACAGGTATCCGTACACGTCCGGAGGGGGG

ACCAAGCTGGAGATCAAACGGGCGGCCGCAATTGAGTTCATGTACCCT

CCGCCTTACCTAGACAACGAGAGGAGCAATGGAACTATTATTCACATA

AAAGAGAAACATCTTTGTCATACTCAGTCATCTCCTAAGCTGTTTTGG

GCACTGGTCGTGGTTGCTGGAGTCCTGTTTTGTTATGGCTTGCTAGTG

ACAGTGGCTCTTTGTGTTATCTGGACAAATAGTAGAAGGAACAGACTC

CTTCAAAGTGACTACATGAACATGACTCCCCGGAGGCCTGGGCTCACT

CGAAAGCCTTACCAGCCCTACGCCCCTGCCAGAGACTTTGCAGCGTAC

CGCCCCAGAGCAAAATTCAGCAGGAGTGCAGAGACTGCTGCCAACCTG

CAGGACCCCAACCAGCTCTACAATGAGCTCAATCTAGGGCGAAGAGAG

GAATATGACGTCTTGGAGAAGAAGCGGGCTCGGGATCCAGAGATGGGA

GGCAAACAGCAGAGGAGGAGGAACCCCCAGGAAGGCGTATACAATGCA

CTGCAGAAAGACAAGATGGCAGAAGCCTACAGTGAGATCGGCACAAAA

GGCGAGAGGCGGAGAGGCAAGGGGCACGATGGCCTTTACCAGGGTCTC

AGCACTGCCACCAAGGACACCTATGATGCCCTGCATATGCAGACCCTG

GCCCCTCGCTGA
```

In certain embodiments, a presently disclosed CAR comprises an extracellular antigen-binding domain that binds to CD19 (e.g., human CD19), a transmembrane domain comprising a CD28 polypeptide, and an intracellular signaling domain comprising a CD3ζ polypeptide (e.g., a human CD3ζ polypeptide) and a co-stimulatory signaling region comprising a CD28 polypeptide (e.g., a human CD28 polypeptide). In certain embodiments, the CAR is designated as "ah19h28z". In certain embodiments, the CAR (e.g., ah19h28z) comprises an amino acid sequence that is at least about 85%, about 90%, about 95%, about 96%, about 97%, about 98%, about 99% or about 100% homologous to the amino acid sequence set forth in SEQ ID NO: 39, which is provided below. SEQ ID NO: 39 includes a CD8 leader sequence at amino acids 1 to 18, and is able to bind to CD19 (e.g., human CD19).

```
                                              [SEQ ID NO: 39]
MALPVTALLL  PLALLLHAEV  KLQQSGAELV  RPGSSVKISC

KASGYAFSSY  WMNWVKQRPG  QGLEWIGQIY  PGDGDTNYNG

KFKGQATLTA  DKSSSTAYMQ  LSGLTSEDSA  VYFCARKTIS

SVVDFYFDYW  GQGTTVTVSS  GGGGSGGGGS  GGGGSDIELT

QSPKFMSTSV  GDRVSVTCKA  SQNVGTNVAW  YQQKPGQSPK
```

PLIYSATYRN SGVPDRFTGS GSGTDFTLTI TNVQSKDLAD

YFCQQYNRYP YTSGGGTKLE IKRAAAIEVM YPPPYLDNEK

SNGTIIHVKG KHLCPSPLFP GPSKPFWVLV VVGGVLACYS

LLVTVAFIIF WVRSKRSRLL HSDYMNMTPR RPGPTRKHYQ

PYAPPRDFAA YRSRVKFSRS ADAPAYQQGQ NQLYNELNLG

RREEYDVLDK RRGRDPEMGG KPRRKNPQEG LYNELQKDKM

AEAYSEIGMK GERRRGKGHD GLYQGLSTAT KDTYDALHMQ

ALPPR

An exemplary nucleic acid sequence encoding the amino acid sequence of SEQ ID NO: 39 is set forth in SEQ ID NO: 40, which is provided below.

[SEQ ID NO: 40]
ATGGCTCTCCCAGTGACTGCCCTACTGCTTCCCCTAGCGCTTCTCCT

GCATGCAGAGGTGAAGCTGCAGCAGTCTGGGGCTGAGCTGGTGAGGC

CTGGGTCCTCAGTGAAGATTTCCTGCAAGGCTTCTGGCTATGCATTC

AGTAGCTACTGGATGAACTGGGTGAAGCAGAGGCCTGGACAGGGTCT

TGAGTGGATTGGACAGATTTATCCTGGAGATGGTGATACTAACTACA

ATGGAAAGTTCAAGGGTCAAGCCACACTGACTGCAGACAAATCCTCC

AGCACAGCCTACATGCAGCTCAGCGGCCTAACATCTGAGGACTCTGC

GGTCTATTTCTGTGCAAGAAAGACCATTAGTTCGGTAGTAGATTTCT

ACTTTGACTACTGGGGCCAAGGGACCACGGTCACCGTCTCCTCAGGT

GGAGGTGGATCAGGTGGAGGTGGATCTGGTGGAGGTGGATCTGACAT

TGAGCTCACCCAGTCTCCAAAATTCATGTCCACATCAGTAGGAGACA

GGGTCAGCGTCACCTGCAAGGCCAGTCAGAATGTGGGTACTAATGTA

GCCTGGTATCAACAGAAACCAGGACAATCTCCTAAACCACTGATTTA

CTCGGCAACCTACCGGAACAGTGGAGTCCCTGATCGCTTCACAGGCA

GTGGATCTGGGACAGATTTCACTCTCACCATCACTAACGTGCAGTCT

AAAGACTTGGCAGACTATTTCTGTCAACAATATAACAGGTATCCGTA

CACGTCCGGAGGGGGGACCAAGCTGGAGATCAAACGGGCGGCCGCAA

TTGAAGTTATGTATCCTCCTCCTTACCTAGACAATGAGAAGAGCAAT

GGAACCATTATCCATGTGAAAGGGAAACACCTTTGTCCAAGTCCCCT

ATTTCCCGGACCTTCTAAGCCCTTTTGGGTGCTGGTGGTGGTTGGTG

GAGTCCTGGCTTGCTATAGCTTGCTAGTAACAGTGGCCTTTATTATT

TTCTGGGTGAGGAGTAAGAGGAGCAGGCTCCTGCACAGTGACTACAT

GAACATGACTCCCCGCCGCCCCGGGCCCACCCGCAAGCATTACCAGC

CCTATGCCCCACCACGCGACTTCGCAGCCTATCGCTCCAGAGTGAAG

TTCAGCAGGAGCGCAGACGCCCCCGCGTACCAGCAGGGCCAGAACCA

GCTCTATAACGAGCTCAATCTAGGACGAAGAGAGGAGTACGATGTTT

TGGACAAGAGACGTGGCCGGGACCCTGAGATGGGGGGAAAGCCGAGA

AGGAAGAACCCTCAGGAAGGCCTGTACAATGAACTGCAGAAAGATAA

GATGGCGGAGGCCTACAGTGAGATTGGGATGAAAGGCGAGCGCCGGA

GGGGCAAGGGGCACGATGGCCTTTACCAGGGTCTCAGTACAGCCACC

AAGGACACCTACGACGCCCTTCACATGCAGGCCCTGCCCCCTCGCTAG

In certain embodiments, a presently disclosed CAR comprises an extracellular antigen-binding domain that binds to CD19 (e.g., human CD19), a transmembrane domain comprising a CD28 polypeptide, and an intracellular signaling domain comprising a CD3ζ polypeptide (e.g., a human CD3ζ polypeptide) and a co-stimulatory signaling region comprising a 4-1BB polypeptide (e.g., a human 4-1BB polypeptide). In certain embodiments, the CAR is designated as "ah19hBBz". In certain embodiments, the CAR (e.g., ah19hBBz) comprises an amino acid sequence that is at least about 85%, about 90%, about 95%, about 96%, about 97%, about 98%, about 99% or about 100% homologous to the amino acid sequence set forth in SEQ ID NO: 41, which is provided below. SEQ ID NO: 41 includes a CD8 leader sequence at amino acids 1 to 18, and is able to bind to CD19 (e.g., human CD19).

[SEQ ID NO: 41]
MALPVTALLL PLALLLHAEV KLQQSGAELV RPGSSVKISC

KASGYAFSSY WMNWVKQRPG QGLEWIGQIY PGDGDTNYNG

KFKGQATLTA DKSSSTAYMQ LSGLTSEDSA VYFCARKTIS

SVVDFYFDYW GQGTTVTVSS GGGGSGGGGS GGGGSDIELT

QSPKFMSTSV GDRVSVTCKA SQNVGTNVAW YQQKPGQSPK

PLIYSATYRN SGVPDRFTGS GSGTDFTLTI TNVQSKDLAD

YFCQQYNRYP YTSGGGTKLE IKRAAAIEVM YPPPYLDNEK

SNGTIIHVKG KHLCPSPLFP GPSKPFWVLV VVGGVLACYS

LLVTVAFIIF WVKRGRKKLL YIFKQPFMRP VQTTQEEDGC

SCRFPEEEEG GCELRVKFSR SADAPAYQQG QNQLYNELNL

GRREEYDVLD KRRGRDPEMG GKPRRKNPQE GLYNELQKDK

MAEAYSEIGM KGERRRGKGH DGLYQGLSTA TKDTYDALHM

QALPPR

An exemplary nucleic acid sequence encoding the amino acid sequence of SEQ ID NO: 41 is set forth in SEQ ID NO: 42, which is provided below.

[SEQ ID NO: 42]
ATGGCTCTCCCAGTGACTGCCCTACTGCTTCCCCTAGCGCTTCTCC

TGCATGCAGAGGTGAAGCTGCAGCAGTCTGGGGCTGAGCTGGTGAG

GCCTGGGTCCTCAGTGAAGATTTCCTGCAAGGCTTCTGGCTATGCA

TTCAGTAGCTACTGGATGAACTGGGTGAAGCAGAGGCCTGGACAGG

GTCTTGAGTGGATTGGACAGATTTATCCTGGAGATGGTGATACTAA

CTACAATGGAAAGTTCAAGGGTCAAGCCACACTGACTGCAGACAAA

TCCTCCAGCACAGCCTACATGCAGCTCAGCGGCCTAACATCTGAGG

ACTCTGCGGTCTATTTCTGTGCAAGAAAGACCATTAGTTCGGTAGT

AGATTTCTACTTTGACTACTGGGGCCAAGGGACCACGGTCACCGTC

TCCTCAGGTGGAGGTGGATCAGGTGGAGGTGGATCTGGTGGAGGTG

-continued

```
GATCTGACATTGAGCTCACCCAGTCTCCAAAATTCATGTCCACATC

AGTAGGAGACAGGGTCAGCGTCACCTGCAAGGCCAGTCAGAATGTG

GGTACTAATGTAGCCTGGTATCAACAGAAACCAGGACAATCTCCTA

AACCACTGATTTACTCGGCAACCTACCGGAACAGTGGAGTCCCTGA

TCGCTTCACAGGCAGTGGATCTGGGACAGATTTCACTCTCACCATC

ACTAACGTGCAGTCTAAAGACTTGGCAGACTATTTCTGTCAACAAT

ATAACAGGTATCCGTACACGTCCGGAGGGGGACCAAGCTGGAGAT

CAAACGGGCGGCCGCAATTGAAGTTATGTATCCTCCTCCTTACCTA

GACAATGAGAAGAGCAATGGAACCATTATCCATGTGAAAGGGAAAC

ACCTTTGTCCAAGTCCCCTATTTCCCGGACCTTCTAAGCCCTTTTG

GGTGCTGGTGGTGGTTGGTGGAGTCCTGGCTTGCTATAGCTTGCTA

GTAACAGTGGCCTTTATTATTTTCTGGGTGAAACGGGGCAGAAAGA

AACTCCTGTATATATTCAAACAACCATTTATGAGACCAGTACAAAC

TACTCAAGAGGAAGATGGCTGTAGCTGCCGATTTCCAGAAGAAGAA

GAAGGAGGATGTGAACTGAGAGTGAAGTTCAGCAGGAGCGCAGACG

CCCCCGCGTACCAGCAGGGCCAGAACCAGCTCTATAACGAGCTCAA

TCTAGGACAAGAGAGGAGTACGATGTTTTGGACAAGAGACGTGGC

CGGGACCCTGAGATGGGGGAAAGCCGAGAAGGAAGAACCCTCAGG

AAGGCCTGTACAATGAACTGCAGAAAGATAAGATGGCGGAGGCCTA

CAGTGAGATTGGGATGAAAGGCGAGCGCCGGAGGGGCAAGGGGCAC

GATGGCCTTTACCAGGGTCTCAGTACAGCCACCAAGGACACCTACG

ACGCCCTTCACATGCAGGCCCTGCCCCCTCGCTAG
```

The presently disclosed subject matter also provides a nucleic acid composition comprising a first nucleic acid sequence encoding an antigen-recognizing receptor that binds to an antigen and a second nucleic acid sequence encoding an exogenous IL-36 polypeptide.

3. Immunoresponsive Cells

The presently disclosed subject matter provides immunoresponsive cells comprising (a) an antigen-recognizing receptor (e.g., CAR or TCR) that binds to an antigen, and (b) a secretable IL-36 polypeptide. In certain embodiments, the secretable IL-36 polypeptide is an exogenous IL-36 polypeptide. In certain embodiments, the antigen-recognizing receptor is capable of activating the immunoresponsive cell. In certain embodiments, the secretable IL-36 polypeptide (e.g., exogenous IL-36 polypeptide, such as a nucleic acid encoding an IL-36 polypeptide) is capable of promoting an anti-tumor effect of the immunoresponsive cell. The immunoresponsive cells can be transduced with an antigen-recognizing receptor and an exogenous IL-36 polypeptide such that the cells co-express the antigen-recognizing receptor and the exogenous IL-36 polypeptide.

The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer (NK) cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, helper T cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells, Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected somatic or tumor cells. A patient's own T cells may be genetically modified to target specific antigens through the introduction of an antigen-recognizing receptor, e.g., a CAR or a TCR. In certain embodiments, the immunoresponsive cell is a T cell. The T cell can be a $CD4^+$ T cell or a $CD8^+$ T cell. In certain embodiments, the T cell is a $CD4^+$ T cell. In certain embodiments, the T cell is a $CD8^+$ T cell.

Natural killer (NK) cells can be lymphocytes that are part of cell-mediated immunity and act during the innate immune response. NK cells do not require prior activation in order to perform their cytotoxic effect on target cells.

Types of human lymphocytes of the presently disclosed subject matter include, without limitation, peripheral donor lymphocytes, e.g., those disclosed in Sadelain, M., et al. 2003 *Nat Rev Cancer* 3:35-45 (disclosing peripheral donor lymphocytes genetically modified to express CARs), in Morgan, R. A., et al. 2006 *Science* 314:126-129 (disclosing peripheral donor lymphocytes genetically modified to express a full-length tumor antigen-recognizing T cell receptor complex comprising the α and β heterodimer), in Panelli, M. C., et al. 2000 *J Immunol* 164:495-504; Panelli, M. C., et al. 2000 *J Immunol* 164:4382-4392 (disclosing lymphocyte cultures derived from tumor infiltrating lymphocytes (TILs) in tumor biopsies), and in Dupont, J., et al. 2005 *Cancer Res* 65:5417-5427; Papanicolaou, G. A., et al. 2003 *Blood* 102:2498-2505 (disclosing selectively in vitro-expanded antigen-specific peripheral blood leukocytes employing artificial antigen-presenting cells (AAPCs) or pulsed dendritic cells). The immunoresponsive cells (e.g., T cells) can be autologous, non-autologous (e.g., allogeneic), or derived in vitro from engineered progenitor or stem cells.

The presently disclosed immunoresponsive cells are capable of modulating the tumor microenvironment. Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory $CD4^+$ T cells (Tregs), myeloid derived suppressor cells (MDSCs), tumor associated macrophages (TAMs), immune suppressive cytokines including TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

In certain embodiments, the presently disclosed immunoresponsive cells have increased secretion of anti-tumor cytokines, including, but not limited to, IL-36, granulocyte macrophage colony-stimulating factor (GM-CSF), IFN-γ, IL-10, IL-6, IL-12, CXCL1, CCL1, IL-23, and CXCL10. In certain embodiments, the presently disclosed immunoresponsive cells have increased secretion of IL-36, GM-CSF, IFN-γ, IL-10, or a combination thereof.

Interleukin-36

Interleukin-36 cytokine family include fourIL-36a, IL-36 (3, IL-36γ, and IL-36Ra. IL-36a, IL-36(3, and IL-36γ are agonists of IL-36 receptor (IL-36R), whereas IL-36Ra is an antagonist of IL-36 receptor.

Interleukin 36 alpha (IL-36 alpha) is also known as IL36A; FIL1; FIL1E; IL1F6; IL-1F6; IL1(EPSILON); FIL1 (EPSILON). GenBank ID: 27179 (human), 54448 (mouse), 296541 (rat), 523429 (cattle), 100065063 (horse). The protein product of IL-36 alpha includes, but is not limited to, NCBI Reference Sequences NP_055255.1, XP_011509267.1, XP_005263696.1 and XP_0168592951.

Interleukin 36 beta (IL-36 beta) is also known as IL36B; FIL1; FIL1H; IL1F8; IL1H2; IL-1F8; IL-1H2; IL1-ETA; FIL1-(ETA); FILI-(ETA). GenBank ID: 27177 (human), 69677 (mouse), 362076 (rat), 100297786 (cattle), 483068 (dog), 100065096 (horse). The protein product of IL-36 beta includes, but is not limited to, NCBI Reference Sequences NP_055253.2, NP_775270.1 and XP_0115092641.

Interleukin 36 gamma (IL-36 gamma) is also known as IL36G; IL1E; IL1F9; IL1H1; IL-1F9; IL-1H1; IL1RP2; IL-1RP2. GenBank ID: 56300 (human), 215257 (mouse), 499744 (rat), 615762 (cattle), 100686137 (dog), 100065031 (horse). The protein product of IL-36 gamma includes, but is not limited to, NCBI Reference Sequences NP_001265497.1 and NP_062564.1.

Interleukin 36 receptor antagonist (IL-36RA) is also known as IL36RN, FIL1; FIL1D; IL1F5; IL1L1; PSORP; IL1HY1; IL1RP3; IL36RA; IL-36Ra; PSORS14; FIL1 (DELTA). GenBank ID: 26525 (human), 54450 (mouse), 311783 (rat), 518514 (cattle), 611869 (dog), 100065154 (horse). The protein product of Interleukin 36 antagonist includes, but is not limited to, NCBI Reference Sequences NP_036407.1 and NP_775262.1.

IL-36 alpha, IL-36 beta and IL-36 gamma cytokines are produced by neutrophil, skin cells and other cells. They function by binding to the IL-36 receptor (IL-36R) and activate downstream signaling pathways. After stimulation with IL-36 alpha, IL-36 beta or IL-36 gamma, natural killer (NK) cells and certain T cells release other cytokines, such as IFN-γ, IL-10 and GM-CSF, which can further activate other types of immunoresponsive cells. After stimulation with IL-36 alpha, IL-36 beta or IL-36 gamma, dendritic cells can release IL-6, IL-12, CXCL1, CCL1, IL-23, and CXCL10, which can further modulate other types of immunoresponsive cells In certain embodiments, the term "IL-36" or "IL-36 cytokine" refers to the bioactive form of IL-36 alpha, IL-36 beta and/or IL-36 gamma after secretion from a cell (e.g., a form where the signal peptide is cleaved off).

In certain embodiments, the IL-36 polypeptide is a human IL-36 polypeptide.

In certain embodiments, a human IL-36 alpha polypeptide comprises or has the amino acid sequence set forth in SEQ ID NO: 4, which is provided below. In certain embodiments, a human IL-36 alpha polypeptide comprises or has an amino acid sequence that is at least about 80%, at least about 85%, at least about 90%, at least about 95%, at least about 99%, or at least about 100% homologous or identical to the sequence set forth in SEQ ID NO: 4.

```
(SEQ ID NO: 4)
KIDTPQQGSIQDINHRVWVLQDQTLIAVPRKDRMSPVTIALISCRH

VETLEKDRGNPIYLGLNGLNLCLMCAKVGDQPTLQLKEKDIMDLYN

QPEPVKSFLEYHSQSGRNSTFESVAFPGWFIAVSSEGGCPLILTQE

LGKANTIDEGLTMLF
```

In certain embodiments, a human IL-36 beta polypeptide comprises or has the amino acid sequence set forth in SEQ ID NO: 20, which is provided below. In certain embodiments, a human IL-36 beta polypeptide comprises or has an amino acid sequence that is at least about 80%, at least about 85%, at least about 90%, at least about 95%, at least about 99%, or at least about 100% homologous or identical to the sequence set forth in SEQ ID NO: 20.

```
(SEQ ID NO: 20)
REAAPKSYAIRDSRQMVWVLSGNSLIAAPLSRSIKPVILHLIACRD

TEFSDKEKGNMVYLGIKGKDLCLFCAEIQGKPTLQLKLQGSQDNIG

KDTCWKLVGIHTCINLDVRESCFMGTLDQWGIGVGRKKWKSSFQHH

HLRKKDKDESSMRTNIGMPGRM
```

In certain embodiments, a human IL-36 gamma polypeptide comprises or has the following amino acid sequence set forth in SEQ ID NO: 21, which is provided below. In certain embodiments, a human IL-36 gamma polypeptide comprises or has an amino acid sequence that is at least about 80%, at least about 85%, at least about 90%, at least about 95%, at least about 99%, or at least about 100% homologous or identical to the sequence set forth in SEQ ID NO: 21.

```
[SEQ ID NO: 21]
SMCKPITGTINDLNQQVWTLQGQNLVAVPRSDSVTPVTVAVITCKY

PEALEQGRGDPIYLGIQNPEMCLYCEKVGEQPTLQLKEQKIMDLYG

QPEPVKPFLFYRAKTGRTSTLESVAFPDWFIASSKRDQPIILTSEL

GKSYNTAFELNIND
```

In certain embodiments, the IL-36 polypeptide is a murine IL-36 polypeptide.

In certain embodiments, a murine IL-36 alpha polypeptide comprises or has the amino acid sequence set forth in SEQ ID NO: 30, which is provided below. In certain embodiments, a murine IL-36 alpha polypeptide comprises or has an amino acid sequence that is at least about 80%, at least about 85%, at least about 90%, at least about 95%, at least about 99%, or at least about 100% homologous or identical to the sequence set forth in SEQ ID NO: 30.

```
[SEQ ID NO: 30]
GRETPDFGEVFDLDQQVWIFRNQALVTVPRSHRVTPVSVTILPCKYP

ESLEQDKGIATYLGIQNPDKCLFCKEVNGHPTLLLKEEKILDLYHHP

EPMKPFLFYHTRTGGTSTFESVAFPGHYIASSKTGNPIFLTSKKGEY

YNINFNLDIKS
```

In certain embodiments, a murine IL-36 beta polypeptide comprises or has the amino acid sequence set forth in SEQ ID NO: 31, which is provided below. In certain embodiments, a murine IL-36 beta polypeptide comprises or has an amino acid sequence that is at least about 80%, at least about 85%, at least about 90%, at least about 95%, at least about 99%, or at least about 100% homologous or identical to the sequence set forth in SEQ ID NO: 31.

[SEQ ID NO: 31]
SSQSPRNYRVHDSQQMVWVLTGNTLTAVPASNNVKPVILSLIACRDTE

FQDVKKGNLVFLGIKNRNLCFCCVEMEGKPTLQLKEVDIMNLYKERKA

QKAFLEYHGIEGSTSVFQSVLYPGWFIATSSIERQTIILTHQRGKLVN

TNFYIESEK

In certain embodiments, a murine IL-36 gamma polypeptide comprises or has the amino acid sequence set forth in SEQ ID NO: 32, which is provided below. In certain embodiments, a murine IL-36 gamma polypeptide comprises or has an amino acid sequence that is at least about 80%, at least about 85%, at least about 90%, at least about 95%, at least about 99%, or at least about 100% homologous or identical to the sequence set forth in SEQ ID NO: 32.

[SEQ ID NO: 32]
GRETPDFGEVEDLDQQVWIFRNQALVTVPRSHRVTPVSVTILPCKYPE

SLEQDKGIAIYLGIQNPDKCLFCKEVNGHPTLLLKEEKILDLYHHPEP

MKPFLFYHTRTGGTSTFESVAFPGHYIASSKTGNPIFLTSKKGEYYNI

NFNLDIKS

In certain embodiments, the term "IL-36" or "IL-36 cytokine" refers to the bioactive form of IL-36 RA after secretion from a cell (e.g., a form where the signal peptide has been cleaved off).

In certain embodiments, a secretable IL-36 polypeptide refers to a polypeptide or a protein, the cytokine portion of which has at least about 80%, at least about 85%, about 90%, about 95%, about 96%, about 97%, about 98%, about 99%, or about 100% homologous to the cytokine portion of the protein product of IL-36 alpha (GenBank ID: 27179 (human), 54448 (mouse), 296541 (rat), 523429 (cattle), 100065063 (horse)), IL-36 beta (GenBank ID: 27177 (human), 69677 (mouse), 362076 (rat), 100297786 (cattle), 483068 (dog), 100065096 (horse)), IL-36 gamma (GenBank ID: 56300 (human), 215257 (mouse), 499744 (rat), 615762 (cattle), 100686137 (dog), 100065031 (horse)), or a fragment thereof that has immunostimulatory activity. In certain non-limiting embodiments, the secretable IL-36 polypeptide comprises a cytokine portion and a signal peptide, optionally joined by a linker peptide. Non-limiting examples of secretable IL-36 polypeptides include NCBI Reference Sequences NP_055255.1, XP_011509267.1, XP_005263696.1, XP_016859295.1, NP_055253.2, NP_775270.1, XP_011509264.1, NP_001265497.1 and NP_062564.1.

In certain non-limiting embodiments, the secretable IL-36 polypeptide comprises a signal peptide, for example, an IL-2 signal peptide, a kappa leader sequence, a CD8 leader sequence or a peptide with essentially equivalent activity. In certain embodiments, the secretable IL-36 polypeptide comprises an IL-2 signal peptide. In certain embodiments, the IL-2 signal peptide comprises or has the amino acid sequence set forth in SEQ ID NO: 8

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. mAbs are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. In certain embodiments, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). In certain embodiments, the cells are collected in a medium comprising 2% fetal calf serum (FCS) or 0.2% bovine serum albumin (BSA) or any other suitable, e.g., sterile, isotonic medium.

4. Vectors

Genetic modification of an immunoresponsive cell (e.g., a T cell or a NK cell) can be accomplished by transducing a substantially homogeneous cell composition with a recombinant DNA construct. In certain embodiments, a retroviral vector (either gamma-retroviral or lentiviral) is employed for the introduction of the DNA construct into the cell. For example, a polynucleotide encoding an antigen-recognizing receptor can be cloned into a retroviral vector and expression can be driven from its endogenous promoter, from the retroviral long terminal repeat, or from a promoter specific for a target cell type of interest. Non-viral vectors may be used as well.

For initial genetic modification of an immunoresponsive cell to include an antigen recognizing receptor (e.g., a CAR or TCR), a retroviral vector is generally employed for transduction, however any other suitable viral vector or non-viral delivery system can be used. The antigen-recognizing receptor and the IL-36 polypeptide can be constructed in a single, multicistronic expression cassette, in multiple expression cassettes of a single vector, or in multiple vectors. Examples of elements that create polycistronic expression cassette include, but is not limited to, various viral and non-viral Internal Ribosome Entry Sites (IRES, e.g., FGF-1 IRES, FGF-2 IRES, VEGF IRES, IGF-II IRES, NF-κB IRES, RUNX1 IRES, p53 IRES, hepatitis A IRES, hepatitis C IRES, pestivirus IRES, aphthovirus IRES, picornavirus IRES, poliovirus IRES and encephalomyocarditis virus IRES) and cleavable linkers (e.g., 2A peptides, e.g., P2A, T2A, E2A and F2A peptides). Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudo-typed with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992)$_1$ *Clin. Invest.* 89:1817.

Other transducing viral vectors can be used to modify an immunoresponsive cell. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for genetic modification of an immunoresponsive cell. For example, a nucleic acid molecule can be introduced into an immunoresponsive cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases, CRISPR). Transient expression may be obtained by RNA electroporation.

Clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9), and an optional section of DNA repair template (DNA that guides the cellular repair process allowing insertion of a specific DNA sequence). CRISPR/Cas9 often employs a plasmid to transfect the target cells. The crRNA needs to be designed for each application as this is the sequence that Cas9 uses to identify and directly bind to the target DNA in a cell. The repair template carrying CAR expression cassette need also be designed for each application, as it must overlap with the sequences on either side of the cut and code for the insertion sequence. Multiple crRNA's and the tracrRNA can be packaged together to form a single-guide RNA (sgRNA). This sgRNA can be joined together with the Cas9 gene and made into a plasmid in order to be transfected into cells.

A zinc-finger nuclease (ZFN) is an artificial restriction enzyme, which is generated by combining a zinc finger DNA-binding domain with a DNA-cleavage domain. A zinc finger domain can be engineered to target specific DNA sequences which allows a zinc-finger nuclease to target desired sequences within genomes. The DNA-binding domains of individual ZFNs typically contain a plurality of individual zinc finger repeats and can each recognize a plurality of basepairs. The most common method to generate new zinc-finger domain is to combine smaller zinc-finger "modules" of known specificity. The most common cleavage domain in ZFNs is the non-specific cleavage domain from the type IIs restriction endonuclease FokI. Using the endogenous homologous recombination (HR) machinery and a homologous DNA template carrying CAR expression cassette, ZFNs can be used to insert the CAR expression cassette into genome. When the targeted sequence is cleaved by ZFNs, the HR machinery searches for homology between the damaged chromosome and the homologous DNA template, and then copies the sequence of the template between the two broken ends of the chromosome, whereby the homologous DNA template is integrated into the genome.

Transcription activator-like effector nucleases (TALEN) are restriction enzymes that can be engineered to cut specific sequences of DNA. TALEN system operates on almost the same principle as ZFNs. They are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome.cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

5. Enhancing Endogenous IL-36 Gene Expression

Any targeted genome editing methods can be used to modify the promoter/enhancer region of an IL-36 gene locus, and thereby enhancing the endogenous expression of IL-36 in an immunoresponsive cell. In certain embodiments, the modification comprises replacement of an endogenous promoter with a constitutive promoter or an inducible promoter, or insertion of a constitutive promoter or inducible promoter to the promoter region of an IL-36 gene locus. In certain embodiments, a constitutive promoter is positioned on an IL-36 gene locus to drive gene expression of the endogenous IL-36 gene. Eligible constitutive promoters include, but are not limited to, a CMV promoter, an EF1a promoter, a SV40 promoter, a PGK1 promoter, a Ubc promoter, a beta-actin promoter, and a CAG promoter. Alternatively or additionally, a conditional or inducable promoter is positioned on an IL-36 gene locus to drive gene expression of the endogenous IL-36 gene. Non-limiting examples of conditional promoters include a tetracycline response element (TRE) promoter and an estrogen response element (ERE) promoter. In addition, enhancer elements can be placed in regions other than the promoter region.

6. Genome Editing Methods

Any targeted genome editing methods can be used to modify the promoter/enhancer region of an IL-36 gene locus. In certain embodiments, a CRISPR system is used to modify the promoter/enhancer region of an IL-36 gene locus. In certain embodiments, zinc-finger nucleases are used to modify the promoter/enhancer region of an IL-36 gene locus. In certain embodiments, a TALEN system is used to modify the promoter/enhancer region of an IL-36 gene locus.

Methods for delivering the genome editing agents/systems can vary depending on the need. In certain embodiments, the components of a selected genome editing method are delivered as DNA constructs in one or more plasmids. In certain embodiments, the components are delivered via viral vectors. Common delivery methods include but is not limited to, electroporation, microinjection, gene gun, impalefection, hydrostatic pressure, continuous infusion, sonication, magnetofection, adeno-associated viruses, envelope protein pseudotyping of viral vectors, replication-competent vectors cis and trans-acting elements, herpes simplex virus, and chemical vehicles (e.g., oligonucleotides, lipoplexes, polymersomes, polyplexes, dendrimers, inorganic Nanoparticles, and cell-penetrating peptides).

Modification can be made anywhere within an IL-36 gene locus, or anywhere that can impact gene expression of an IL-36 gene. In certain embodiments, the modification occurs upstream of the transcriptional start site of an IL-36 gene. In certain embodiments, the modification occurs between the transcriptional start site and the protein coding region of an IL-36 gene. In certain embodiments, the modification occurs downstream of the protein coding region of an IL-36 gene. In certain embodiments, the modification occurs upstream of the transcriptional start site of an IL-36 gene, wherein the modification produces a new transcriptional start site.

7. Polypeptides and Analogs

Also included in the presently disclosed subject matter are a CD19, CD28, CD3ζ, and IL-36 polypeptides or fragments thereof that are modified in ways that enhance their anti-neoplastic activity when expressed in an immunoresponsive cell. The presently disclosed subject matter provides methods for optimizing an amino acid sequence or nucleic acid sequence by producing an alteration in the sequence. Such alterations may include certain mutations, deletions, insertions, or post-translational modifications. The presently disclosed subject matter further includes analogs of any naturally-occurring polypeptide disclosed herein (including, but not limited to, CD19, CD28, CD3ζ, and IL-36). Analogs can differ from a naturally-occurring polypeptide disclosed herein by amino acid sequence differences, by post-translational modifications, or by both. Analogs can exhibit at least about 85%, about 90%, about 91%, about 92%, about 93%, about 94%, about 95%, about 96%, about 97%, about 98%, about 99% or more homologous to all or part of a naturally-occurring amino, acid sequence of the presently disclosed subject matter. The length of sequence comparison is at least 5, 10, 15 or 20 amino acid residues, e.g., at least 25, 50, or 75 amino acid residues, or more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amina acids, e.g., D-amino acids or non-naturally occurring or synthetic amino acids, e.g., β or γ amino acids.

In addition to full-length polypeptides, the presently disclosed subject matter also provides fragments of any one of the polypeptides or peptide domains disclosed herein. As used herein, the term "a fragment" means at least 5, 10, 13, or 15 amino acids. In certain embodiments, a fragment comprises at least 20 contiguous amino acids, at least 30 contiguous amino acids, or at least 50 contiguous amino acids. In certain embodiments, a fragment comprises at least 60 to 80, 100, 200, 300 or more contiguous amino acids. Fragments can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein disclosed herein (e.g., IL-36). Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. In certain embodiments, the protein analogs are relatively resistant to in vivo degradation, resulting in a more prolonged therapeutic effect upon administration. Assays for measuring functional activity include, but are not limited to, those described in the Examples below.

8. Administration

Compositions comprising the presently disclosed immunoresponsive cells can be provided systemically or directly to a subject for inducing and/or enhancing an immune response to an antigen and/or treating and/or preventing a neoplasm, pathogen infection, or infectious disease. In certain embodiments, the presently disclosed immunoresponsive cells or compositions comprising thereof are directly injected into an organ of interest (e.g., an organ affected by a neoplasm). Alternatively, the presently disclosed immunoresponsive cells or compositions comprising thereof are provided indirectly to the organ of interest, for example, by administration into the circulatory system (e.g., the tumor vasculature). Expansion and differentiation agents can be provided prior to, during or after administration of the cells or compositions to increase production of T cells, NK cells, or CTL cells in vitro or in vivo.

The presently disclosed immunoresponsive cells can be administered in any physiologically acceptable vehicle, normally intravascularly, although they may also be introduced into bone or other convenient site where the cells may find an appropriate site for regeneration and differentiation (e.g., thymus). Usually, at least about $1 \times 10^5$ cells will be administered, eventually reaching about $1 \times 10^{10}$ or more. The presently disclosed immunoresponsive cells can comprise a purified population of cells. Those skilled in the art can readily determine the percentage of the presently disclosed immunoresponsive cells in a population using various well-known methods, such as fluorescence activated cell sorting (FACS). Suitable ranges of purity in populations comprising the presently disclosed immunoresponsive cells are about 50% to about 55%, about 5% to about 60%, and about 65% to about 70%. In certain embodiments, the purity is about 70% to about 75%, about 75% to about 80%, or about 80% to about 85%. In certain embodiments, the purity is about 85% to about 90%, about 90% to about 95%, and about 95% to about 100%. Dosages can be readily adjusted by those skilled in the art (e.g., a decrease in purity may require an increase in dosage). The cells can be introduced by injection, catheter, or the like.

The presently disclosed compositions can be pharmaceutical compositions comprising the presently disclosed immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition of the presently disclosed subject matter (e.g., a pharmaceutical composition comprising a presently disclosed immunoresponsive cell), it can be formulated in a unit dosage injectable form (solution, suspension, emulsion).

9. Formulations

Compositions comprising the presently disclosed immunoresponsive cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified immunoresponsive cells in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the genetically modified immunoresponsive cells or their progenitors.

The compositions can be isotonic, i.e., they can have the same osmotic pressure as blood and lacrimal fluid. The desired isotonicity of the compositions may be accomplished using sodium chloride, or other pharmaceutically acceptable agents such as dextrose, boric acid, sodium tartrate, propylene glycol or other inorganic or organic solutes. Sodium chloride can be particularly for buffers containing sodium ions.

Viscosity of the compositions, if desired, can be maintained at the selected level using a pharmaceutically acceptable thickening agent. For example, methylcellulose is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

The quantity of cells to be administered will vary for the subject being treated. In a one embodiment, between about $10^4$ and about $10^{10}$, between about $10^5$ and about $10^9$, or between about $10^6$ and about $10^8$ of the presently disclosed immunoresponsive cells are administered to a human subject. More effective cells may be administered in even smaller numbers. In certain embodiments, at least about $1 \times 10^8$, about $2 \times 10^8$, about $3 \times 10^8$, about $4 \times 10^8$, or about $5 \times 10^8$ of the presently disclosed immunoresponsive cells are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods. Typically, any additives (in addition to the active cell(s) and/or agent (s)) are present in an amount of 0.001 to 50% (weight) solution in phosphate buffered saline, and the active ingredient is present in the order of micrograms to milligrams, such as about 0.0001 to about 5 wt %, about 0.0001 to about 1 wt %, about 0.0001 to about 0.05 wt % or about 0.001 to about 20 wt %, about 0.01 to about 10 wt %, or about 0.05 to about 5 wt %. For any composition to be administered to an animal or human, the followings can be determined: toxicity such as by determining the lethal dose (LD) and LD50 in a suitable animal model e.g., rodent such as mouse; the dosage of the composition(s), concentration of components therein and timing of administering the composition (s), which elicit a suitable response. Such determinations do not require undue experimentation from the knowledge of the skilled artisan, this disclosure and the documents cited herein. And, the time for sequential administrations can be ascertained without undue experimentation.

10. Methods of Treatment

The presently disclosed subject matter provides methods for inducing and/or increasing an immune response in a subject in need thereof. The presently disclosed immunoresponsive cells and compositions comprising thereof can be used for treating and/or preventing a neoplasm in a subject. The presently disclosed immunoresponsive cells and compositions comprising thereof can be used for prolonging the survival of a subject suffering from a neoplasm. The presently disclosed immunoresponsive cells and compositions comprising thereof can also be used for treating and/or preventing a pathogen infection or other infectious disease in a subject, such as an immunocompromised human subject. Such methods comprise administering the presently disclosed immunoresponsive cells in an amount effective or a composition (e.g., pharmaceutical composition) comprising thereof to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

For adoptive immunotherapy using antigen-specific T cells, cell doses in the range of about $10^6$-$10^{10}$ (e.g., about $10^9$) are typically infused. Upon administration of the presently disclosed cells into the host and subsequent differentiation, T cells are induced that are specifically directed against the specific antigen. The modified cells can be administered by any method known in the art including, but not limited to, intravenous, subcutaneous, intranodal, intratumoral, intrathecal, intrapleural, intraperitoneal and directly to the thymus.

The presently disclosed subject matter provides methods for treating and/or preventing a neoplasm in a subject. The method can comprise administering an effective amount of the presently disclosed immunoresponsive cells or a composition comprising thereof to a subject having a neoplasm.

Non-limiting examples of neoplasia include blood cancers (e.g. leukemias, lymphomas, and myelomas), ovarian cancer, breast cancer, bladder cancer, brain cancer, colon cancer, intestinal cancer, liver cancer, lung cancer, pancreatic cancer, prostate cancer, skin cancer, stomach cancer, glioblastoma, throat cancer, melanoma, neuroblastoma, adenocarcinoma, glioma, soft tissue sarcoma, and various carcinomas (including prostate and small cell lung cancer). Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolar carcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas. In certain embodiments, the neoplasm is selected from the group consisting of blood cancers (e.g. leukemias, lymphomas, and myelomas), ovarian cancer, prostate cancer, breast cancer, bladder cancer, brain cancer, colon cancer, intestinal cancer, liver cancer, lung cancer, pancreatic cancer, prostate cancer, skin cancer, stomach cancer, glioblastoma, and throat cancer. In certain embodiments, the presently disclosed immunoresponsive cells and compositions comprising thereof can be used for treating and/or preventing blood cancers (e.g., leukemias, lymphomas, and myelomas) or ovarian cancer, which are not amenable to conventional therapeutic interventions.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition is administered to these subjects to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of neoplasm, but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor has invaded neighboring tissues, or who show involvement of lymph nodes.

Another group have a genetic predisposition to neoplasia but have not yet evidenced clinical signs of neoplasia. For instance, women testing positive for a genetic mutation associated with breast cancer, but still of childbearing age, can wish to receive one or more of the immunoresponsive cells described herein in treatment prophylactically to prevent the occurrence of neoplasia until it is suitable to perform preventive surgery.

As a consequence of surface expression of an antigen-recognizing receptor that binds to a tumor antigen and a secretable IL-36 polypeptide (e.g., an exogenous IL-36 polypeptide) that enhances the anti-tumor effect of the immunoresponsive cell, adoptively transferred T or NK cells are endowed with augmented and selective cytolytic activity at the tumor site. Furthermore, subsequent to their localization to tumor or viral infection and their proliferation, the T cells turn the tumor or viral infection site into a highly conductive environment for a wide range of immune cells involved in the physiological anti-tumor or antiviral response (tumor infiltrating lymphocytes, NK-, NKT-cells, dendritic cells, and macrophages).

Additionally, the presently disclosed subject matter provides methods for treating and/or preventing a pathogen infection (e.g., viral infection, bacterial infection, fungal infection, parasite infection, or protozoal infection) in a subject, e.g., in an immunocompromised subject. The method can comprise administering an effective amount of the presently disclosed immunoresponsive cells or a composition comprising thereof to a subject having a pathogen infection. Exemplary viral infections susceptible to treatment include, but are not limited to, Cytomegalovirus (CMV), Epstein Barr Virus (EBV), Human Immunodeficiency Virus (HIV), and influenza virus infections.

Further modification can be introduced to the presently disclosed immunoresponsive cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the presently disclosed immunoresponsive cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). EGFRt can be covalently joined to the upstream of the antigen-recognizing receptor of a presently disclosed CAR. The suicide gene can be included within the vector comprising nucleic acids encoding a presently disclosed CAR. In this way, administration of a prodrug designed to activate the suicide gene (e.g., a prodrug (e.g., AP1903 that can activate iCasp-9) during malignant T-cell transformation (e.g., GVHD) triggers apoptosis in the suicide gene-activated CAR-expressing T cells. The incorporation of a suicide gene into the a presently disclosed CAR gives an added level of safety with the ability to eliminate the majority of CAR T cells within a very short time period. A presently disclosed immunoresponsive cell (e.g., a T cell) incorporated with a suicide gene can be pre-emptively eliminated at a given timepoint post CAR T cell infusion, or eradicated at the earliest signs of toxicity.

11. Kits

The presently disclosed subject matter provides kits for inducing and/or enhancing an immune response and/or treating and/or preventing a neoplasm or a pathogen infection in a subject. In certain embodiments, the kit comprises an effective amount of presently disclosed immunoresponsive cells or a pharmaceutical composition comprising thereof. In certain embodiments, the kit comprises a sterile container; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In certain non-limiting embodiments, the kit includes an isolated nucleic acid molecule encoding an antigen-recognizing receptor (e.g., a CAR or a TCR) directed toward an antigen of interest and an isolated nucleic acid molecule encoding an IL-36 polypeptide in expressible (and secretable) form, which may optionally be comprised in the same or different vectors.

If desired, the immunoresponsive cells and/or nucleic acid molecules are provided together with instructions for administering the cells or nucleic acid molecules to a subject having or at risk of developing a neoplasm or pathogen or immune disorder. The instructions generally include information about the use of the composition for the treatment and/or prevention of a neoplasm or a pathogen infection. In certain embodiments, the instructions include at least one of the following: description of the therapeutic agent; dosage schedule and administration for treatment or prevention of a neoplasm, pathogen infection, or immune disorder or symptoms thereof; precautions; warnings; indications; counter-indications; over-dosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides disclosed herein, and, as such, may be considered in making and practicing the presently disclosed subject matter. Particularly useful techniques for particular embodiments will be discussed in the sections that follow.

The following examples are put forth so as to provide those of ordinary skill in the art with a complete disclosure and description of how to make and use the presently disclosed cells and compositions, and are not intended to limit the scope of what the inventors regard as their invention.

Example 1—Interleukin-36 (IL-36) Secreting CAR-T Cells

Introduction

Genetically modified T cells expressing a first-generation anti-CD19 CAR and a secretable IL-36 polypeptide were generated. The IL-36-secreting CAR-T cells presented improvements when compared to a control anti-CD19 CAR-T cells that do not comprise a secretable IL-36 polypeptide. The IL-36-secreting CAR-T cells exhibited prolonged survival curves in murine models.

Results

CAR Constructs

Figure 1B:
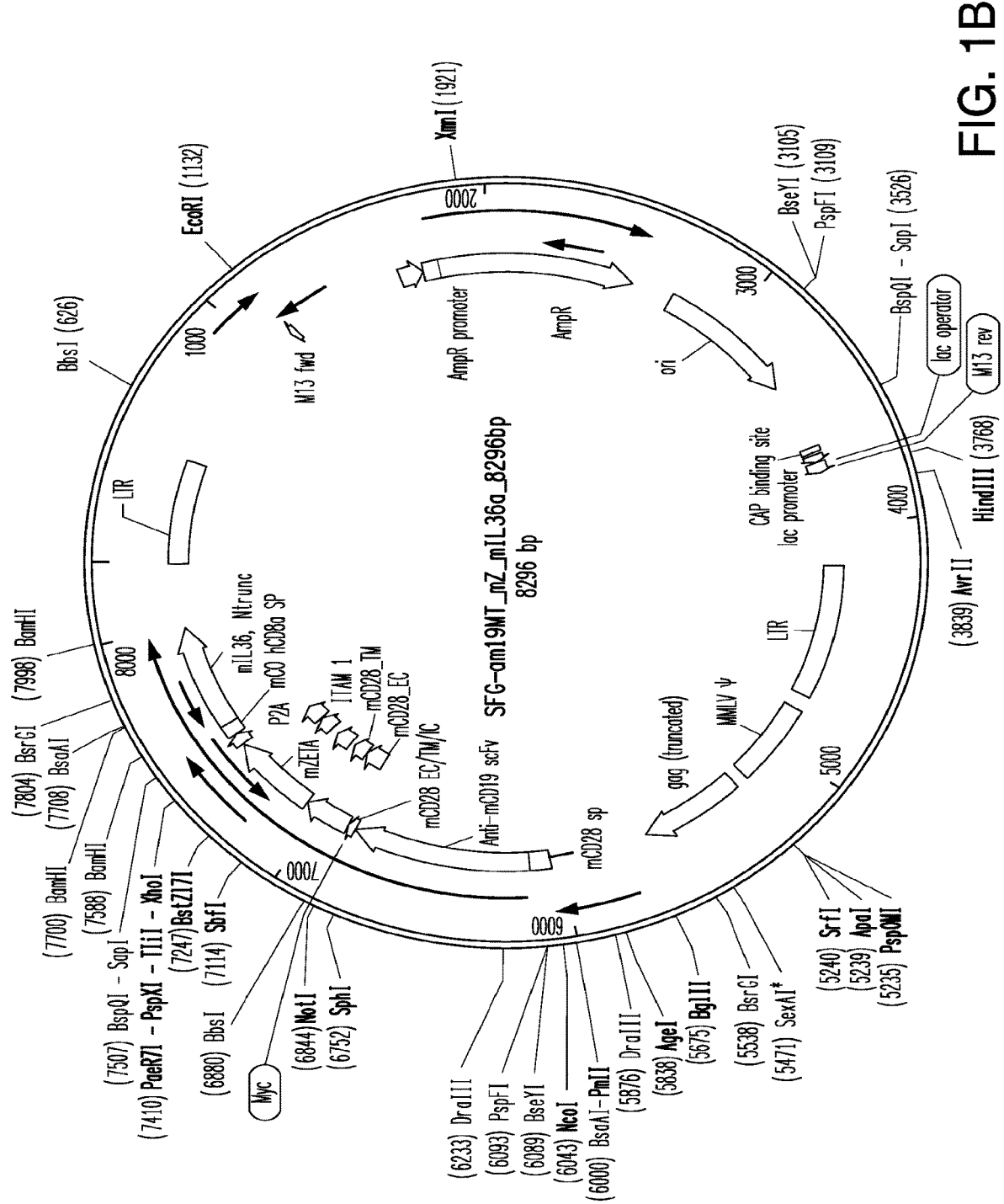
Figure 1C:
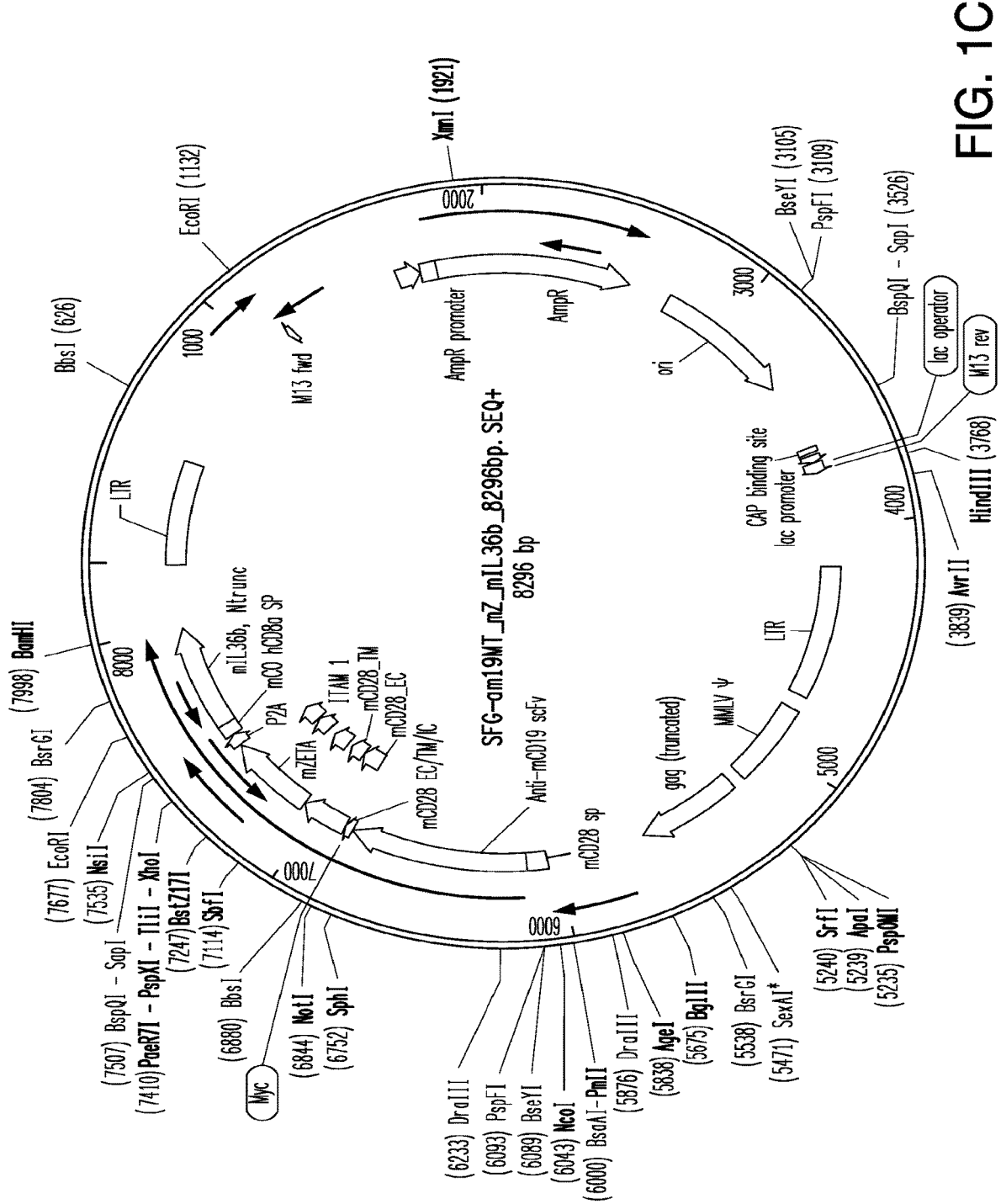
Figure 1D:
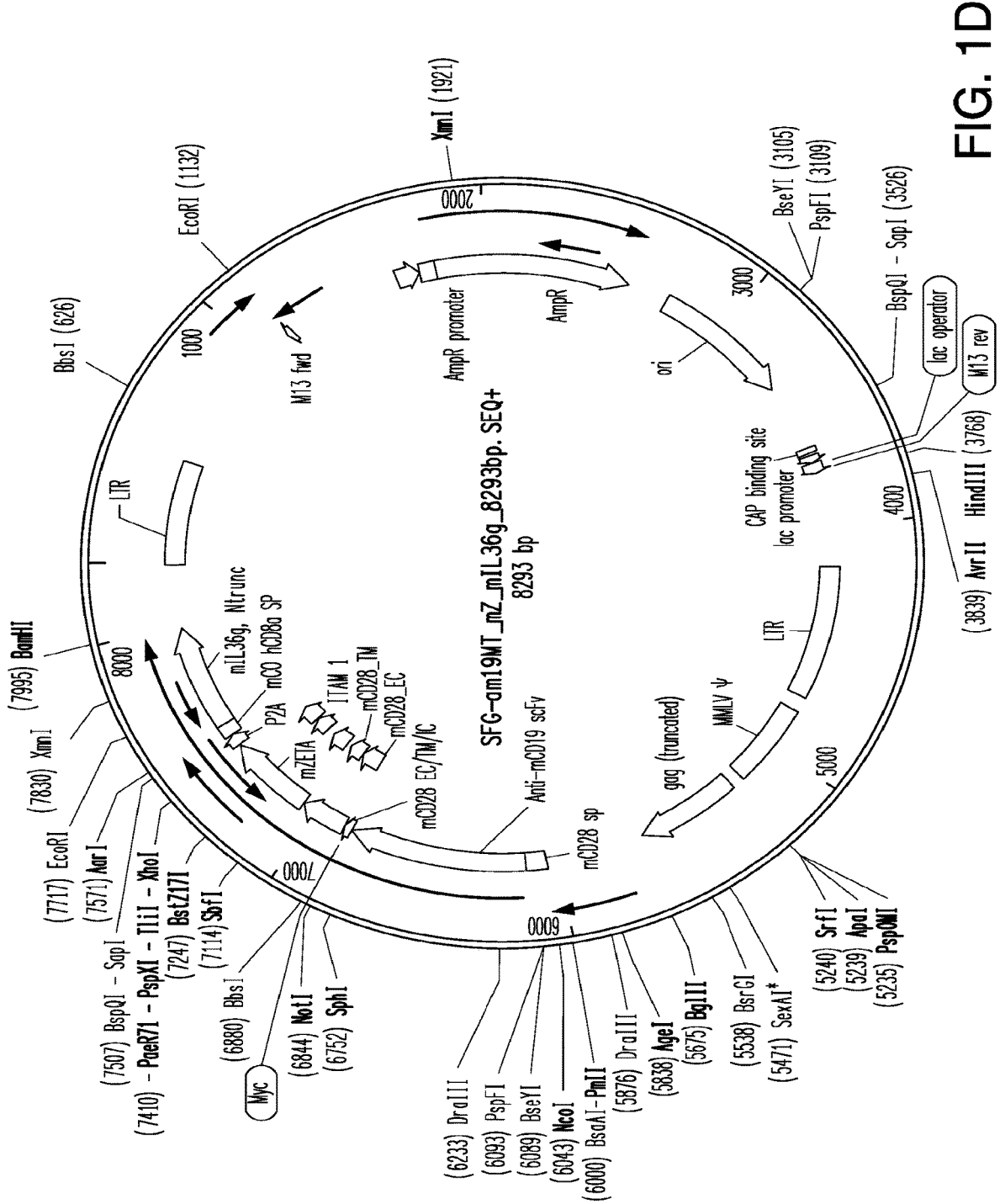

Murine anti-CD19 CAR constructs with or without a secretable murine IL-36 polypeptide were produced/constructed in SFG retroviral vector backbone e.g., am19mZ and am19mZ_IL-36, as shown in FIG. 1A. FIG. 1B shows the construct of first-generation anti-mouse CD 19 myc-tag CAR comprising a constitutively-secreted murine IL-36 alpha, wherein the murine IL-36 alpha has the amino acid sequence set forth in SEQ ID NO: 30. FIG. 1C shows the construct of first-generation anti-mouse CD 19 myc-tag CAR incorporating constitutively-secreted murine IL-36 beta, wherein the murine IL-36 alpha has the amino acid sequence set forth in SEQ ID NO: 31. FIG. 1D shows the construct of first-generation anti-mouse CD 19 myc-tag CAR incorporating constitutively-secreted murine IL-36 gamma, wherein the murine IL-36 alpha has the amino acid sequence set forth in SEQ ID NO: 32.

T cells were transduced with one of the above-noted various constructs.

Cell Surface CAR Expression

Figure 2:
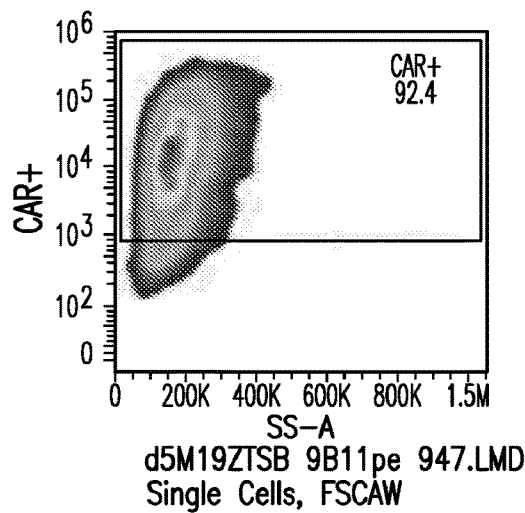
FIG. 2 depicts flow cytometry analyses of cell surface expression of various CAR constructs. Surface expressions of anti-CD19 myc-tag first generation CAR secreting IL-36 beta (d5M19ZTSB) and gamma (d5M19ZTSG) and control constructs including M19del (non-functional CAR), M19Z (first generation CAR) were confirmed. d5B6emp served as a negative control.
Figure 2:
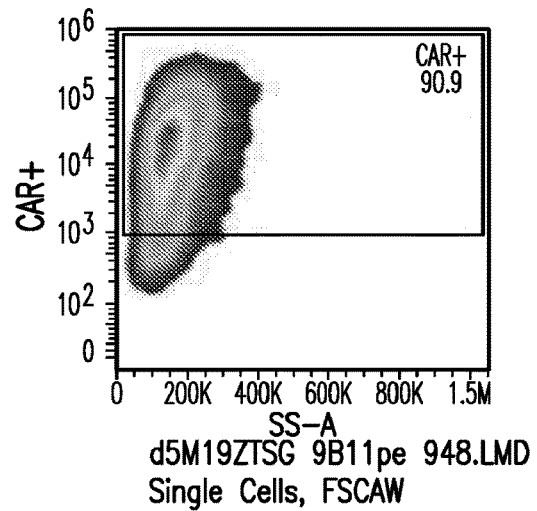
Figure 2:
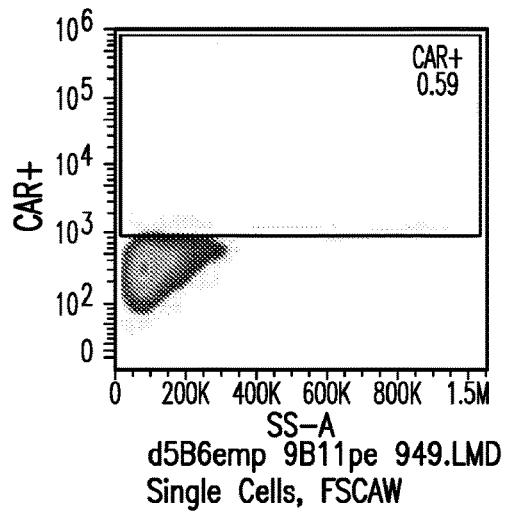
Figure 2:
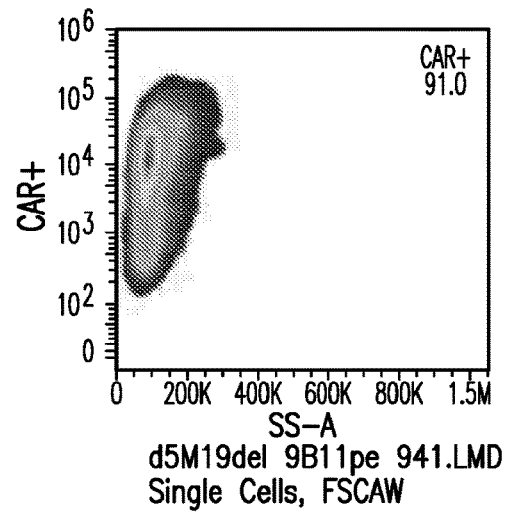
Figure 2:
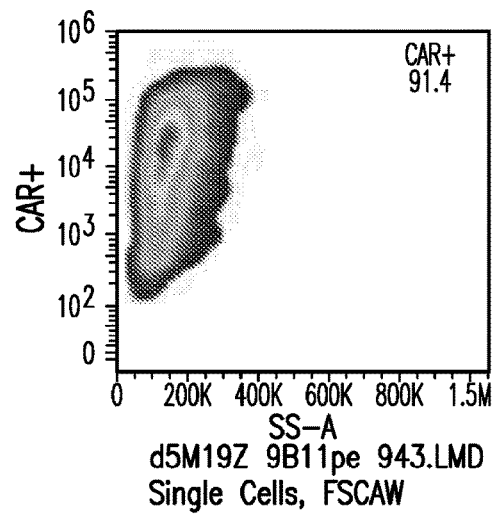

The CAR expression of these AR constructs on mouse T cells (5 days post harvesting from spleen, and 4 days post start of transduction) cell surface were confirmed via flow cytometry analyses, and the results are shown in FIG. 2. Surface expressions of anti-CD19 myc-tag first generation CAR T cells secreting IL-36 beta (d5M19ZTSB) and gamma (d5M19ZTSG) are shown in the first and the second scatter plots in row 1, respectively. d5B6emp (non-transduced C57BL/6 mouse splenocytes) served as a negative control. M19z, which refers to T cells comprising a first generation anti-CD19 CAR without a secretable IL-36 polypeptide, was used as a positive control.

Increased Cytokine Secretion

Figure 3:
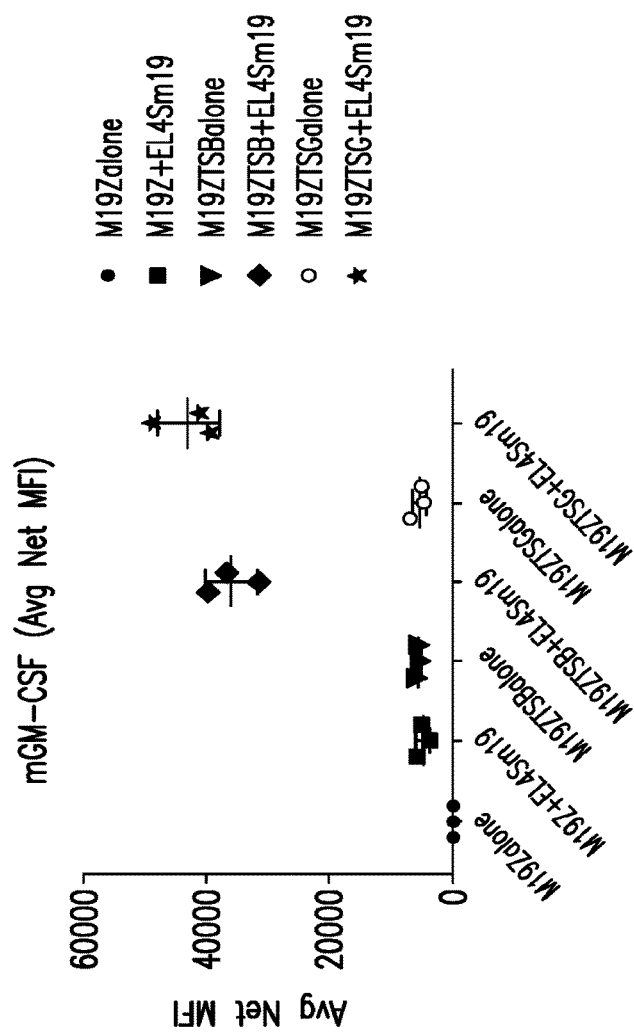
FIG. 3 depicts murine granulocyte macrophage colony-stimulating factor (GM-CSF) secretion in T cells transduced with various CAR constructs. Mean differences between indicated samples, 95% confidence interval thereof and adjusted P values are shown in the table below.

The cytokine production/secretion by the modified T cells was measured by flow cytometry. As shown in FIG. 3, the IL-36-secreting CAR-expressing T cells exhibited an increased secretion of murine GM-CSF in CD19$^+$ tumor cells (EL4Sm19) as compared to control cells, i.e., T cells expressing M19Z alone and not expressing a secretable IL-36 polypeptide.

Figure 4:
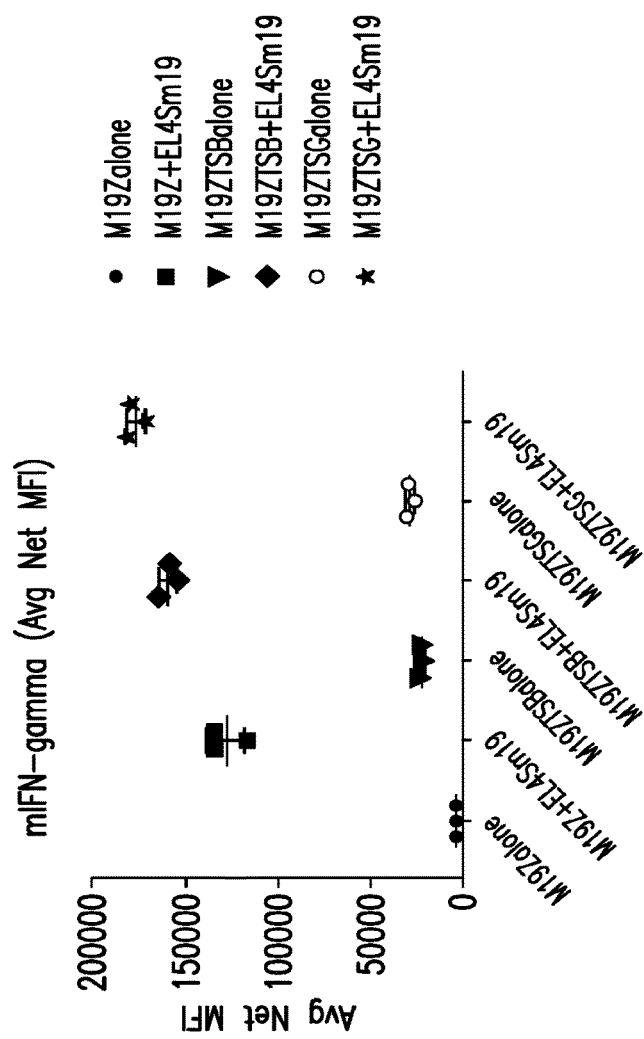
FIG. 4 depicts murine Interferon gamma (mINF-gamma) secretion in T cells transduced with various CAR constructs. Mean differences between indicated samples, 95% confidence interval thereof and adjusted P values are shown in the table below.

As shown in FIG. 4, the IL-36-secreting CAR-expressing T cells exhibited an increased secretion of murine Interferon gamma (mINF-gamma) in CD19$^+$ tumor cells (EL4Sm19) as compared to control cells, i.e., T cells expressing M19Z alone and not expressing a secretable IL-36 polypeptide.

Figure 5:
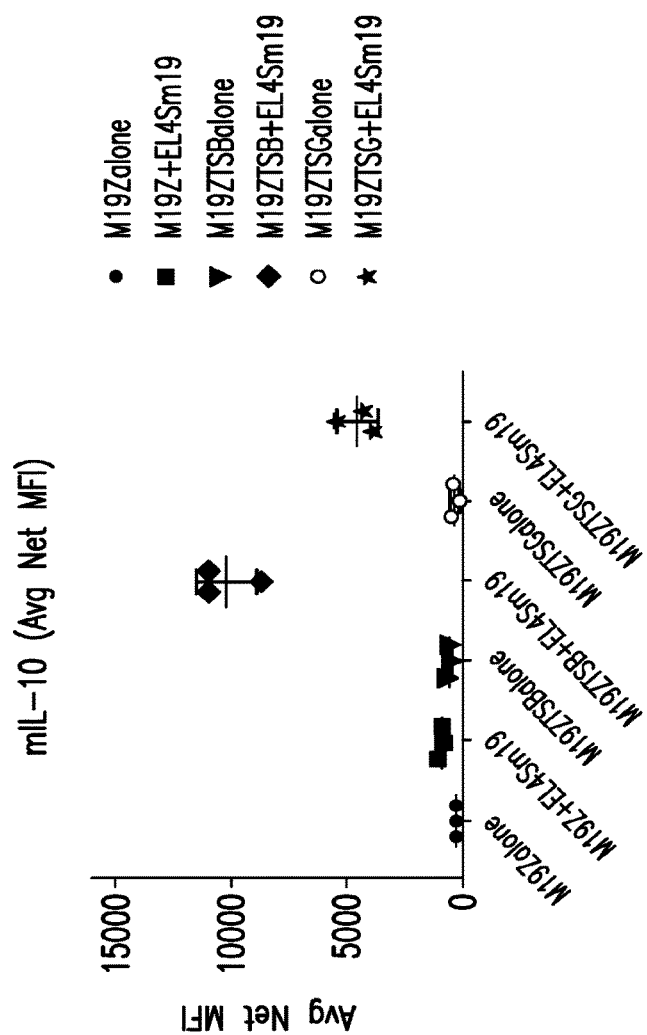
FIG. 5 depicts murine Interleukin 10 (IL-10) secretion in T cells transduced with various CAR constructs. Mean differences between indicated samples, 95% confidence interval thereof and adjusted P values are shown in the table below.

As shown in FIG. 5, the IL-36-secreting CAR-expressing T cells exhibited an increased secretion of murine Interleukin 10 (IL-10) in CD19$^+$ tumor cells (EL4Sm19) as compared to control cells, i.e., T cells expressing M19Z alone and not expressing a secretable IL-36 polypeptide.

Survival of EL4SmCD19$^+$ Tumor-Bearing Syngeneic Immuno-Competent Mice

Figure 6A:
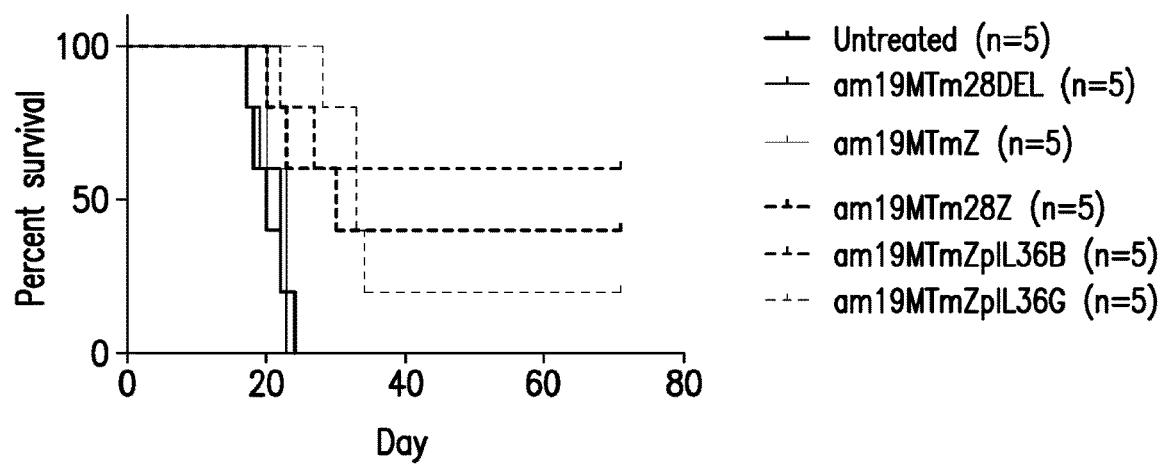
FIGS. 6A-6C depict survival curves of tumor-bearing mice treated with various modified T cells. A) Survival curves of all subjects. Untreated (untreated control group); am19MTmZ (a first generation CAR comprising a rat anti-mouse CD19 scFv and an intracellular signaling domain that comprises a mouse CD3$\zeta$ polypeptide); am19MTmZpIL36B (a first generation CAR (am19mZ) secreting murine IL-36 beta), and am19MTmZpIL36G (a first generation CAR (am19mZ) secreting murine IL-36 gamma). Median survival numbers are shown in the table below. B) Survival curves of am19MTmZ (M19Z) and am19MTmZpIL36B (M19Z_36B). Median survival numbers are shown in the table below. C) Survival curves of am19MTmZ (M19Z) and am19MTmZpIL36G (M19Z_36G). Median survival numbers are shown in the table below.
Figure 6B:
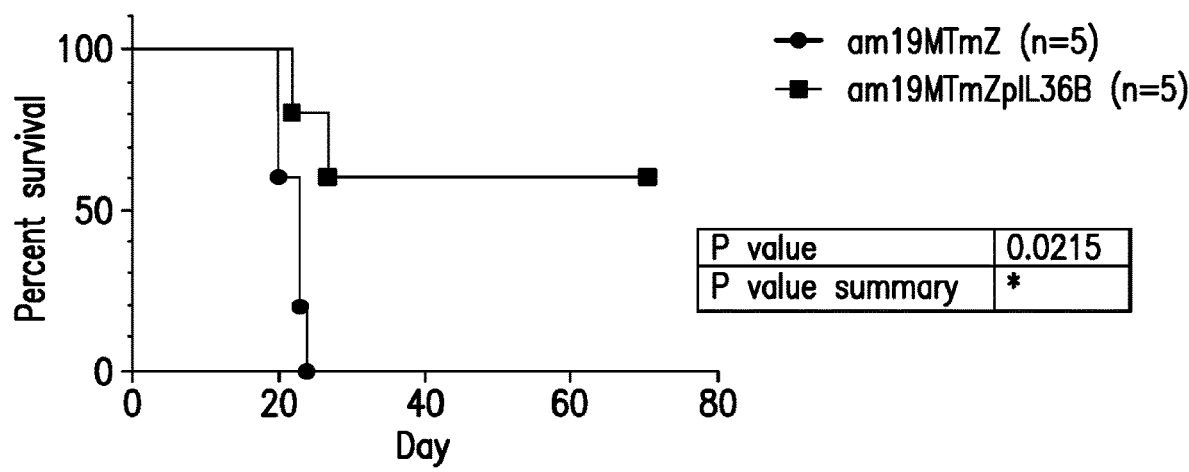
Figure 6C:
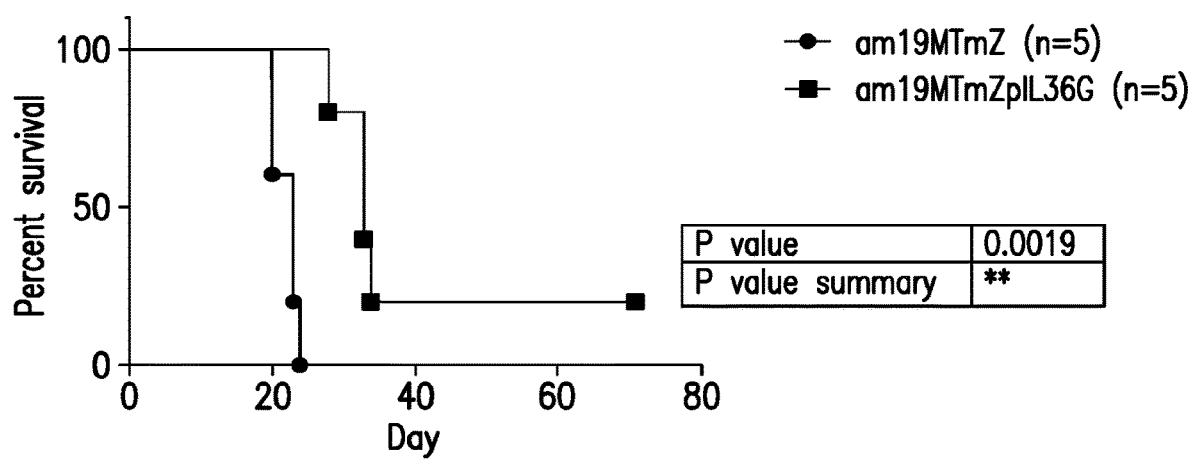

The modified T cells were studied in the context of syngeneic, immune competent models of disease wherein long-term survival of EL4SmCD19$^+$ tumor-bearing syngeneic immuno-competent mice were assessed. C57BL/8 mice were inoculated with 1×10$^6$ EL4Sm19tc (EL4 tumor cells from Sigma which ectopically expressed murine CD19). The mice were subsequently treated with 5×10$^6$ CAR T cells transduced with various CAR constructs one day after tumor inoculation, and survival was followed. Survival curves of all subjects are shown in FIG. 6. As shown in FIG. 6A, the IL-36-secreting CAR-expressing T cells (e.g., am19MTmZpIL36B and am19MTmZpIL36G) both induced long-term survival in tumor-bearing mice compared to untreated mice. Furthermore, comparison of am19MTmZ (M19Z) and am19MTmZpIL36B (M19Z_36B) (see FIG. 6B) and comparison of am19MTmZ (M19Z) and am19MTmZpIL36G (M19Z_36G) (see FIG. 6C) showed significant increase in survival of mice treated with IL36 beta and gamma secreting CAR-expressing T cells compared to CAR-T cells without IL-36 secretion.

Example 2

Syngeneic IL36-Gamma Secreting Murine CAR T Cells Improved Survival in Tumor-Bearing Mice.

Figure 7:
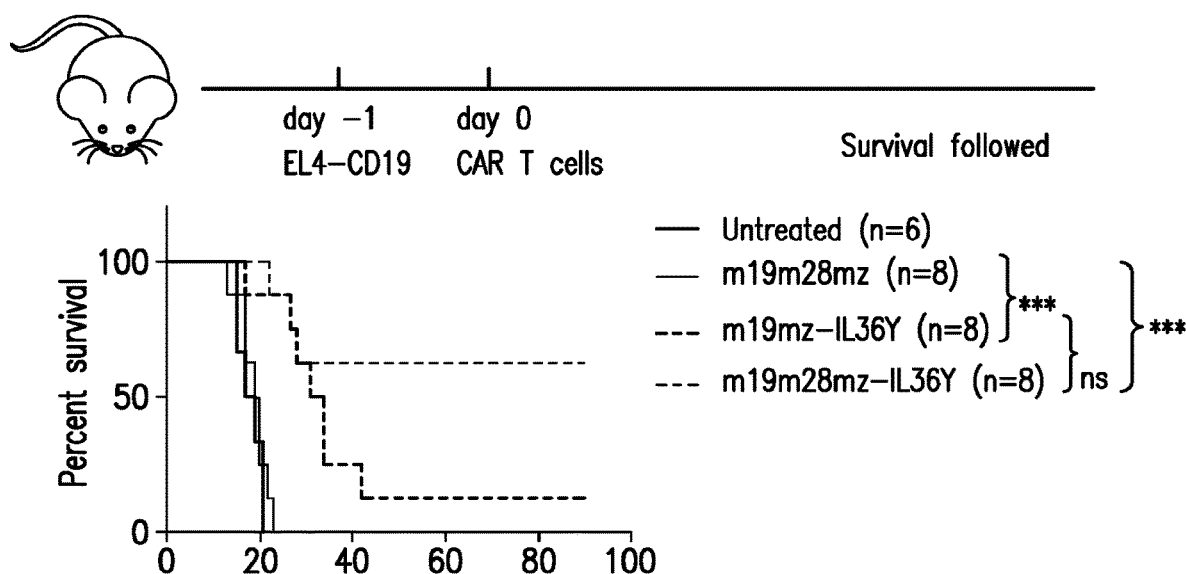
FIG. 7 depicts survival curves of C57BL/6 mice. Mice were inoculated with 1 million mouse CD19+EL4 tumor cells (EL4-CD19) via tail vein injection. On the following day, the mice received (without any pre-conditioning chemotherapy): no CAR T cells (untreated), 2,500,000 m19m28mz (syngeneic anti-mouse CD19 CD28-based second generation CAR T cells), 2,500,000 m19mz-IL36Y (syngeneic anti-mouse CD19 first-generation IL36-gamma secreting CAR T cells) or m19m28mz-IL36Y (syngeneic anti-mouse CD19 CD28-based second generation IL36-gamma secreting CAR T cells).

8-12 week-old C57BL/6 mice were inoculated with 1 million mouse CD19+EL4 tumor cells (EL4-CD19) via tail vein injection. On the following day, the mice received (without getting any pre-conditioning chemotherapy): no CAR T cells (untreated), 2,500,000 m19m28mz (syngeneic anti-mouse CD19 CD28-based second generation CAR T cells), 2,500,000 m19mz-IL36Y (syngeneic anti-mouse CD19 first-generation IL36-gamma secreting CAR T cells) or m19m28mz-IL36Y (syngeneic anti-mouse CD19 CD28-based second generation IL36-gamma secreting CAR T cells) the following day. Survival was followed as shown in FIG. 7. The results demonstrated that both first-generation and second-generation IL36-gamma secreting CAR T cells significantly improved survival and induced long-term remissions as compared to non-IL36-gamma secreting CAR T cells. These results indicated that IL36-gamma secreting CAR T cells were more potent than their non-secreting counterparts.

Syngeneic IL36-Gamma Secreting Murine CAR T Cells Elaborated Increased Pro-Inflammatory Cytokine Secretion in Tumor-Bearing Mice.

Figure 8:
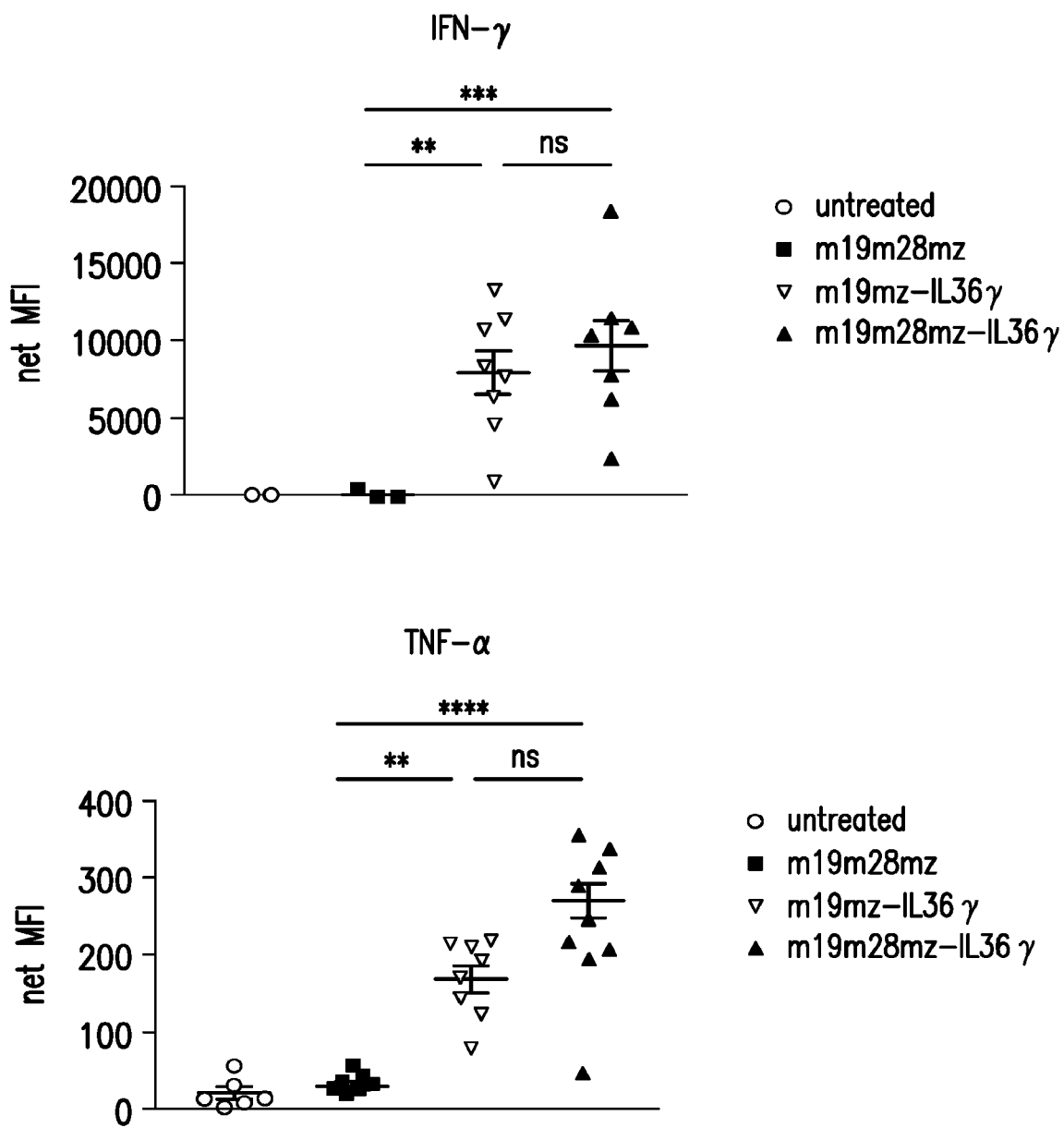
FIG. 8 depicts pro-inflammatory cytokine secretion in tumor-bearing mice. C57BL/6 mice were inoculated with 1 million mouse CD19+EL4 tumor cells (EL4-CD19) via tail vein injection. On the following day, the mice received (without getting any pre-conditioning chemotherapy): no CAR T cells (untreated), 2,500,000 m19m28mz (syngeneic anti-mouse CD19 CD28-based second generation CAR T cells), 2,500,000 m19mz-IL36Y (syngeneic anti-mouse CD19 first-generation IL36-gamma secreting CAR T cells) or m19m28mz-IL36Y (syngeneic anti-mouse CD19 CD28-based second generation IL36-gamma secreting CAR T cells). Serum was collected and analyzed for cytokine levels using a Luminex bead-based multiplex assay.

The mice treated with the CAR T cells described in this example were eye bled on day 7, and serum was collected and analyzed for cytokine levels using a Luminex bead-based multiplex assay. The results shown in FIG. 8 demonstrated that mice receiving either m19mz-IL36Y or m19m28mz-IL36Y had significantly higher serum levels of interferon gamma and TNF-alpha as compared to untreated mice or those that received the m19m28mz, indicating increased functionality of IL36-gamma secreting CAR T cells in vivo.

Syngeneic IL36-Gamma Secreting Murine CAR T Cells Induce B-Cell Aplasia in Tumor-Bearing Mice.

Figure 9:
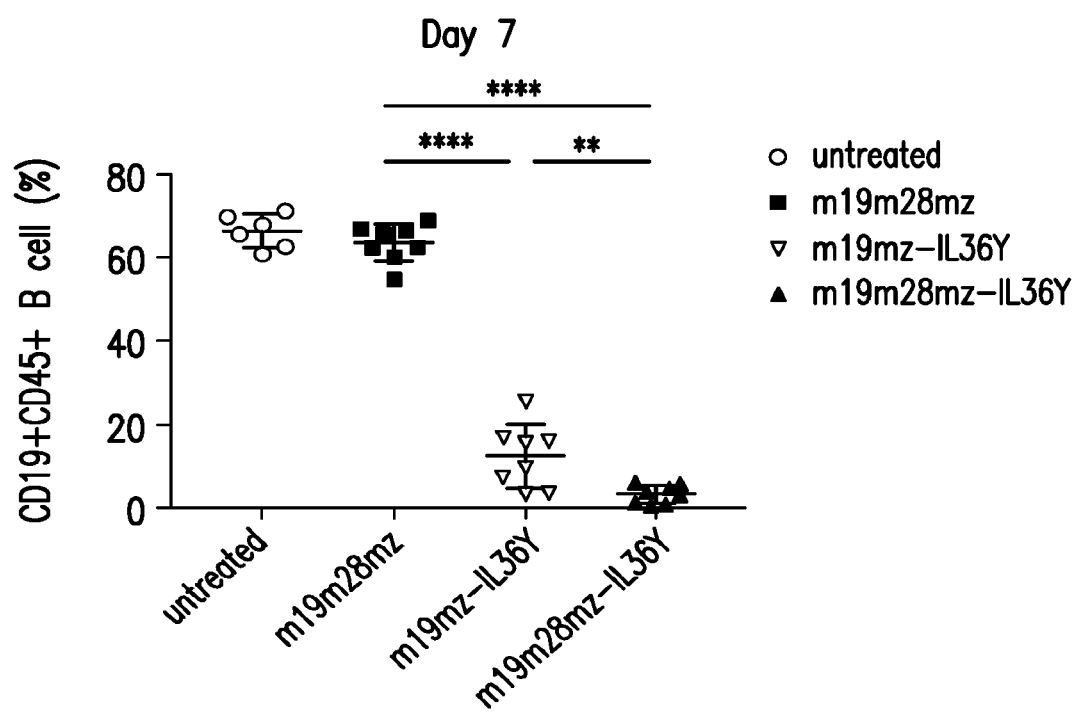
FIG. 9 depicts B cell aplasia in tumor-bearing mice. C57BL/6 mice were inoculated with 1 million mouse CD19+EL4 tumor cells (EL4-CD19) via tail vein injection. On the following day, the mice received (without getting any pre-conditioning chemotherapy): no CAR T cells (untreated), 2,500,000 m19m28mz (syngeneic anti-mouse CD19 CD28-based second generation CAR T cells), 2,500, 000 m19mz-IL36Y (syngeneic anti-mouse CD19 first-generation IL36-gamma secreting CAR T cells) or m19m28mz-IL36Y (syngeneic anti-mouse CD19 CD28-based second generation IL36-gamma secreting CART cells). Post RBC lysis, the percentage of peripheral B-cells (CD19+ cells as a percentage of CD45+ cells) was determined utilizing flow cytometry.

The mice treated with the CAR T cells described in this example were eye bled on day 7. Post RBC lysis, the percentage of peripheral B-cells (CD19+ cells as a percentage of CD45+ cells) was determined utilizing flow cytometry. As shown in FIG. 9, mice that received IL36-gamma secreting CAR T cells demonstrated significantly decreased levels of peripherally detectable B-cells as compared to untreated mice or those that received m19m28mz. The results indicated that IL36-gamma secreting CAR T cells were more potent than their non-secreting counterparts as they were able to induce deeper levels of B-cell aplasia, a surrogate marker of CART cell potency in vivo in the setting of CD19-targeted CAR T cell therapy.

Embodiments of the Presently Disclosed Subject Matter

From the foregoing description, it will be apparent that variations and modifications may be made to the presently disclosed subject matter to adopt it to various usages and conditions. Such embodiments are also within the scope of the following claims.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An immunoresponsive cell comprising:
    (a) an exogenous antigen-recognizing receptor that binds to an antigen, and
    (b) an exogenous IL-36 polypeptide or a fragment thereof.

2. The immunoresponsive cell of claim 1, wherein the antigen is a tumor antigen or a pathogen antigen, optionally wherein the antigen is a tumor antigen.

3. The immunoresponsive cell of claim 1, wherein the exogenous IL-36 polypeptide is secreted.

4. The immunoresponsive cell of claim 1, wherein said antigen-recognizing receptor is a T cell receptor (TCR) or a chimeric antigen receptor (CAR).

5. The immunoresponsive cell of claim 1, wherein the antigen-recognizing receptor and/or the exogenous IL-36 polypeptide is expressed from a vector.

6. The immunoresponsive cell of claim 1, wherein the cell is selected from the group consisting of a T cell, a Natural Killer (NK) cell, and a pluripotent stem cell from which lymphoid cells may be differentiated.

7. The immunoresponsive cell of claim 6, wherein said immunoresponsive cell is a T cell.

8. The immunoresponsive cell of claim 7, wherein said T cell is selected from the group consisting of a cytotoxic T lymphocyte (CTL), a regulatory T cell, a Natural Killer T (NKT) cell, and combinations thereof.

9. The immunoresponsive cell of claim 2, wherein the tumor antigen is selected from the group consisting of CD19, MUC16, MUC1, CAIX, CEA, CD8, CD7, CD10, CD20, CD22, CD30, CLL1, CD33, CD34, CD38, CD41, CD44, CD49f, CD56, CD74, CD133, CD138, EGP-2, EGP-40, EpCAM, Erb-B2, Erb-B3, Erb-B4, FBP, Fetal acetylcholine receptor, folate receptor-a, GD2, GD3, HER-2, hTERT, IL-13R-a2, κ-light chain, KDR, LeY, L1 cell adhesion molecule, MAGE-A1, Mesothelin, MAGEA3, p53, MART1, GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD123, CD44V6, NKCS1, EGF1R, EGFR-VIII, CD99, CD70, ADGRE2, CCR1, LILRB2, and PRAME.

10. The immunoresponsive cell of claim 9, wherein said antigen is CD19.

11. The immunoresponsive cell of claim 1, wherein said IL-36 polypeptide comprises a heterologous signal sequence at the amino-terminus.

12. The immunoresponsive cell of claim 11, wherein said heterologous signal sequence is selected from the group consisting of an IL-2 signal sequence, a kappa leader sequence, a CD8 leader sequence, and combinations thereof.

13. The immunoresponsive cell of claim 12, wherein said heterologous signal sequence is an IL-2 signal sequence.

14. The immunoresponsive cell of claim 4, wherein the antigen-recognizing receptor is a CAR.

15. The immunoresponsive cell of claim 14, wherein the CAR comprises an extracellular antigen-binding domain, a transmembrane domain, and an intracellular signaling domain.

16. The immunoresponsive cell of claim 15, wherein the intracellular signaling of the CAR does not comprise a co-stimulatory signaling region.

17. The immunoresponsive cell of claim 1, wherein the IL-36 peptide is a mature form of IL-36 alpha, IL-36 beta, IL-36 gamma, or a functional fragment thereof.

18. The immunoresponsive cell of claim 1, wherein the IL-36 peptide comprises (a) an amino acid sequence that is at least about 80% homologous or identical to the sequence set forth in SEQ ID NO: 4, SEQ ID NO: 20, SEQ ID NO: 21, SEQ ID NO: 30, SEQ ID NO: 31, or SEQ ID NO: 32; or (b) the amino acid sequence set forth in SEQ ID NO: 4, SEQ ID NO: 20, SEQ ID NO: 21, SEQ ID NO: 30, SEQ ID NO: 31, or SEQ ID NO: 32.

19. The immunoresponsive cell of claim 1, wherein the exogenous IL-36 polypeptide enhances an immune response of the immunoresponsive cell, and/or increases anti-tumor cytokine production of the immunoresponsive cell.

20. The immunoresponsive cell of claim 19, wherein the anti-tumor cytokine is selected from the group consisting of IL-10, GM-CSF, and IFN-γ.

21. A pharmaceutical composition comprising an effective amount of an immunoresponsive cell of claim 1 and a pharmaceutically acceptable excipient.

22. A method of reducing tumor burden in a subject, and/or treating and/or preventing a neoplasm in a subject, and/or lengthening survival of a subject having a neoplasm, and/or increasing immune-activating cytokine production in response to a tumor antigen or a pathogen antigen in a subject, the method comprising administering to the subject an effective amount of the immunoresponsive cells of claim 1 or a pharmaceutical composition comprising thereof.

23. The method of claim 22, wherein the subject did not receive preconditioning chemotherapy prior to the administration of the cells.

24. A kit comprising an immunoresponsive cell of claim 1.

* * * * *

SEQUENCE LISTING

<160> NUMBER OF SEQ ID NOS: 80

<210> SEQ ID NO 1
<211> LENGTH: 164
<212> TYPE: PRT
<213> ORGANISM: Homo sapiens

<400> SEQUENCE: 1

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met

```
                    115                 120                 125
Lys Gly Glu Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 2
<211> LENGTH: 220
<212> TYPE: PRT
<213> ORGANISM: Homo sapiens

<400> SEQUENCE: 2

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 3
<211> LENGTH: 255
<212> TYPE: PRT
<213> ORGANISM: Homo sapiens

<400> SEQUENCE: 3

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60
```

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 4
<211> LENGTH: 153
<212> TYPE: PRT
<213> ORGANISM: Homo sapiens

<400> SEQUENCE: 4

Lys Ile Asp Thr Pro Gln Gln Gly Ser Ile Gln Asp Ile Asn His Arg
1               5                   10                  15

Val Trp Val Leu Gln Asp Gln Thr Leu Ile Ala Val Pro Arg Lys Asp
                20                  25                  30

Arg Met Ser Pro Val Thr Ile Ala Leu Ile Ser Cys Arg His Val Glu
            35                  40                  45

Thr Leu Glu Lys Asp Arg Gly Asn Pro Ile Tyr Leu Gly Leu Asn Gly
        50                  55                  60

Leu Asn Leu Cys Leu Met Cys Ala Lys Val Gly Asp Gln Pro Thr Leu
65                  70                  75                  80

Gln Leu Lys Glu Lys Asp Ile Met Asp Leu Tyr Asn Gln Pro Glu Pro
                85                  90                  95

Val Lys Ser Phe Leu Phe Tyr His Ser Gln Ser Gly Arg Asn Ser Thr
            100                 105                 110

Phe Glu Ser Val Ala Phe Pro Gly Trp Phe Ile Ala Val Ser Ser Glu
        115                 120                 125

Gly Gly Cys Pro Leu Ile Leu Thr Gln Glu Leu Gly Lys Ala Asn Thr
130                 135                 140

Thr Asp Phe Gly Leu Thr Met Leu Phe
145                 150

<210> SEQ ID NO 5
<211> LENGTH: 455
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 5

```
Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Glu Val Gln Leu Gln
                20                  25                  30

Gln Ser Gly Ala Glu Leu Val Arg Pro Gly Thr Ser Val Lys Leu Ser
            35                  40                  45

Cys Lys Val Ser Gly Asp Thr Ile Thr Phe Tyr Tyr Met His Phe Val
50                  55                  60

Lys Gln Arg Pro Gly Gln Gly Leu Glu Trp Ile Gly Arg Ile Asp Pro
65                  70                  75                  80

Glu Asp Glu Ser Thr Lys Tyr Ser Glu Lys Phe Lys Asn Lys Ala Thr
                85                  90                  95

Leu Thr Ala Asp Thr Ser Ser Asn Thr Ala Tyr Leu Lys Leu Ser Ser
            100                 105                 110

Leu Thr Ser Glu Asp Thr Ala Thr Tyr Phe Cys Ile Tyr Gly Gly Tyr
        115                 120                 125

Tyr Phe Asp Tyr Trp Gly Gln Gly Val Met Val Thr Val Ser Ser Gly
130                 135                 140

Gly Gly Gly Ser Gly Gly Gly Gly Ser Gly Gly Gly Gly Ser Asp Ile
145                 150                 155                 160

Gln Met Thr Gln Ser Pro Ala Ser Leu Ser Thr Ser Leu Gly Glu Thr
                165                 170                 175

Val Thr Ile Gln Cys Gln Ala Ser Glu Asp Ile Tyr Ser Gly Leu Ala
            180                 185                 190

Trp Tyr Gln Gln Lys Pro Gly Lys Ser Pro Gln Leu Leu Ile Tyr Gly
        195                 200                 205

Ala Ser Asp Leu Gln Asp Gly Val Pro Ser Arg Phe Ser Gly Ser Gly
210                 215                 220

Ser Gly Thr Gln Tyr Ser Leu Lys Ile Thr Ser Met Gln Thr Glu Asp
225                 230                 235                 240

Glu Gly Val Tyr Phe Cys Gln Gln Gly Leu Thr Tyr Pro Arg Thr Phe
                245                 250                 255

Gly Gly Gly Thr Lys Leu Glu Leu Lys Arg Ala Ala Ala Glu Gln Lys
            260                 265                 270

Leu Ile Ser Glu Glu Asp Leu Ile Glu Phe Met Tyr Pro Pro Pro Tyr
        275                 280                 285

Leu Asp Asn Glu Arg Ser Asn Gly Thr Ile Ile His Ile Lys Glu Lys
290                 295                 300

His Leu Cys His Thr Gln Ser Ser Pro Lys Leu Phe Trp Ala Leu Val
305                 310                 315                 320

Val Val Ala Gly Val Leu Phe Cys Tyr Gly Leu Leu Val Thr Val Ala
                325                 330                 335

Leu Cys Val Ile Trp Thr Arg Ala Lys Phe Ser Arg Ser Ala Glu Thr
            340                 345                 350

Ala Ala Asn Leu Gln Asp Pro Asn Gln Leu Tyr Asn Glu Leu Asn Leu
        355                 360                 365

Gly Arg Arg Glu Glu Tyr Asp Val Leu Glu Lys Lys Arg Ala Arg Asp
370                 375                 380
```

```
Pro Glu Met Gly Gly Lys Gln Gln Arg Arg Arg Asn Pro Gln Glu Gly
385                 390                 395                 400

Val Tyr Asn Ala Leu Gln Lys Asp Lys Met Ala Glu Ala Tyr Ser Glu
                405                 410                 415

Ile Gly Thr Lys Gly Glu Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Thr Leu Ala Pro Arg
    450                 455

<210> SEQ ID NO 6
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Glu Val Gln Leu Gln
                20                  25                  30

Gln Ser Gly Ala Glu Leu Val Arg Pro Gly Thr Ser Val Lys Leu Ser
            35                  40                  45

Cys Lys Val Ser Gly Asp Thr Ile Thr Phe Tyr Tyr Met His Phe Val
        50                  55                  60

Lys Gln Arg Pro Gly Gln Gly Leu Glu Trp Ile Gly Arg Ile Asp Pro
65                  70                  75                  80

Glu Asp Glu Ser Thr Lys Tyr Ser Glu Lys Phe Lys Asn Lys Ala Thr
                85                  90                  95

Leu Thr Ala Asp Thr Ser Ser Asn Thr Ala Tyr Leu Lys Leu Ser Ser
            100                 105                 110

Leu Thr Ser Glu Asp Thr Ala Thr Tyr Phe Cys Ile Tyr Gly Gly Tyr
        115                 120                 125

Tyr Phe Asp Tyr Trp Gly Gln Gly Val Met Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Ala Ser Leu Ser Thr Ser Leu Gly Glu Thr
                165                 170                 175

Val Thr Ile Gln Cys Gln Ala Ser Glu Asp Ile Tyr Ser Gly Leu Ala
            180                 185                 190

Trp Tyr Gln Gln Lys Pro Gly Lys Ser Pro Gln Leu Leu Ile Tyr Gly
        195                 200                 205

Ala Ser Asp Leu Gln Asp Gly Val Pro Ser Arg Phe Ser Gly Ser Gly
    210                 215                 220

Ser Gly Thr Gln Tyr Ser Leu Lys Ile Thr Ser Met Gln Thr Glu Asp
225                 230                 235                 240

Glu Gly Val Tyr Phe Cys Gln Gln Gly Leu Thr Tyr Pro Arg Thr Phe
                245                 250                 255

Gly Gly Gly Thr Lys Leu Glu Leu Lys Arg Ala Ala Ala Glu Gln Lys
            260                 265                 270

Leu Ile Ser Glu Glu Asp Leu Ile Glu Phe Met Tyr Pro Pro Pro Tyr
        275                 280                 285
```

```
Leu Asp Asn Glu Arg Ser Asn Gly Thr Ile Ile His Ile Lys Glu Lys
    290                 295                 300

His Leu Cys His Thr Gln Ser Ser Pro Lys Leu Phe Trp Ala Leu Val
305                 310                 315                 320

Val Val Ala Gly Val Leu Phe Cys Tyr Gly Leu Leu Val Thr Val Ala
                325                 330                 335

Leu Cys Val Ile Trp Thr Asn Ser Arg Arg Asn Arg Leu Leu Gln Ser
                340                 345                 350

Asp Tyr Met Asn Met Thr Pro Arg Arg Pro Gly Leu Thr Arg Lys Pro
            355                 360                 365

Tyr Gln Pro Tyr Ala Pro Ala Arg Asp Phe Ala Ala Tyr Arg Pro Arg
    370                 375                 380

Ala Lys Phe Ser Arg Ser Ala Glu Thr Ala Ala Asn Leu Gln Asp Pro
385                 390                 395                 400

Asn Gln Leu Tyr Asn Glu Leu Asn Leu Gly Arg Arg Glu Glu Tyr Asp
                405                 410                 415

Val Leu Glu Lys Lys Arg Ala Arg Asp Pro Glu Met Gly Gly Lys Gln
                420                 425                 430

Gln Arg Arg Arg Asn Pro Gln Glu Gly Val Tyr Asn Ala Leu Gln Lys
            435                 440                 445

Asp Lys Met Ala Glu Ala Tyr Ser Glu Ile Gly Thr Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Thr Leu Ala Pro Arg
                485                 490                 495

<210> SEQ ID NO 7
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggcctcac cgttgacccg ctttctgtcg ctgaacctgc tgctgctggg tgagtcgatt        60
atcctgggga gtggagaagc tgaagtccag ctgcagcagt ctggggctga gcttgtgaga       120
cctgggacct ctgtgaagtt atcttgcaaa gtttctggcg ataccattac attttactac       180
atgcactttg tgaagcaaag gcctggacag ggtctggaat ggataggaag gattgatcct       240
gaggatgaaa gtactaaata ttctgagaag ttcaaaaaca aggcgacact cactgcagat       300
acatcttcca acacagccta cctgaagctc agcagcctga cctctgagga cactgcaacc       360 tattttgta tctacggagg atactacttt gattactggg gccaaggggt catggtcaca       420
gtctcctcag gtgaggtgg atcaggtgga ggtggatctg gtgaggtgg atctgacatc       480 cagatgacac agtctccagc ttccctgtct acatctctgg agaaactgt caccatccaa       540 tgtcaagcaa gtgaggacat ttacagtggt ttagcgtggt atcagcagaa gccagggaaa       600
tctcctcagc tcctgatcta tggtgcaagt gacttacaag acggcgtccc atcacgattc       660
agtggcagtg gatctggcac acagtattct ctcaagatca ccagcatgca aactgaagat       720
gaagggtttt atttctgtca acagggttta acgtatcctc ggacgttcgg tggcggcacc       780
aagctggaat tgaaacgggc ggccgcagaa cagaaactga tctctgaaga agaccctgatt       840
```

```
gagttcatgt acccctccgcc ttacctagac aacgagagga gcaatggaac tattattcac    900
ataaaagaga acatctttg tcatactcag tcatctccta agctgttttg ggcactggtc     960
gtggttgctg gagtcctgtt ttgttatggc ttgctagtga cagtggctct ttgtgttatc   1020
tggacaaata gtagaaggaa cagactcctt caaagtgact acatgaacat gactccccgg   1080
aggcctgggc tcactcgaaa gccttaccag ccctacgccc tgccagaga ctttgcagcg    1140 taccgcccca gagcaaaatt cagcaggagt gcagagactg ctgccaacct gcaggacccc   1200
aaccagctct acaatgagct caatctaggg cgaagagagg aatatgacgt cttggagaag   1260
aagcgggctc gggatccaga gatgggaggc aaacagcaga ggaggaggaa ccccaggaa    1320 ggcgtataca atgcactgca gaaagacaag atggcagaag cctacagtga gatcggcaca   1380
aaaggcgaga ggcggagagg caaggggcac gatggccttt accagggtct cagcactgcc   1440
accaaggaca cctatgatgc cctgcatatg cagaccctgg cccctcgcta a            1491
```

<210> SEQ ID NO 8
<211> LENGTH: 20
<212> TYPE: PRT
<213> ORGANISM: Homo sapiens

<400> SEQUENCE: 8

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 9
<211> LENGTH: 235
<212> TYPE: PRT
<213> ORGANISM: Homo sapiens

<400> SEQUENCE: 9

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190
```

```
Cys Gly Val Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235
```

<210> SEQ ID NO 10
<211> LENGTH: 247
<212> TYPE: PRT
<213> ORGANISM: Mus musculus

<400> SEQUENCE: 10

```
Met Ala Ser Pro Leu Thr Arg Phe Leu Ser Leu Asn Leu Leu Leu Met
1               5                   10                  15

Gly Glu Ser Ile Ile Leu Gly Ser Gly Glu Ala Lys Pro Gln Ala Pro
                20                  25                  30

Glu Leu Arg Ile Phe Pro Lys Lys Met Asp Ala Glu Leu Gly Gln Lys
            35                  40                  45

Val Asp Leu Val Cys Glu Val Leu Gly Ser Val Ser Gln Gly Cys Ser
        50                  55                  60

Trp Leu Phe Gln Asn Ser Ser Ser Lys Leu Pro Gln Pro Thr Phe Val
65                  70                  75                  80

Val Tyr Met Ala Ser Ser His Asn Lys Ile Thr Trp Asp Glu Lys Leu
                85                  90                  95

Asn Ser Ser Lys Leu Phe Ser Ala Val Arg Asp Thr Asn Asn Lys Tyr
            100                 105                 110

Val Leu Thr Leu Asn Lys Phe Ser Lys Glu Asn Glu Gly Tyr Tyr Phe
        115                 120                 125

Cys Ser Val Ile Ser Asn Ser Val Met Tyr Phe Ser Ser Val Val Pro
130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175

Asp Cys Arg Pro Arg Gly Ser Val Lys Gly Thr Gly Leu Asp Phe Ala
            180                 185                 190

Cys Asp Ile Tyr Ile Trp Ala Pro Leu Ala Gly Ile Cys Val Ala Pro
        195                 200                 205

Leu Leu Ser Leu Ile Ile Thr Leu Ile Cys Tyr His Arg Ser Arg Lys
210                 215                 220

Arg Val Cys Lys Cys Pro Arg Pro Leu Val Arg Gln Glu Gly Lys Pro
225                 230                 235                 240

Arg Pro Ser Glu Lys Ile Val
                245
```

<210> SEQ ID NO 11
<211> LENGTH: 69
<212> TYPE: PRT
<213> ORGANISM: Mus musculus

<400> SEQUENCE: 11

```
Ser Thr Thr Thr Lys Pro Val Leu Arg Thr Pro Ser Pro Val His Pro
1               5                   10                  15

Thr Gly Thr Ser Gln Pro Gln Arg Pro Glu Asp Cys Arg Pro Arg Gly
                20                  25                  30
```

Ser Val Lys Gly Thr Gly Leu Asp Phe Ala Cys Asp Ile Tyr Ile Trp
            35                  40                  45

Ala Pro Leu Ala Gly Ile Cys Val Ala Leu Leu Ser Leu Ile Ile
    50                  55                  60

Thr Leu Ile Cys Tyr
65

<210> SEQ ID NO 12
<211> LENGTH: 207
<212> TYPE: DNA
<213> ORGANISM: Mus musculus

<400> SEQUENCE: 12
tctactacta ccaagccagt gctgcgaact ccctcacctg tgcaccctac cgggacatct     60
cagccccaga gaccagaaga ttgtcggccc cgtggctcag tgaagggac cggattggac    120 ttcgcctgtg atatttacat ctgggcaccc ttggccggaa tctgcgtggc ccttctgctg    180
tccttgatca tcactctcat ctgctac                                        207

<210> SEQ ID NO 13
<211> LENGTH: 188
<212> TYPE: PRT
<213> ORGANISM: Mus musculus

<400> SEQUENCE: 13

Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Ile Thr Ala
        35                  40                  45

Leu Tyr Leu Arg Ala Lys Phe Ser Arg Ser Ala Glu Thr Ala Ala Asn
    50                  55                  60

Leu Gln Asp Pro Asn Gln Leu Tyr Asn Glu Leu Asn Leu Gly Arg Arg
65                  70                  75                  80

Glu Glu Tyr Asp Val Leu Glu Lys Lys Arg Ala Arg Asp Pro Glu Met
                85                  90                  95

Gly Gly Lys Gln Arg Arg Arg Asn Pro Gln Glu Gly Val Tyr Asn Ala
            100                 105                 110

Leu Gln Lys Asp Lys Met Ala Glu Ala Tyr Ser Glu Ile Gly Thr Lys
        115                 120                 125

Gly Glu Arg Arg Arg Gly Lys Gly His Asp Gly Leu Tyr Gln Asp Ser
    130                 135                 140

His Phe Gln Ala Val Gln Phe Gly Asn Arg Arg Glu Arg Glu Gly Ser
145                 150                 155                 160

Glu Leu Thr Arg Thr Leu Gly Leu Arg Ala Arg Pro Lys Ala Cys Arg
                165                 170                 175

His Lys Lys Pro Leu Ser Leu Pro Ala Ala Val Ser
            180                 185

<210> SEQ ID NO 14
<211> LENGTH: 113
<212> TYPE: PRT
<213> ORGANISM: Mus musculus

<400> SEQUENCE: 14

Arg Ala Lys Phe Ser Arg Ser Ala Glu Thr Ala Ala Asn Leu Gln Asp

```
1               5                   10                  15
Pro Asn Gln Leu Tyr Asn Glu Leu Asn Leu Gly Arg Arg Glu Glu Tyr
                20                  25                  30

Asp Val Leu Glu Lys Lys Arg Ala Arg Asp Pro Glu Met Gly Gly Lys
                35                  40                  45

Gln Gln Arg Arg Arg Asn Pro Gln Glu Gly Val Tyr Asn Ala Leu Gln
        50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Thr Leu Ala Pro
                100                 105                 110

Arg
```

<210> SEQ ID NO 15
<211> LENGTH: 342
<212> TYPE: DNA
<213> ORGANISM: Mus musculus

<400> SEQUENCE: 15

```
agagcaaaat tcagcaggag tgcagagact gctgccaacc tgcaggaccc caaccagctc    60
tacaatgagc tcaatctagg gcgaagagag gaatatgacg tcttggagaa gaagcgggct   120
cgggatccag agatgggagg caaacagcag aggaggagga accccaggaa aggcgtatac   180
aatgcactgc agaaagacaa gatggcagaa gcctacagtg agatcggcac aaaaggcgag   240
aggcggagag gcaaggggca cgatggcctt taccagggtc tcagcactgc caccaaggac   300
acctatgatg ccctgcatat gcagaccctg gcccctcgct aa                     342
```

<210> SEQ ID NO 16
<211> LENGTH: 218
<212> TYPE: PRT
<213> ORGANISM: Mus musculus

<400> SEQUENCE: 16

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
                20                  25                  30

Asp Ser Asn Glu Val Ser Leu Ser Cys Arg Tyr Ser Tyr Asn Leu Leu
                35                  40                  45

Ala Lys Glu Phe Arg Ala Ser Leu Tyr Lys Gly Val Asn Ser Asp Val
        50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
                100                 105                 110

Cys Lys Ile Glu Phe Met Tyr Pro Pro Pro Tyr Leu Asp Asn Glu Arg
                115                 120                 125

Ser Asn Gly Thr Ile Ile His Ile Lys Glu Lys His Leu Cys His Thr
        130                 135                 140

Gln Ser Ser Pro Lys Leu Phe Trp Ala Leu Val Val Val Ala Gly Val
145                 150                 155                 160
```

```
Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
        195                 200                 205

Pro Ala Arg Asp Phe Ala Ala Tyr Arg Pro
    210                 215

<210> SEQ ID NO 17
<211> LENGTH: 123
<212> TYPE: DNA
<213> ORGANISM: Mus musculus

<400> SEQUENCE: 17
aatagtagaa ggaacagact ccttcaaagt gactacatga acatgactcc ccggaggcct      60
gggctcactc gaaagcctta ccagccctac gcccctgcca gagactttgc agcgtaccgc     120
ccc                                                                   123

<210> SEQ ID NO 18
<211> LENGTH: 277
<212> TYPE: PRT
<213> ORGANISM: Homo sapiens

<400> SEQUENCE: 18

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240
```

Arg Arg Asp Gln Arg Leu Pro Pro Asp Ala His Lys Pro Pro Gly Gly
            245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 19
<211> LENGTH: 199
<212> TYPE: PRT
<213> ORGANISM: Homo sapiens

<400> SEQUENCE: 19

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 20
<211> LENGTH: 160
<212> TYPE: PRT
<213> ORGANISM: Homo sapiens

<400> SEQUENCE: 20

Arg Glu Ala Ala Pro Lys Ser Tyr Ala Ile Arg Asp Ser Arg Gln Met
1               5                   10                  15

Val Trp Val Leu Ser Gly Asn Ser Leu Ile Ala Ala Pro Leu Ser Arg
            20                  25                  30

Ser Ile Lys Pro Val Thr Leu His Leu Ile Ala Cys Arg Asp Thr Glu
        35                  40                  45

Phe Ser Asp Lys Glu Lys Gly Asn Met Val Tyr Leu Gly Ile Lys Gly
    50                  55                  60

Lys Asp Leu Cys Leu Phe Cys Ala Glu Ile Gln Gly Lys Pro Thr Leu
65                  70                  75                  80

Gln Leu Lys Leu Gln Gly Ser Gln Asp Asn Ile Gly Lys Asp Thr Cys
            85                  90                  95

Trp Lys Leu Val Gly Ile His Thr Cys Ile Asn Leu Asp Val Arg Glu
        100                 105                 110

Ser Cys Phe Met Gly Thr Leu Asp Gln Trp Gly Ile Gly Val Gly Arg
        115                 120                 125

Lys Lys Trp Lys Ser Ser Phe Gln His His Leu Arg Lys Lys Asp
    130                 135                 140

Lys Asp Phe Ser Ser Met Arg Thr Asn Ile Gly Met Pro Gly Arg Met
145                 150                 155                 160

<210> SEQ ID NO 21
<211> LENGTH: 152
<212> TYPE: PRT
<213> ORGANISM: Homo sapiens

<400> SEQUENCE: 21

Ser Met Cys Lys Pro Ile Thr Gly Thr Ile Asn Asp Leu Asn Gln Gln
1               5                   10                  15

Val Trp Thr Leu Gln Gly Gln Asn Leu Val Ala Val Pro Arg Ser Asp
            20                  25                  30

Ser Val Thr Pro Val Thr Val Ala Val Ile Thr Cys Lys Tyr Pro Glu
        35                  40                  45

Ala Leu Glu Gln Gly Arg Gly Asp Pro Ile Tyr Leu Gly Ile Gln Asn
    50                  55                  60

Pro Glu Met Cys Leu Tyr Cys Glu Lys Val Gly Glu Gln Pro Thr Leu
65                  70                  75                  80

Gln Leu Lys Glu Gln Lys Ile Met Asp Leu Tyr Gly Gln Pro Glu Pro
            85                  90                  95

Val Lys Pro Phe Leu Phe Tyr Arg Ala Lys Thr Gly Arg Thr Ser Thr
        100                 105                 110

Leu Glu Ser Val Ala Phe Pro Asp Trp Phe Ile Ala Ser Ser Lys Arg
        115                 120                 125

Asp Gln Pro Ile Ile Leu Thr Ser Glu Leu Gly Lys Ser Tyr Asn Thr
    130                 135                 140

Ala Phe Glu Leu Asn Ile Asn Asp
145                 150

<210> SEQ ID NO 22
<211> LENGTH: 81
<212> TYPE: DNA
<213> ORGANISM: Homo sapiens

<400> SEQUENCE: 22
ttttgggtgc tggtggtggt tggtggagtc ctggcttgct atagcttgct agtaacagtg    60
gcctttatta ttttctgggt g                                              81

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Ser Gly Gly Gly Ser Gly Gly Gly Gly Ser
1               5                   10                  15

```
<210> SEQ ID NO 24
<211> LENGTH: 20
<212> TYPE: PRT
<213> ORGANISM: Mus musculus

<400> SEQUENCE: 24

Met Tyr Ser Met Gln Leu Ala Ser Cys Val Thr Leu Thr Leu Val Leu
1               5                   10                  15

Leu Val Asn Ser
            20

<210> SEQ ID NO 25
<211> LENGTH: 20
<212> TYPE: PRT
<213> ORGANISM: Homo sapiens

<400> SEQUENCE: 25

Met Glu Thr Pro Ala Gln Leu Leu Phe Leu Leu Leu Leu Trp Leu Pro
1               5                   10                  15

Asp Thr Thr Gly
            20

<210> SEQ ID NO 26
<211> LENGTH: 20
<212> TYPE: PRT
<213> ORGANISM: Mus musculus

<400> SEQUENCE: 26

Met Glu Thr Asp Thr Leu Leu Leu Trp Val Leu Leu Leu Trp Val Pro
1               5                   10                  15

Gly Ser Thr Gly
            20

<210> SEQ ID NO 27
<211> LENGTH: 21
<212> TYPE: PRT
<213> ORGANISM: Homo sapiens

<400> SEQUENCE: 27

Met Ala Leu Pro Val Thr Ala Leu Leu Leu Pro Leu Ala Leu Leu Leu
1               5                   10                  15

His Ala Ala Arg Pro
            20

<210> SEQ ID NO 28
<211> LENGTH: 16
<212> TYPE: PRT
<213> ORGANISM: Homo sapiens

<400> SEQUENCE: 28

Met Lys Trp Val Thr Phe Ile Ser Leu Leu Phe Ser Ser Ala Tyr Ser
1               5                   10                  15

<210> SEQ ID NO 29
<211> LENGTH: 30
<212> TYPE: PRT
<213> ORGANISM: Homo sapiens

<400> SEQUENCE: 29

Met Asp Ser Lys Gly Ser Ser Gln Lys Gly Ser Arg Leu Leu Leu Leu
1               5                   10                  15
```

```
Leu Val Val Ser Asn Leu Leu Leu Cys Gln Gly Val Val Ser
            20                  25                  30
```

<210> SEQ ID NO 30
<211> LENGTH: 152
<212> TYPE: PRT
<213> ORGANISM: Mus musculus

<400> SEQUENCE: 30

```
Gly Arg Glu Thr Pro Asp Phe Gly Val Phe Asp Leu Asp Gln Gln
1               5                   10                  15

Val Trp Ile Phe Arg Asn Gln Ala Leu Val Thr Val Pro Arg Ser His
            20                  25                  30

Arg Val Thr Pro Val Ser Val Thr Ile Leu Pro Cys Lys Tyr Pro Glu
            35                  40                  45

Ser Leu Glu Gln Asp Lys Gly Ile Ala Ile Tyr Leu Gly Ile Gln Asn
50                  55                  60

Pro Asp Lys Cys Leu Phe Cys Lys Glu Val Asn Gly His Pro Thr Leu
65                  70                  75                  80

Leu Leu Lys Glu Glu Lys Ile Leu Asp Leu Tyr His His Pro Glu Pro
                85                  90                  95

Met Lys Pro Phe Leu Phe Tyr His Thr Arg Thr Gly Thr Ser Thr
            100                 105                 110

Phe Glu Ser Val Ala Phe Pro Gly His Tyr Ile Ala Ser Ser Lys Thr
            115                 120                 125

Gly Asn Pro Ile Phe Leu Thr Ser Lys Lys Gly Glu Tyr Tyr Asn Ile
            130                 135                 140

Asn Phe Asn Leu Asp Ile Lys Ser
145                 150
```

<210> SEQ ID NO 31
<211> LENGTH: 153
<212> TYPE: PRT
<213> ORGANISM: Mus musculus

<400> SEQUENCE: 31

```
Ser Ser Gln Ser Pro Arg Asn Tyr Arg Val His Asp Ser Gln Gln Met
1               5                   10                  15

Val Trp Val Leu Thr Gly Asn Thr Leu Thr Ala Val Pro Ala Ser Asn
            20                  25                  30

Asn Val Lys Pro Val Ile Leu Ser Leu Ile Ala Cys Arg Asp Thr Glu
            35                  40                  45

Phe Gln Asp Val Lys Lys Gly Asn Leu Val Phe Leu Gly Ile Lys Asn
50                  55                  60

Arg Asn Leu Cys Phe Cys Cys Val Glu Met Glu Gly Lys Pro Thr Leu
65                  70                  75                  80

Gln Leu Lys Glu Val Asp Ile Met Asn Leu Tyr Lys Glu Arg Lys Ala
                85                  90                  95

Gln Lys Ala Phe Leu Phe Tyr His Gly Ile Glu Gly Ser Thr Ser Val
            100                 105                 110

Phe Gln Ser Val Leu Tyr Pro Gly Trp Phe Ile Ala Thr Ser Ser Ile
            115                 120                 125

Glu Arg Gln Thr Ile Ile Leu Thr His Gln Arg Gly Lys Leu Val Asn
            130                 135                 140

Thr Asn Phe Tyr Ile Glu Ser Glu Lys
145                 150
```

```
<210> SEQ ID NO 32
<211> LENGTH: 152
<212> TYPE: PRT
<213> ORGANISM: Mus musculus

<400> SEQUENCE: 32

Gly Arg Glu Thr Pro Asp Phe Gly Glu Val Phe Asp Leu Asp Gln Gln
1               5                   10                  15

Val Trp Ile Phe Arg Asn Gln Ala Leu Val Thr Val Pro Arg Ser His
            20                  25                  30

Arg Val Thr Pro Val Ser Val Thr Ile Leu Pro Cys Lys Tyr Pro Glu
        35                  40                  45

Ser Leu Glu Gln Asp Lys Gly Ile Ala Ile Tyr Leu Gly Ile Gln Asn
50                  55                  60

Pro Asp Lys Cys Leu Phe Cys Lys Glu Val Asn Gly His Pro Thr Leu
65                  70                  75                  80

Leu Leu Lys Glu Glu Lys Ile Leu Asp Leu Tyr His His Pro Glu Pro
                85                  90                  95

Met Lys Pro Phe Leu Phe Tyr His Thr Arg Thr Gly Gly Thr Ser Thr
            100                 105                 110

Phe Glu Ser Val Ala Phe Pro Gly His Tyr Ile Ala Ser Ser Lys Thr
        115                 120                 125

Gly Asn Pro Ile Phe Leu Thr Ser Lys Lys Gly Glu Tyr Tyr Asn Ile
130                 135                 140

Asn Phe Asn Leu Asp Ile Lys Ser
145                 150

<210> SEQ ID NO 33
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
130                 135                 140

Ser Gly Gly Gly Gly Ser Gly Gly Gly Gly Ser Asp Ile Glu Leu Thr
145                 150                 155                 160
```

Gln Ser Pro Lys Phe Met Ser Thr Ser Val Gly Asp Arg Val Ser Val
            165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
            195                 200                 205

Arg Asn Ser Gly Val Pro Asp Arg Phe Thr Gly Ser Gly Ser Gly Thr
            210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
            245                 250                 255

Thr Lys Leu Glu Ile Lys Arg Ala Ala Ala Ile Glu Phe Met Tyr Pro
            260                 265                 270

Pro Pro Tyr Leu Asp Asn Glu Arg Ser Asn Gly Thr Ile Ile His Ile
            275                 280                 285

Lys Glu Lys His Leu Cys His Thr Gln Ser Ser Pro Lys Leu Phe Trp
            290                 295                 300

Ala Leu Val Val Val Ala Gly Val Leu Phe Cys Tyr Gly Leu Leu Val
305                 310                 315                 320

Thr Val Ala Leu Cys Val Ile Trp Thr Arg Ala Lys Phe Ser Arg Ser
            325                 330                 335

Ala Glu Thr Ala Ala Asn Leu Gln Asp Pro Asn Gln Leu Tyr Asn Glu
            340                 345                 350

Leu Asn Leu Gly Arg Arg Glu Glu Tyr Asp Val Leu Glu Lys Lys Arg
            355                 360                 365

Ala Arg Asp Pro Glu Met Gly Gly Lys Gln Gln Arg Arg Arg Asn Pro
            370                 375                 380

Gln Glu Gly Val Tyr Asn Ala Leu Gln Lys Asp Lys Met Ala Glu Ala
385                 390                 395                 400

Tyr Ser Glu Ile Gly Thr Lys Gly Glu Arg Arg Arg Gly Lys Gly His
            405                 410                 415

Asp Gly Leu Tyr Gln Gly Leu Ser Thr Ala Thr Lys Asp Thr Tyr Asp
            420                 425                 430

Ala Leu His Met Gln Thr Leu Ala Pro Arg
            435                 440

<210> SEQ ID NO 34
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggctctcc cagtgactgc cctactgctt cccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
tcggtagtag atttctactt tgactactgg ggccaaggga ccacggtcac cgtctcctca     420

```
ggtggaggtg gatcaggtgg aggtggatct ggtggaggtg gatctgacat tgagctcacc      480
cagtctccaa aattcatgtc cacatcagta ggagacaggg tcagcgtcac ctgcaaggcc      540
agtcagaatg tgggtactaa tgtagcctgg tatcaacaga accaggaca atctcctaaa       600
ccactgattt actcggcaac ctaccggaac agtggagtcc ctgatcgctt cacaggcagt      660
ggatctggga cagatttcac tctcaccatc actaacgtgc agtctaaaga cttggcagac      720
tatttctgtc aacaatataa caggtatccg tacacgtccg gagggggggac caagctggag     780
atcaaacggg cggccgcaat tgagttcatg taccctccgc cttacctaga caacgagagg      840
agcaatggaa ctattattca cataaaagag aaacatcttt gtcatactca gtcatctcct      900
aagctgtttt gggcactggt cgtggttgct ggagtcctgt tttgttatgg cttgctagtg      960
acagtggctc tttgtgttat ctggacaaga gcaaaattca gcaggagtgc agagactgct     1020
gccaacctgc aggaccccaa ccagctctac aatgagctca atctagggcg aagagaggaa     1080
tatgacgtct tggagaagaa gcgggctcgg gatccagaga tgggaggcaa acagcagagg     1140
aggaggaacc cccaggaagg cgtatacaat gcactgcaga aagacaagat ggcagaagcc     1200
tacagtgaga tcggcacaaa aggcgagagg cggagaggca aggggcacga tggcctttac     1260
cagggtctca gcactgccac caaggacacc tatgatgccc tgcatatgca gaccctggcc     1320
cctcgctaa                                                             1329
```

<210> SEQ ID NO 35
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190
```

Gln Lys Pro Gly Gln Ser Pro Lys Pro Leu Ile Tyr Ser Ala Thr Tyr
            195                 200                 205

Arg Asn Ser Gly Val Pro Asp Arg Phe Thr Gly Ser Gly Ser Gly Thr
        210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Val Lys Phe
                325                 330                 335

Ser Arg Ser Ala Asp Ala Pro Ala Tyr Gln Gln Gly Gln Asn Gln Leu
            340                 345                 350

Tyr Asn Glu Leu Asn Leu Gly Arg Arg Glu Glu Tyr Asp Val Leu Asp
        355                 360                 365

Lys Arg Arg Gly Arg Asp Pro Glu Met Gly Gly Lys Pro Arg Arg Lys
370                 375                 380

Asn Pro Gln Glu Gly Leu Tyr Asn Glu Leu Gln Lys Asp Lys Met Ala
385                 390                 395                 400

Glu Ala Tyr Ser Glu Ile Gly Met Lys Gly Glu Arg Arg Arg Gly Lys
                405                 410                 415

Gly His Asp Gly Leu Tyr Gln Gly Leu Ser Thr Ala Thr Lys Asp Thr
            420                 425                 430

Tyr Asp Ala Leu His Met Gln Ala Leu Pro Pro Arg
        435                 440

<210> SEQ ID NO 36
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atggctctcc cagtgactgc cctactgctt cccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
tcggtagtag atttctactt tgactactgg ggccaaggga ccacggtcac cgtctcctca     420
ggtggaggtg gatcaggtgg aggtggatct ggtggaggtg gatctgacat tgagctcacc     480
cagtctccaa aattcatgtc cacatcagta ggagacaggg tcagcgtcac ctgcaaggcc     540
agtcagaatg tgggtactaa tgtagcctgg tatcaacaga accaggaca atctcctaaa     600

```
ccactgattt actcggcaac ctaccggaac agtggagtcc ctgatcgctt cacaggcagt    660
ggatctggga cagatttcac tctccaccatc actaacgtgc agtctaaaga cttggcagac   720
tatttctgtc aacaatataa caggtatccg tacacgtccg gagggggac caagctggag    780 atcaaacggg cggccgcaat tgaagttatg tatcctcctc cttacctaga caatgagaag    840
agcaatggaa ccattatcca tgtgaaaggg aaacaccttt gtccaagtcc cctatttccc    900
ggaccttcta agccctttg gtgctggtg gtggttggtg gagtcctggc ttgctatagc      960
ttgctagtaa cagtggcctt tattattttc tgggtgagag tgaagttcag caggagcgca   1020 gacgccccg cgtaccagca gggccagaac cagctctata cgagctcaa tctaggacga   1080 agagaggagt acgatgtttt ggacaagaga cgtggccggg accctgagat ggggggaaag   1140
ccgagaagga agaaccctca ggaaggcctg tacaatgaac tgcagaaaga taagatggcg   1200
gaggcctaca gtgagattgg gatgaaaggc gagcgccgga ggggcaaggg gcacgatggc   1260
ctttaccagg gtctcagtac agccaccaag gacacctacg acgcccttca catgcaggcc   1320
ctgccccctc gctag                                                    1335
```

<210> SEQ ID NO 37
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220
```

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
            245                 250                 255

Thr Lys Leu Glu Ile Lys Arg Ala Ala Ala Ile Glu Phe Met Tyr Pro
        260                 265                 270

Pro Tyr Leu Asp Asn Glu Arg Ser Asn Gly Thr Ile Ile His Ile
    275                 280                 285

Lys Glu Lys His Leu Cys His Thr Gln Ser Ser Pro Lys Leu Phe Trp
    290                 295                 300

Ala Leu Val Val Ala Gly Val Leu Phe Cys Tyr Gly Leu Leu Val
305                 310                 315                 320

Thr Val Ala Leu Cys Val Ile Trp Thr Asn Ser Arg Arg Asn Arg Leu
            325                 330                 335

Leu Gln Ser Asp Tyr Met Asn Met Thr Pro Arg Arg Pro Gly Leu Thr
            340                 345                 350

Arg Lys Pro Tyr Gln Pro Tyr Ala Pro Ala Arg Asp Phe Ala Ala Tyr
        355                 360                 365

Arg Pro Arg Ala Lys Phe Ser Arg Ser Ala Glu Thr Ala Ala Asn Leu
370                 375                 380

Gln Asp Pro Asn Gln Leu Tyr Asn Glu Leu Asn Leu Gly Arg Arg Glu
385                 390                 395                 400

Glu Tyr Asp Val Leu Glu Lys Lys Arg Ala Arg Asp Pro Glu Met Gly
            405                 410                 415

Gly Lys Gln Gln Arg Arg Arg Asn Pro Gln Glu Gly Val Tyr Asn Ala
        420                 425                 430

Leu Gln Lys Asp Lys Met Ala Glu Ala Tyr Ser Glu Ile Gly Thr Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Thr Leu
465                 470                 475                 480

Ala Pro Arg

<210> SEQ ID NO 38
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atggctctcc cagtgactgc cctactgctt cccctagcgc ttctcctgca tgcagaggtg      60
aagctgcagc agtctggggc tgagctggtg aggcctgggt cctcagtgaa gatttcctgc    120
aaggcttctg ctatgcatt cagtagctac tggatgaact gggtgaagca gaggcctgga    180
cagggtcttg agtggattgg acagatttat cctggagatg gtgatactaa ctacaatgga    240
aagttcaagg gtcaagccac actgactgca gacaaatcct ccagcacagc ctacatgcag    300
ctcagcggcc taacatctga ggactctgcg gtctatttct gtgcaagaaa gaccattagt    360
tcggtagtag atttctactt tgactactgg ggccaaggga ccacggtcac cgtctcctca    420
ggtggaggtg gatcaggtgg aggtggatct ggtggaggtg gatctgacat tgagctcacc    480
cagtctccaa aattcatgtc cacatcagta ggagacaggg tcagcgtcac ctgcaaggcc    540

```
agtcagaatg tgggtactaa tgtagcctgg tatcaacaga aaccaggaca atctcctaaa    600
ccactgattt actcggcaac ctaccggaac agtggagtcc ctgatcgctt cacaggcagt    660
ggatctggga cagatttcac tctcaccatc actaacgtgc agtctaaaga cttggcagac    720
tatttctgtc aacaatataa caggtatccg tacacgtccg gagggggac  caagctggag    780 atcaaacggg cggccgcaat tgagttcatg taccctccgc cttacctaga caacgagagg    840
agcaatggaa ctattattca cataaaagag aaacatcttt gtcatactca gtcatctcct    900
aagctgtttt gggcactggt cgtggttgct ggagtcctgt tttgttatgg cttgctagtg    960
acagtggctc tttgtgttat ctggacaaat agtagaagga acagactcct tcaaagtgac   1020
tacatgaaca tgactccccg gaggcctggg ctcactcgaa agccttacca gccctacgcc   1080
cctgccagag actttgcagc gtaccgcccc agagcaaaat tcagcaggag tgcagagact   1140
gctgccaacc tgcaggaccc caaccagctc tacaatgagc tcaatctagg gcgaagagag   1200
gaatatgacg tcttggagaa gaagcgggct cgggatccag agatgggagg caaacagcag   1260
aggaggagga accccagga  aggcgtatac aatgcactgc agaaagacaa gatggcagaa   1320
gcctacagtg agatcggcac aaaaggcgag aggcggagag caaggggca  cgatggcctt   1380 taccagggtc tcagcactgc caccaaggac acctatgatg ccctgcatat gcagaccctg   1440 gccccctcgct ga                                                      1452
```

<210> SEQ ID NO 39
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
                20                  25                  30

Gly Ser Ser Val Lys Ile Ser Cys Lys Ala Ser Gly Tyr Ala Phe Ser
            35                  40                  45

Ser Tyr Trp Met Asn Trp Val Lys Gln Arg Pro Gly Gln Gly Leu Glu
        50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

-continued

```
Gln Lys Pro Gly Gln Ser Pro Lys Pro Leu Ile Tyr Ser Ala Thr Tyr
            195                 200                 205

Arg Asn Ser Gly Val Pro Asp Arg Phe Thr Gly Ser Gly Ser Gly Thr
        210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
    290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
                485
```

<210> SEQ ID NO 40
<211> LENGTH: 1458
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
atggctctcc cagtgactgc cctactgctt ccccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
```

-continued

```
tcggtagtag atttctactt tgactactgg ggccaaggga ccacggtcac cgtctcctca    420
ggtggaggtg gatcaggtgg aggtggatct ggtggaggtg gatctgacat tgagctcacc    480
cagtctccaa aattcatgtc cacatcagta ggagacaggg tcagcgtcac ctgcaaggcc    540
agtcagaatg tgggtactaa tgtagcctgg tatcaacaga aaccaggaca atctcctaaa    600
ccactgattt actcggcaac ctaccggaac agtggagtcc ctgatcgctt cacaggcagt    660
ggatctggga cagatttcac tctcaccatc actaacgtgc agtctaaaga cttggcagac    720
tatttctgtc aacaatataa caggtatccg tacacgtccg agggggggac caagctggag    780
atcaaacggg cggccgcaat tgaagttatg tatcctcctc cttacctaga caatgagaag    840
agcaatggaa ccattatcca tgtgaaaggg aaacaccttt gtccaagtcc cctatttccc    900
ggaccttcta agccctttg ggtgctggtg gtggttggtg gagtcctggc ttgctatagc    960
ttgctagtaa cagtggcctt tattattttc tgggtgagga gtaagaggag caggctcctg   1020
cacagtgact acatgaacat gactccccgc cgcccggg ccacccgcaa gcattaccag   1080
ccctatgccc caccacgcga cttcgcagcc tatcgctcca gagtgaagtt cagcaggagc   1140
gcagacgccc ccgcgtacca gcagggccag aaccagctct ataacgagct caatctagga   1200
cgaagagagg agtacgatgt tttggacaag agacgtggcc gggaccctga tgggggga   1260 aagccgagaa ggaagaaccc tcaggaaggc ctgtacaatg aactcagaa agataagatg   1320 gcggaggcct acagtgagat tgggatgaaa ggcgagcgcc ggaggggcaa ggggcacgat   1380
ggcctttacc agggtctcag tacagccacc aaggacacct acgacgccct tcacatgcag   1440
gccctgcccc ctcgctag                                                 1458
```

<210> SEQ ID NO 41
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160
```

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
            260                 265                 270

Pro Pro Tyr Leu Asp Asn Glu Lys Ser Asn Gly Thr Ile Ile His Val
        275                 280                 285

Lys Gly Lys His Leu Cys Pro Ser Pro Leu Phe Pro Gly Pro Ser Lys
    290                 295                 300

Pro Phe Trp Val Leu Val Val Val Gly Gly Val Leu Ala Cys Tyr Ser
305                 310                 315                 320

Leu Leu Val Thr Val Ala Phe Ile Ile Phe Trp Val Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 42
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atggctctcc cagtgactgc cctactgctt cccctagcgc ttctcctgca tgcagaggtg      60
aagctgcagc agtctggggc tgagctggtg aggcctgggt cctcagtgaa gatttcctgc     120

```
aaggcttctg gctatgcatt cagtagctac tggatgaact gggtgaagca gaggcctgga      180
cagggtcttg agtggattgg acagatttat cctggagatg gtgatactaa ctacaatgga      240
aagttcaagg gtcaagccac actgactgca gacaaatcct ccagcacagc ctacatgcag      300
ctcagcggcc taacatctga ggactctgcg gtctatttct gtgcaagaaa gaccattagt      360
tcggtagtag atttctactt tgactactgg ggccaaggga ccacggtcac cgtctcctca      420
ggtggaggtg gatcaggtgg aggtggatct ggtggaggtg gatctgacat tgagctcacc      480
cagtctccaa aattcatgtc cacatcagta ggagacaggg tcagcgtcac ctgcaaggcc      540
agtcagaatg tgggtactaa tgtagcctgg tatcaacaga aaccaggaca atctcctaaa      600
ccactgattt actcggcaac ctaccggaac agtggagtcc ctgatcgctt cacaggcagt      660
ggatctggga cagatttcac tctcaccatc actaacgtgc agtctaaaga cttggcagac      720
tatttctgtc aacaatataa caggtatccg tacacgtccg gagggggggac caagctggag      780 atcaaacggg cggccgcaat tgaagttatg tatcctcctc cttacctaga caatgagaag      840
agcaatggaa ccattatcca tgtgaaaggg aaacaccttt gtccaagtcc cctatttccc      900
ggaccttcta agccctttg ggtgctggtg gtggttggtg gagtcctggc ttgctatagc      960
ttgctagtaa cagtggcctt tattattttc tgggtgaaac ggggcagaaa gaaactcctg      1020
tatatattca acaaccatt tatgagacca gtacaaacta ctcaagagga agatggctgt      1080
agctgccgat ttccagaaga agaagaagga ggatgtgaac tgagagtgaa gttcagcagg      1140
agcgcagacg cccccgcgta ccagcagggc cagaaccagc tctataacga gctcaatcta      1200
ggacgaagag aggagtacga tgttttggac aagagacgtg gccgggaccc tgagatgggg      1260
ggaaagccga aaggaagaa ccctcaggaa ggcctgtaca atgaactgca gaaagataag      1320
atggcggagg cctacagtga gattgggatg aaaggcgagc gccggagggg caaggggcac      1380
gatggccttt accagggtct cagtacagcc accaaggaca cctacgacgc ccttcacatg      1440 caggcccctgc cccctcgcta g                                              1461
```

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Phe Tyr Tyr Met His
1               5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ile Asp Pro Glu Asp Glu Ser Thr Lys Tyr Ser Glu Lys Phe Lys
1               5                   10                  15

Asn

<210> SEQ ID NO 45
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Tyr Tyr Phe Asp Tyr
1               5

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ala Ser Glu Asp Ile Tyr Ser Gly Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Ala Ser Asp Leu Gln Asp
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Gly Leu Thr Tyr Pro Arg Thr
1               5

<210> SEQ ID NO 49
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Gln Gln Ser Gly Ala Glu Leu Val Arg Pro Gly Thr
1               5                   10                  15

Ser Val Lys Leu Ser Cys Lys Val Ser Gly Asp Thr Ile Thr Phe Tyr
            20                  25                  30

Tyr Met His Phe Val Lys Gln Arg Pro Gly Gln Gly Leu Glu Trp Ile
        35                  40                  45

Gly Arg Ile Asp Pro Glu Asp Glu Ser Thr Lys Tyr Ser Glu Lys Phe
    50                  55                  60

Lys Asn Lys Ala Thr Leu Thr Ala Asp Thr Ser Ser Asn Thr Ala Tyr
65                  70                  75                  80
```

```
Leu Lys Leu Ser Ser Leu Thr Ser Glu Asp Thr Ala Thr Tyr Phe Cys
                85                  90                  95

Ile Tyr Gly Gly Tyr Tyr Phe Asp Tyr Trp Gly Gln Gly Val Met Val
            100                 105                 110

Thr Val Ser Ser
        115

<210> SEQ ID NO 50
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ala Ser Leu Ser Thr Ser Leu Gly
1               5                   10                  15

Glu Thr Val Thr Ile Gln Cys Gln Ala Ser Glu Asp Ile Tyr Ser Gly
            20                  25                  30

Leu Ala Trp Tyr Gln Gln Lys Pro Gly Lys Ser Pro Gln Leu Leu Ile
        35                  40                  45

Tyr Gly Ala Ser Asp Leu Gln Asp Gly Val Pro Ser Arg Phe Ser Gly
    50                  55                  60

Ser Gly Ser Gly Thr Gln Tyr Ser Leu Lys Ile Thr Ser Met Gln Thr
65                  70                  75                  80

Glu Asp Glu Gly Val Tyr Phe Cys Gln Gln Gly Leu Thr Tyr Pro Arg
                85                  90                  95

Thr Phe Gly Gly Gly Thr Lys Leu Glu Leu Lys Arg
            100                 105

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Tyr Ala Phe Ser Ser
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Tyr Pro Gly Asp Gly Asp
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53
```

```
Lys Thr Ile Ser Ser Val Val Asp Phe
1               5
```

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Asn Val Gly Thr Asn Val Ala
1               5
```

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Ser Ala Thr Tyr Arg Asn
1               5
```

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Phe Cys Gln Gln Tyr Asn Arg Tyr
1               5
```

<210> SEQ ID NO 57
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
```

```
                115                 120

<210> SEQ ID NO 58
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105

<210> SEQ ID NO 59
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Glu Val Gln Leu Gln
            20                  25                  30

Gln Ser Gly Ala Glu Leu Val Arg Pro Gly Thr Ser Val Lys Leu Ser
        35                  40                  45

Cys Lys Val Ser Gly Asp Thr Ile Thr Phe Tyr Tyr Met His Phe Val
    50                  55                  60

Lys Gln Arg Pro Gly Gln Gly Leu Glu Trp Ile Gly Arg Ile Asp Pro
65                  70                  75                  80

Glu Asp Glu Ser Thr Lys Tyr Ser Glu Lys Phe Lys Asn Lys Ala Thr
                85                  90                  95

Leu Thr Ala Asp Thr Ser Ser Asn Thr Ala Tyr Leu Lys Leu Ser Ser
            100                 105                 110

Leu Thr Ser Glu Asp Thr Ala Thr Tyr Phe Cys Ile Tyr Gly Gly Tyr
        115                 120                 125

Tyr Phe Asp Tyr Trp Gly Gln Gly Val Met Thr Val Ser Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Ala Ser Leu Ser Thr Ser Leu Gly Glu Thr
                165                 170                 175

Val Thr Ile Gln Cys Gln Ala Ser Glu Asp Ile Tyr Ser Gly Leu Ala
```

```
            180             185             190
Trp Tyr Gln Gln Lys Pro Gly Lys Ser Pro Gln Leu Leu Ile Tyr Gly
        195                 200                 205

Ala Ser Asp Leu Gln Asp Gly Val Pro Ser Arg Phe Ser Gly Ser Gly
    210                 215                 220

Ser Gly Thr Gln Tyr Ser Leu Lys Ile Thr Ser Met Gln Thr Glu Asp
225                 230                 235                 240

Glu Gly Val Tyr Phe Cys Gln Gln Gly Leu Thr Tyr Pro Arg Thr Phe
                245                 250                 255

Gly Gly Gly Thr Lys Leu Glu Leu Lys Arg
            260                 265

<210> SEQ ID NO 60
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atggcctcac cgttgacccg ctttctgtcg ctgaacctgc tgctgctggg tgagtcgatt      60
atcctgggga gtggagaagc tgaagtccag ctgcagcagt ctggggctga gcttgtgaga     120
cctgggacct ctgtgaagtt atcttgcaaa gtttctggcg ataccattac attttactac     180
atgcactttg tgaagcaaag gcctggacag ggtctggaat ggataggaag gattgatcct     240
gaggatgaaa gtactaaata ttctgagaag ttcaaaaaca aggcgacact cactgcagat     300
acatcttcca acacagccta cctgaagctc agcagcctga cctctgagga cactgcaacc     360
tatttttgta tctacggagg atactacttt gattactggg gccaagggg catggtcaca     420 gtctcctcag gtggaggtgg atcaggtgga ggtggatctg gtggaggtgg atctgacatc     480
cagatgacac agtctccagc ttccctgtct acatctctgg gagaaactgt caccatccaa     540
tgtcaagcaa gtgaggacat ttacagtggt ttagcgtggt atcagcagaa gccagggaaa     600
tctcctcagc tcctgatcta tggtgcaagt gacttacaag acggcgtccc atcacgattc     660
agtggcagtg gatctggcac acagtattct ctcaagatca ccagcatgca aactgaagat     720
gaagggtttt atttctgtca acagggttta acgtatcctc ggacgttcgg tggcggcacc     780
aagctggaat tgaaacgg                                                   798

<210> SEQ ID NO 61
<211> LENGTH: 269
<212> TYPE: PRT
<213> ORGANISM: Mus musculus

<400> SEQUENCE: 61

Arg Pro Gln Lys Ser Leu Leu Val Glu Val Glu Glu Gly Gly Asn Val
1               5                   10                  15

Val Leu Pro Cys Leu Pro Asp Ser Ser Pro Val Ser Ser Glu Lys Leu
                20                  25                  30

Ala Trp Tyr Arg Gly Asn Gln Ser Thr Pro Phe Leu Glu Leu Ser Pro
            35                  40                  45

Gly Ser Pro Gly Leu Gly Leu His Val Gly Ser Leu Gly Ile Leu Leu
        50                  55                  60

Val Ile Val Asn Val Ser Asp His Met Gly Gly Phe Tyr Leu Cys Gln
65                  70                  75                  80
```

```
Lys Arg Pro Pro Phe Lys Asp Ile Trp Gln Pro Ala Trp Thr Val Asn
                    85                  90                  95

Val Glu Asp Ser Gly Glu Met Phe Arg Trp Asn Ala Ser Asp Val Arg
            100                 105                 110

Asp Leu Asp Cys Asp Leu Arg Asn Arg Ser Ser Gly Ser His Arg Ser
            115                 120                 125

Thr Ser Gly Ser Gln Leu Tyr Val Trp Ala Lys Asp His Pro Lys Val
            130                 135                 140

Trp Gly Thr Lys Pro Val Cys Ala Pro Arg Gly Ser Ser Leu Asn Gln
145                 150                 155                 160

Ser Leu Ile Asn Gln Asp Leu Thr Val Ala Pro Gly Ser Thr Leu Trp
                    165                 170                 175

Leu Ser Cys Gly Val Pro Pro Val Pro Val Ala Lys Gly Ser Ile Ser
                    180                 185                 190

Trp Thr His Val His Pro Arg Pro Asn Val Ser Leu Leu Ser Leu
                    195                 200                 205                Leu

Ser Leu Gly Gly Glu His Pro Val Arg Glu Met Trp Val Trp Gly Ser
            210                 215                 220

Leu Leu Leu Leu Pro Gln Ala Thr Ala Leu Asp Glu Gly Thr Tyr Tyr
225                 230                 235                 240

Cys Leu Arg Gly Asn Leu Thr Ile Glu Arg His Val Lys Val Ile Ala
                    245                 250                 255

Arg Ser Ala Val Trp Leu Trp Leu Leu Arg Thr Gly Gly
            260                 265

<210> SEQ ID NO 62
<211> LENGTH: 272
<212> TYPE: PRT
<213> ORGANISM: Homo sapiens

<400> SEQUENCE: 62

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
            115                 120                 125

Ser Gly Lys Leu Met Ser Pro Lys Leu Tyr Val Trp Ala Lys Asp Arg
            130                 135                 140

Pro Glu Ile Trp Glu Gly Glu Pro Pro Cys Leu Pro Arg Asp Ser
145                 150                 155                 160

Leu Asn Gln Ser Leu Ser Gln Asp Leu Thr Met Ala Pro Gly Ser Thr
                    165                 170                 175

Leu Trp Leu Ser Cys Gly Val Pro Pro Asp Ser Val Ser Arg Gly Pro
                    180                 185                 190
```

```
Leu Ser Trp Thr His Val His Pro Lys Gly Pro Lys Ser Leu Leu Ser
        195                 200                 205
Leu Glu Leu Lys Asp Asp Arg Pro Ala Arg Asp Met Trp Val Met Glu
    210                 215                 220
Thr Gly Leu Leu Leu Pro Arg Ala Thr Ala Gln Asp Ala Gly Lys Tyr
225                 230                 235                 240
Tyr Cys His Arg Gly Asn Leu Thr Met Ser Phe His Leu Glu Ile Thr
                245                 250                 255
Ala Arg Pro Val Leu Trp His Trp Leu Leu Arg Thr Gly Gly Trp Lys
            260                 265                 270

<210> SEQ ID NO 63
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Ala Leu Pro Val Thr Ala Leu Leu Leu Pro Leu Ala Leu Leu Leu
1               5                   10                  15
His Ala Glu Val Lys Leu Gln Gln Ser Gly Ala Glu Leu Val Arg Pro
            20                  25                  30
Gly Ser Ser Val Lys Ile Ser Cys Lys Ala Ser Gly Tyr Ala Phe Ser
        35                  40                  45
Ser Tyr Trp Met Asn Trp Val Lys Gln Arg Pro Gly Gln Gly Leu Glu
    50                  55                  60
Trp Ile Gly Gln Ile Tyr Pro Gly Asp Gly Asp Thr Asn Tyr Asn Gly
65                  70                  75                  80
Lys Phe Lys Gly Gln Ala Thr Leu Thr Ala Asp Lys Ser Ser Ser Thr
                85                  90                  95
Ala Tyr Met Gln Leu Ser Gly Leu Thr Ser Glu Asp Ser Ala Val Tyr
            100                 105                 110
Phe Cys Ala Arg Lys Thr Ile Ser Ser Val Val Asp Phe Tyr Phe Asp
        115                 120                 125
Tyr Trp Gly Gln Gly Thr Thr Val Thr Val Ser Ser Gly Gly Gly Gly
    130                 135                 140
Ser Gly Gly Gly Gly Ser Gly Gly Gly Gly Ser Asp Ile Glu Leu Thr
145                 150                 155                 160
Gln Ser Pro Lys Phe Met Ser Thr Ser Val Gly Asp Arg Val Ser Val
                165                 170                 175
Thr Cys Lys Ala Ser Gln Asn Val Gly Thr Asn Val Ala Trp Tyr Gln
            180                 185                 190
Gln Lys Pro Gly Gln Ser Pro Lys Pro Leu Ile Tyr Ser Ala Thr Tyr
        195                 200                 205
Arg Asn Ser Gly Val Pro Asp Arg Phe Thr Gly Ser Gly Ser Gly Thr
    210                 215                 220
Asp Phe Thr Leu Thr Ile Thr Asn Val Gln Ser Lys Asp Leu Ala Asp
225                 230                 235                 240
Tyr Phe Cys Gln Gln Tyr Asn Arg Tyr Pro Tyr Thr Ser Gly Gly Gly
                245                 250                 255
Thr Lys Leu Glu Ile Lys Arg
            260
```

```
<210> SEQ ID NO 64
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggctctcc cagtgactgc cctactgctt cccctagcgc ttctcctgca tgcagaggtg      60
aagctgcagc agtctggggc tgagctggtg aggcctgggt cctcagtgaa gatttcctgc     120
aaggcttctg gctatgcatt cagtagctac tggatgaact gggtgaagca gaggcctgga     180
cagggtcttg agtggattgg acagatttat cctggagatg gtgatactaa ctacaatgga     240
aagttcaagg gtcaagccac actgactgca gacaaatcct ccagcacagc ctacatgcag     300
ctcagcggcc taacatctga ggactctgcg gtctatttct gtgcaagaaa gaccattagt     360
tcggtagtag atttctactt tgactactgg ggccaaggga ccacggtcac cgtctcctca     420
ggtggaggtg gatcaggtgg aggtggatct ggtggaggtg gatctgacat tgagctcacc     480
cagtctccaa aattcatgtc cacatcagta ggagacaggg tcagcgtcac ctgcaaggcc     540
agtcagaatg tgggtactaa tgtagcctgg tatcaacaga accaggaca atctcctaaa      600 ccactgattt actcggcaac ctaccggaac agtggagtcc ctgatcgctt cacaggcagt     660
ggatctggga cagatttcac tctcaccatc actaacgtgc agtctaaaga cttggcagac     720
tatttctgtc aacaatataa caggtatccg tacacgtccg agggggggac caagctggag     780
atcaaacgg                                                             789

<210> SEQ ID NO 65
<211> LENGTH: 1368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
atggcctcac cgttgacccg ctttctgtcg ctgaacctgc tgctgctggg tgagtcgatt      60
atcctgggga gtggagaagc tgaagtccag ctgcagcagt ctggggctga gcttgtgaga    120
cctgggacct ctgtgaagtt atcttgcaaa gtttctggcg ataccattac attttactac    180
atgcactttg tgaagcaaag gcctggacag ggtctggaat ggataggaag gattgatcct    240
gaggatgaaa gtactaaata ttctgagaag ttcaaaaaca aggcgacact cactgcagat    300
acatcttcca cacagcccta cctgaagctc agcagcctga cctctgagga cactgcaacc    360
tatttttgta tctacggagg atactacttt gattactggg gccaagggt catggtcaca     420 gtctcctcag gtggaggtgg atcaggtgga ggtggatctg gtggaggtgg atctgacatc    480
cagatgacac agtctccagc ttccctgtct acatctctgg agaaactgt caccatccaa     540 tgtcaagcaa gtgaggacat ttacagtggt ttagcgtggt atcagcagaa gccagggaaa    600
tctcctcagc tcctgatcta tggtgcaagt gacttacaag acggcgtccc atcacgattc    660
agtggcagtg gatctggcac acagtattct ctcaagatca ccagcatgca aactgaagat    720 gaagggggttt atttctgtca acagggttta acgtatcctc ggacgttcgg tggcggcacc    780
aagctggaat tgaaacgggc ggccgcagaa cagaaactga tctctgaaga agacctgatt    840
gagttcatgt accctccgcc ttacctagac aacgagagga gcaatggaac tattattcac    900
```

```
ataaaagaga acatctttg tcatactcag tcatctccta agctgttttg ggcactggtc    960
gtggttgctg gagtcctgtt ttgttatggc ttgctagtga cagtggctct ttgtgttatc   1020
tggacaagag caaaattcag caggagtgca gagactgctg ccaacctgca ggaccccaac   1080
cagctctaca atgagctcaa tctagggcga agagaggaat atgacgtctt ggagaagaag   1140
cgggctcggg atccagagat gggaggcaaa cagcagagga ggaggaaccc ccaggaaggc   1200
gtatacaatg cactgcagaa agacaagatg gcagaagcct acagtgagat cggcacaaaa   1260
ggcgagaggc ggagaggcaa ggggcacgat ggcctttacc agggtctcag cactgccacc   1320
aaggacacct atgatgccct gcatatgcag accctggccc ctcgctaa              1368
```

<210> SEQ ID NO 66
<211> LENGTH: 42
<212> TYPE: PRT
<213> ORGANISM: Homo sapiens

<400> SEQUENCE: 66

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 67
<211> LENGTH: 126
<212> TYPE: DNA
<213> ORGANISM: Homo sapiens

<400> SEQUENCE: 67

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 68
<211> LENGTH: 41
<212> TYPE: PRT
<213> ORGANISM: Mus musculus

<400> SEQUENCE: 68

Asn Ser Arg Arg Asn Arg Leu Leu Gln Ser Asp Tyr Met Asn Met Thr
1               5                   10                  15

Pro Arg Arg Pro Gly Leu Thr Arg Lys Pro Tyr Gln Pro Tyr Ala Pro
            20                  25                  30

Ala Arg Asp Phe Ala Ala Tyr Arg Pro
        35                  40

<210> SEQ ID NO 69
<211> LENGTH: 123
<212> TYPE: DNA
<213> ORGANISM: Mus musculus

<400> SEQUENCE: 69

```
aatagtagaa ggaacagact ccttcaaagt gactacatga acatgactcc ccggaggcct    60
gggctcactc gaaagcctta ccagccctac gcccctgcca gagctttgc agcgtaccgc   120 ccc                                                                 123
```

-continued

<210> SEQ ID NO 70
<211> LENGTH: 41
<212> TYPE: PRT
<213> ORGANISM: Homo sapiens

<400> SEQUENCE: 70

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 71
<211> LENGTH: 123
<212> TYPE: DNA
<213> ORGANISM: Homo sapiens

<400> SEQUENCE: 71
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123

<210> SEQ ID NO 72
<211> LENGTH: 113
<212> TYPE: PRT
<213> ORGANISM: Mus musculus

<400> SEQUENCE: 72

Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
            20                  25                  30

Asp Val Leu Glu Lys Lys Arg Ala Arg Asp Pro Glu Met Gly Gly Lys
        35                  40                  45

Gln Gln Arg Arg Arg Asn Pro Gln Glu Gly Val Tyr Asn Ala Leu Gln
    50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Thr Leu Ala Pro
            100                 105                 110

Arg

<210> SEQ ID NO 73
<211> LENGTH: 339
<212> TYPE: DNA
<213> ORGANISM: Mus musculus

<400> SEQUENCE: 73
agagcaaaat tcagcaggag tgcagagact gctgccaacc tgcaggaccc caaccagctc      60
tacaatgagc tcaatctagg gcgaagagag aatatgacg tcttggagaa gaagcgggct     120
cgggatccag agatgggagg caaacagcag aggaggagga accccagga aggcgtatac     180 aatgcactgc agaaagacaa gatggcagaa gcctacagtg agatcggcac aaaaggcgag     240
aggcggagag gcaaggggca cgatggcctt taccagggtc tcagcactgc caccaaggac     300

```
acctatgatg ccctgcatat gcagaccctg gcccctcgc                               339
```

<210> SEQ ID NO 74
<211> LENGTH: 112
<212> TYPE: PRT
<213> ORGANISM: Homo sapiens

<400> SEQUENCE: 74

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 75
<211> LENGTH: 336
<212> TYPE: DNA
<213> ORGANISM: Homo sapiens

<400> SEQUENCE: 75

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240 cggagggggca aggggcacga tggcctttac cagggtctca gtacagccac caaggacacc   300
tacgacgccc ttcacatgca ggccctgccc cctcgc                             336
```

<210> SEQ ID NO 76
<211> LENGTH: 27
<212> TYPE: PRT
<213> ORGANISM: Mus musculus

<400> SEQUENCE: 76

Phe Trp Ala Leu Val Val Ala Gly Val Leu Phe Cys Tyr Gly Leu
1               5                   10                  15

Leu Val Thr Val Ala Leu Cys Val Ile Trp Thr
            20                  25

<210> SEQ ID NO 77
<211> LENGTH: 81
<212> TYPE: DNA
<213> ORGANISM: Mus musculus

<400> SEQUENCE: 77

```
ttttgggcac tggtcgtggt tgctggagtc ctgttttgtt atggcttgct agtgacagtg    60
gctctttgtg ttatctggac a                                              81
```

<210> SEQ ID NO 78

```
<211> LENGTH: 27
<212> TYPE: PRT
<213> ORGANISM: Homo sapiens

<400> SEQUENCE: 78

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 79
<211> LENGTH: 81
<212> TYPE: DNA
<213> ORGANISM: Homo sapiens

<400> SEQUENCE: 79
ttttgggtgc tggtggtggt tggtggagtc ctggcttgct atagcttgct agtaacagtg      60
gcctttatta ttttctgggt g                                               81

<210> SEQ ID NO 80
<211> LENGTH: 18
<212> TYPE: PRT
<213> ORGANISM: Homo sapiens

<400> SEQUENCE: 80

Met Ala Leu Pro Val Thr Ala Leu Leu Leu Pro Leu Ala Leu Leu Leu
1               5                   10                  15

His Ala
```